United States Patent
Krantz et al.

(10) Patent No.: US 9,770,515 B2
(45) Date of Patent: Sep. 26, 2017

(54) CROSSLINKING OF PROTEINS AND OTHER ENTITIES VIA CONJUGATES OF ALPHA-HALOACETOPHENONES, BENZYL HALIDES, QUINONES, AND THEIR DERIVATIVES

(75) Inventors: Alexander Krantz, Boston, MA (US); Peng Yu, Malden, MA (US)

(73) Assignee: Advanced Proteome Therapeutics Inc., Boston, MA (US)

( * ) Notice: Subject to any disclaimer, the term of this patent is extended or adjusted under 35 U.S.C. 154(b) by 0 days.

(21) Appl. No.: 13/700,944

(22) PCT Filed: Jun. 1, 2011

(86) PCT No.: PCT/US2011/038774
§ 371 (c)(1),
(2), (4) Date: Mar. 18, 2013

(87) PCT Pub. No.: WO2011/153250
PCT Pub. Date: Dec. 8, 2011

(65) Prior Publication Data
US 2013/0165382 A1    Jun. 27, 2013

Related U.S. Application Data

(60) Provisional application No. 61/396,671, filed on Jun. 1, 2010, provisional application No. 61/397,735, filed on Jun. 16, 2010, provisional application No. 61/364,891, filed on Jul. 16, 2010, provisional application No. 61/459,105, filed on Dec. 7, 2010.

(51) Int. Cl.
*A61K 47/48* (2006.01)
*C07K 1/107* (2006.01)
*A61K 39/00* (2006.01)

(52) U.S. Cl.
CPC .. *A61K 47/48215* (2013.01); *A61K 47/48023* (2013.01); *A61K 47/48038* (2013.01); *C07K 1/1077* (2013.01); *A61K 2039/60* (2013.01)

(58) Field of Classification Search
CPC .......... A61K 2039/60; A61K 47/48023; A61K 47/48038; A61K 47/48215; C07K 1/1077
See application file for complete search history.

(56) References Cited

U.S. PATENT DOCUMENTS

| | | | |
|---|---|---|---|
| 6,033,784 A | 3/2000 | Jacobsen et al. | |
| 8,927,485 B2 | 1/2015 | Krantz et al. | |
| 2004/0248765 A1* | 12/2004 | Mincher | A61K 47/48246 514/1.3 |
| 2006/0147443 A1 | 7/2006 | Schense et al. | |
| 2007/0092940 A1* | 4/2007 | Eigenbrot et al. | 435/69.1 |
| 2010/0099649 A1 | 4/2010 | Krantz et al. | |

FOREIGN PATENT DOCUMENTS

| | | | |
|---|---|---|---|
| WO | WO 00/20112 | * | 4/2000 |
| WO | WO 02/42427 A2 | * | 5/2002 |
| WO | WO-2005/074650 A2 | | 8/2005 |
| WO | WO-2006/067376 A2 | | 6/2006 |
| WO | WO-2007/018431 A2 | | 2/2007 |
| WO | WO-2009/037592 A2 | | 3/2009 |
| WO | WO-2009/133362 A2 | | 11/2009 |
| WO | WO-2010/023457 A1 | | 3/2010 |
| WO | WO-2010/040147 A2 | | 4/2010 |

OTHER PUBLICATIONS

Brandt et al, Biochimica et Biophysica Acta, 1975, vol. 386:196-202.*
Loo et. al., J. Med. Chem., vol. 39:4313-4320 (1996).*
Niwa et al., A flexizyme that selectively charges amino acids activated by a water-friendly leaving group, Bioorganic & Medicinal Chemistry Letters, vol. 19:3892-3894 (Mar. 28, 2009).*
Rice et. al., Inhibitors of HIV Nucleocapsid Protein Zinc Fingers as Candidates for the Treatment of AIDS, Science, vol. 270:1194-1197 (Nov. 17, 1995).*
MeSH entry for "Peptide" downloaded Jun. 3, 2015 from www.ncbi.nlm.nih.gov/mesh/68010455.*
Graddis et al. ("Controlled Formation of Model Homo- and Heterodimer Coiled Coil Polypeptides," Biochemistry 1993, 32, 12664-12671).*
Extended European Search Report for European Application No. 11790343.5, mailed May 4, 2016 (17 pages).
Gill et al., "A modular platform for the rapid site-specific radiolabeling of proteins with 18F exemplified by quantitative positron emission tomography of human epidermal growth factor receptor 2," J Med Chem. 52(19):5816-25 (2009).
Li et al., "Site-specific binding of quinones to proteins through thiol addition and addition-elimination reactions," J Am Chem Soc. 127(17):6140-1 (2005).
Supplementary Partial European Search Report for European Application No. 11790343.5, mailed Jan. 15, 2016 (11 pages).
International Search Report for International Application No. PCT/US2011/038774, dated Apr. 16, 2012 (5 pages).
Written Opinion for International Application No. PCT/US2011/038774, dated Apr. 16, 2012 (7 pages).

\* cited by examiner

*Primary Examiner* — Christina Bradley
(74) *Attorney, Agent, or Firm* — Clark & Elbing LLP

(57) ABSTRACT

The present invention relates to the formation of conjugates (e.g., protein-protein dimers) using a-halo-acetophenones, benzylic halides, quinones, and related compounds as a conjugating system. The invention also features compositions that include the conjugates described herein, as well as uses of these conjugates in methods of medical treatment.

10 Claims, No Drawings

CROSSLINKING OF PROTEINS AND OTHER ENTITIES VIA CONJUGATES OF ALPHA-HALOACETOPHENONES, BENZYL HALIDES, QUINONES, AND THEIR DERIVATIVES

CROSS-REFERENCE TO RELATED APPLICATIONS

This application is the U.S. National Stage of International Application No. PCT/US2011/038774, filed Jun. 1, 2011, which claims benefit of U.S. Provisional Patent Application Nos. 61/396,671, filed Jun. 1, 2010, 61/397,735, filed Jun. 16, 2010, 61/364,891, filed Jul. 16, 2010, and 61/459,105, filed Dec. 7, 2010, each of which is hereby incorporated by reference in its entirety.

FIELD OF THE INVENTION

The present invention relates to the formation of conjugates using α-halo-acetophenones, benzylic halides, quinones, and related functional groups for the formation of covalent bonds. The conjugates prepared according to these methods, along with other protein conjugates and/or fusion proteins, can be used in radio-labeling, molecular imaging, methods of medical treatment (e.g., targeted drug delivery), and protein applications.

BACKGROUND OF THE INVENTION

Protein conjugation lies at the heart of the discovery and development of protein therapeutics. Chemical modification strategies typically employ a two step process where the first step involves site-specific modification of the protein and the second step is the installation of an entity of interest. The step involving modification of the protein can be difficult to effect site-specifically by chemical methods in view of the presence of many peptide residues of the same type. Accordingly, limited success has been achieved in such site-specific modifications, although enzymes have been targets of these transformations. For example, it has been demonstrated that group modification agents with minimal binding determinants can sometimes react site-specifically at enzyme active sites, e.g., active site serines of proteinases (Means et al., *Chemical Modification of Proteins*, Holden-Day, Inc., San Francisco, 1971.)

For proteins that have not evolved to do such chemistry, the challenges for site-specific labeling are far greater than for the construction of active-site directed reagents. For such proteins the challenges can be likened to the development of site-specific modifications of non-active site residues of enzymes. Thus, other than for active-sites, and allosteric sites that have evolved to bind enzyme modulators, site-specific labeling reagents (affinity labels) are lacking and novel approaches are required to fill that void. Amino acid residues usually have little to distinguish their reactivity from others in the same class, with the exception of cysteine thiols whose chemistry is quite distinct from other peptidic side chain functionality. Alternatively, strategies that employ the reaction chemistry of thiols can be useful for the selective modification of proteins, but have not been fully exploited. Current methods are limited in several respects. For example, the most commonly used thiol-specific reagent are maleimide-based, and these produce enantiomers upon reaction. Further, there are storage and stability issues with maleimide functionality as the initial adducts have a tendency to decompose over time.

For these reasons, methods for the site-specific modification and ligation of proteins would be useful for the synthesis of modified peptide, polypeptide, and protein conjugates and provide conjugates for radio-labeling, molecular imaging and protein therapeutic applications, and in methods of medical treatment that are stable and homogeneous.

SUMMARY OF THE INVENTION

In a first aspect, the invention features a conjugate having the following structure,

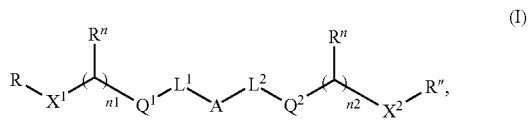

where
A is optionally substituted aryl, optionally substituted heteroaryl, or a substructure according to the formula $-Ar^{Z1}-Z-Ar^{Z2}-$, where
  each of $Ar^{Z1}$ and $Ar^{Z2}$ is, independently, optionally substituted aryl or optionally substituted heteroaryl, and
  Z is a covalent bond, O, S, $NR^{Z1}$, where $R^{Z1}$ is H or optionally substituted C1-6 alkyl, an optionally substituted C1-20 alkylene, a polyethylene glycol of the structure $(CH_2CH_2O)(CH_2CH_2O)_n(CH_2CH_2)$, where n is an integer between 0-1000, or a linking group having the structure $-X^{Z1}-(Q^{Z1})_{n3}-R^{Z2}-(Q^{Z1})_{n4}X^{Z1}$, where
  each of n3 and n4 is, independently, 0 or 1,
  each $X^{Z1}$ is, independently, a covalent bond, O, S, or $NR^{Z1}$,
  each $Q^{Z1}$ is, independently, C(=O), S(=O), or $S(=O)_2$, and
  $R^{Z2}$ is optionally substituted C1-20 alkylene or polyethylene oxide $(CH_2CH_2O)(CH_2CH_2O)_n(CH_2CH_2)$, where n is an integer between 0-1000;
each of $L^1$ and $L^2$ is, independently, a covalent bond or optionally substituted C1-C6 alkylene;
each of $Q^1$ and $Q^2$ is, independently, a covalent bond, C(=O), $S(=O)_2$, or optionally substituted C1 alkylene;
each of n1 and n2 is, independently, 0 or 1;
each of $X^1$ and $X^2$ is, independently, O, S, or $NR^X$, wherein $R^X$ is H or optionally substituted C1-6 alkyl;
each $R^n$ is, independently, H or optionally substituted C1-6 alkyl; and
each of R and R" is, independently, a protein, a biologically active agent, or a biologically compatible agent.

In some embodiments, Z is an optionally substituted C1-20 alkylene.
In some embodiments, $L^1$ is a covalent bond.
In other embodiments, $L^2$ is a covalent bond.
In certain embodiments, n1 is 1.
In still other embodiments, n2 is 1.
In some embodiments, $Q^1$ is C(=O), $S(=O)_2$, CHOH, or $CH_2$.
In certain embodiments, $Q^1$ is a covalent bond.
In other embodiments, $Q^2$ is C(=O), $S(=O)_2$, CHOH, or $CH_2$.
In certain embodiments, $Q^2$ is a covalent bond.
In some embodiments, R is a protein (e.g., a protein that is an annexin protein, an antibody, a cytokine, a wild-type protein that includes a free cysteine residue, or a protein modified to include a free cysteine residue).

In other embodiments, R is a biologically active agent or a biologically compatible agent (e.g., a biologically active or biologically compatible agent that includes a polymer, nucleic acid, carbohydrate (e.g., a monosaccharide, a disaccharide, an oligosaccharide, or a polysaccharide), small molecule therapeutic agent, imaging agent, or diagnostic agent).

In certain embodiments, R" is a protein (e.g., a protein that is an annexin protein, an antibody, a cytokine, a wild-type protein that includes a free cysteine residue, or a protein modified to include a free cysteine residue).

In other embodiments, R" is a biologically active or biologically compatible agent (e.g., a biologically active or biologically compatible agent that includes a polymer, nucleic acid, carbohydrate (e.g., a monosaccharide, a disaccharide, an oligosaccharide, or a polysaccharide), small molecule therapeutic agent, imaging agent, or diagnostic agent).

In some embodiments, A is optionally substituted phenyl, optionally substituted naphthyl, or optionally substituted biphenyl (e.g., A is unsubstituted phenyl, unsubstituted naphthyl, or unsubstituted biphenyl).

In some embodiments, A is a substructure according to the formula —$Ar^{Z1}$—Z—$Ar^{Z2}$—. In further embodiments, $Ar^{Z1}$ and $A^{Z2}$ are both phenyl, and Z is a covalent bond, O, optionally substituted C1-20 alkylene, or $(CH_2CH_2O)(CH_2CH_2O)_n(CH_2CH_2)$, wherein n is an integer between 0-1000.

In some embodiments, $X^1$ is S and/or $X^2$ is S.

In other embodiments, one or both R" groups is H or $CH_3$. In further embodiments, both R" groups are H or both are $CH_3$.

In certain embodiments, the conjugate has a structure according to one of the following formulas,

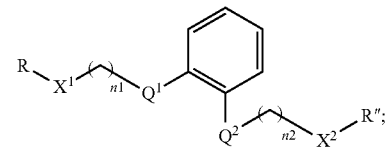
(II-A)

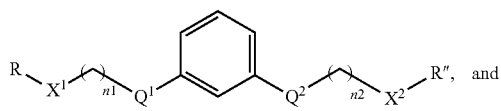
(II-B)

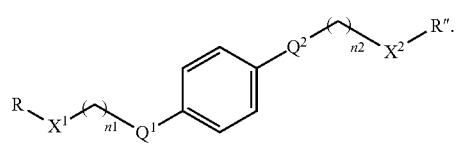
(II-C)

In some embodiments, $Q^1$ is C(=O), S(=O)$_2$, CHOH, or $CH_2$.

In other embodiments, n1 is 1.

In certain embodiments, the conjugate has a structure according to one of the following formulas,

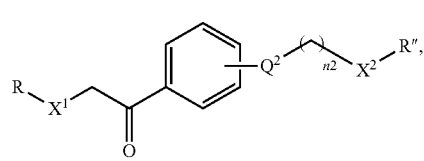
(II-D)

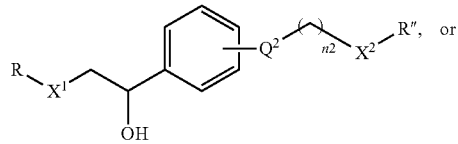
(II-E)

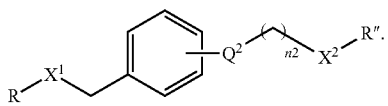
(II-F)

In other embodiments, $Q^2$ is C(=O), S(=O)$_2$, CHOH, or $CH_2$.

In still other embodiments, n2 is 1.

In some embodiments, n2 is 0.

In other embodiments, $X^1$ is S.

In certain embodiments, $X^2$ is S.

In some embodiments, $X^2$ is NH.

In other embodiments, the conjugate has a structure according to the following formula,

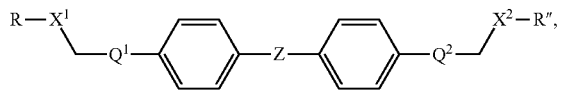

where each of $Q^1$ and $Q^2$ is, independently, a covalent bond, C=O, or CHOH Can't be correct; produces unstable species.

In certain embodiments, Z is a covalent bond, O, optionally substituted C1-20 alkylene, or $(CH_2CH_2O)(CH_2CH_2O)_n(CH_2CH_2)$, wherein n is an integer between 0-1000.

In other embodiments, one or both of R and R" is a protein (e.g., a protein that is an annexin protein, an antibody, a cytokine, a wild-type protein that includes a free cysteine residue, or a protein modified to include a free cysteine residue).

In other embodiments, one or both of R and R" is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features a conjugate having a structure according to the following formula,

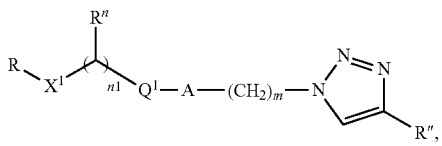

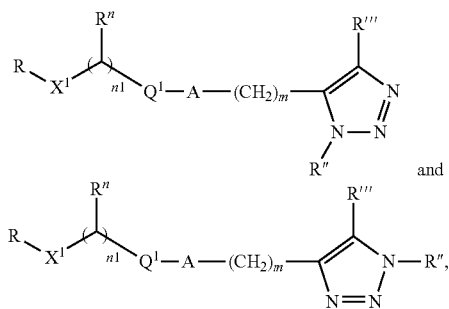

where
m is an integer between 0-20;
A is optionally substituted aryl, optionally substituted heteroaryl, or a substructure according to the formula —$Ar^{Z1}$—Z—$Ar^{Z2}$—, where
each of $Ar^{Z1}$ and $Ar^{Z2}$ is, independently, optionally substituted aryl or optionally substituted heteroaryl, and
Z is a covalent bond, O, S, $NR^{Z1}$, where $R^{Z1}$ is H or optionally substituted C1-6 alkyl, an optionally substituted C1-20 alkylene, a polyethylene glycol of the structure $(CH_2CH_2O)(CH_2CH_2O)_n(CH_2CH_2)$, where n is an integer between 0-1000, or a linking group having the structure —$X^{Z1}$-$(Q^{Z1})_{n3}$-$R^{Z2}$-$(Q^{Z1})_{n4}X^{Z1}$, where
each of n3 and n4 is, independently, 0 or 1,
each $X^{Z1}$ is, independently, a covalent bond, O, S, or $NR^{Z1}$,
each $Q^{Z1}$ is, independently, C(=O), S(=O), or S(=O)$_2$, and
$R^{Z2}$ is optionally substituted C1-20 alkylene or $(CH_2CH_2O)(CH_2CH_2O)_n(CH_2CH_2)$, where n is an integer between 0-1000;
$Q^1$ is C(=O), S(=O)$_2$, or optionally substituted C1 alkylene;
n1 is 0 or 1;
$X^1$ is O, S, or $NR^X$, where $R^X$ is H or optionally substituted C1-6 alkyl;
each $R''$ is, independently, H or optionally substituted C1-6 alkyl; and
each of R and R'' is, independently, a protein or a biologically active or biologically compatible agent.

In other embodiments, one or both of R and R'' is a protein (e.g., a protein that is an annexin protein, an antibody, a cytokine, a wild-type protein that includes a free cysteine residue, or a protein modified to include a free cysteine residue).

In other embodiments, one or both of R and R'' is a biologically active agent or a biologically compatible agent (e.g., a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R'' is an annexin protein, and the other is an antibody, a cytokine, a biologically active agent, or a biologically compatible agent.

In yet another aspect, the invention features a conjugate having a structure according to a formula selected from, where
m is an integer between 0-20;
A is optionally substituted aryl, optionally substituted heteroaryl, or a substructure according to the formula —$Ar^{Z1}$—Z—$Ar^{Z2}$—, where
each of $Ar^{Z1}$ and $Ar^{Z2}$ is, independently, optionally substituted aryl or optionally substituted heteroaryl, and
Z is a covalent bond, O, S, $NR^{Z1}$, where $R^{Z1}$ is H or optionally substituted C1-6 alkyl, an optionally substituted C1-20 alkylene, a polyethylene glycol of the structure $(CH_2CH_2O)(CH_2CH_2O)_n(CH_2CH_2)$, where n is an integer between 0-1000, or a linking group having the structure —$X^{Z1}$-$(Q^{Z1})_{n3}$-$R^{Z2}$-$(Q^{Z1})_{n4}X^{Z1}$, where
each of n3 and n4 is, independently, 0 or 1,
each $X^{Z1}$ is, independently, a covalent bond, O, S, or $NR^{Z1}$,
each $Q^{Z1}$ is, independently, C(=O), S(=O), or S(=O)$_2$, and
$R^{Z2}$ is optionally substituted C1-20 alkylene or $(CH_2CH_2O)(CH_2CH_2O)_n(CH_2CH_2)$, where n is an integer between 0-1000;
$Q^1$ is C(=O), S(=O)$_2$, or optionally substituted C1 alkylene;
n1 is 0 or 1;
$X^1$ is O, S, or $NR^X$, where $R^X$ is H or optionally substituted C1-6 alkyl;
each $R''$ is, independently, H or optionally substituted C1-6 alkyl;
each of R and R'' is, independently, a protein or a biologically active or biologically compatible agent; and
$R'''$ is H, optionally substituted C1-20 alkyl, a protein, or a biologically active or biologically compatible agent.

In other embodiments, one or both of R and R'' is a protein (e.g., a protein that is an annexin protein, an antibody, a cytokine, a wild-type protein that includes a free cysteine residue, or a protein modified to include a free cysteine residue).

In other embodiments, one or both of R and R'' is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features method of preparing a conjugate having the following structure,

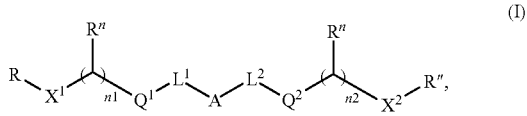

where the method includes
(a) contacting a compound according to the following formula,

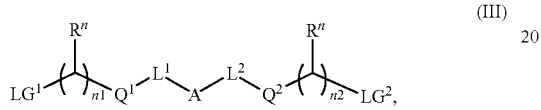

where
A is optionally substituted aryl, optionally substituted heteroaryl, or a substructure according to the formula —Ar$^{Z1}$—Z—Ar$^{Z2}$—, where
  each of Ar$^{Z1}$ and Ar$^{Z2}$ is, independently, optionally substituted aryl or optionally substituted heteroaryl, and
  Z is a covalent bond, O, S, NR$^{Z1}$, where R$^{Z1}$ is H or optionally substituted C1-6 alkyl, an optionally substituted C1-20 alkylene, a polyethylene glycol of the structure (CH$_2$CH$_2$O)(CH$_2$CH$_2$O)$_n$(CH$_2$CH$_2$), where n is an integer between 0-1000, or a linking group having the structure —X$^{Z1}$-(Q$^{Z1}$)$_{n3}$-R$^{Z2}$-(Q$^{Z1}$)$_{n4}$X$^{Z1}$, where
    each of n3 and n4 is, independently, 0 or 1,
    each X$^{Z1}$ is, independently, a covalent bond, O, S, or NR$^{Z1}$,
    each Q$^{Z1}$ is, independently, C(=O), S(=O), or S(=O)$_2$, and
    R$^{Z2}$ is optionally substituted C1-20 alkylene or (CH$_2$CH$_2$O)(CH$_2$CH$_2$O)$_n$(CH$_2$CH$_2$), where n is an integer between 0-1000;
each of L$^1$ and L$^2$ is, independently, a covalent bond or optionally substituted C1-C6 alkylene;
each of Q$^1$ and Q$^2$ is, independently, C(=O), S(=O)$_2$, or optionally substituted C1 alkylene;
each of n1 and n2 is, independently, 0 or 1;
each R" is, independently, H or optionally substituted C1-6 alkyl; and
each of LG$^1$ and LG$^2$ is, independently, a leaving group, with
a nucleophilic compound having the structure RX$^1$H, where R is a protein or a biologically active or biologically compatible agent, and X$^1$ is O, S, or NR$^X$, where R$^X$ is H or optionally substituted C1-6 alkyl; and and
(b) contacting the product of step (a) with a nucleophilic compound having the structure R"X$^2$H, where R" is a protein or a biologically active or biologically compatible agent, and X$^2$ is O, S, or NR$^X$, where R$^X$ is H or optionally substituted C1-6 alkyl.

In some embodiments, each of LG$^1$ and LG$^2$ is, independently, F, Cl, Br, I, OSO$_2$R$^{LG}$, OR$^{LG}$, or OC(=O)OR$^{LG}$, where R$^{LG}$ is optionally substituted C1-6 alkyl or optionally substituted aryl.

In other embodiments, -L$^1$Q$^1$(CH$_2$)$_{n1}$LG$^1$ is —C(=O)CH$_2$LG$^1$, —C(=O)CHCH$_3$LG$^1$, —C(=O)LG$^1$, —S(=O)$_2$CH$_2$LG$^1$, —CH$_2$LG$^1$, or —CHCH$_3$LG$^1$.

In some embodiments, LG$^1$ is F, Cl, Br, I, OSO$_2$CH$_3$, or OSO$_2$(p-CH$_3$C$_6$H$_4$).

In certain embodiments, -L$^2$Q$^2$(CH$_2$)$_{n2}$LG$^2$ is —C(=O)CH$_2$LG$^2$, —C(=O)CHCH$_3$LG$^2$, —C(=O)LG$^2$, —S(=O)$_2$CH$_2$LG$^2$, —CH$_2$LG$^2$, or —CHCH$_3$LG$^2$.

In still other embodiments, LG$^2$ is F, Cl, Br, I, OSO$_2$CH$_3$, or OSO$_2$(p-CH$_3$C$_6$H$_4$).

In another aspect, the invention features a method of preparing a conjugate having the following structure,

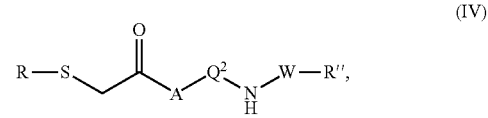

including
(a) contacting a compound having the following structure,

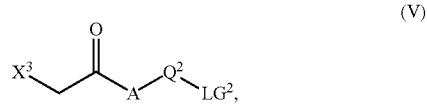

where X$^3$ is F, Cl, Br, or I,
A is optionally substituted aryl, optionally substituted heteroaryl, or a substructure according to the formula —Ar$^{Z1}$—Z—Ar$^{Z2}$—, where
  each of Ar$^{Z1}$ and Ar$^{Z2}$ is, independently, optionally substituted aryl or optionally substituted heteroaryl, and
  Z is a covalent bond, O, S, NR$^{Z1}$, where R$^{Z1}$ is H or optionally substituted C1-6 alkyl, an optionally substituted C1-20 alkylene, a polyethylene glycol of the structure (CH$_2$CH$_2$O)(CH$_2$CH$_2$O)$_n$(CH$_2$CH$_2$), where n is an integer between 0-1000, or a linking group having the structure —X$^{Z1}$-(Q$^{Z1}$)$_{n3}$-R$^{Z2}$-(Q$^{Z1}$)$_{n4}$X$^{Z1}$, where
    each of n3 and n4 is, independently, 0 or 1,
    each X$^{Z1}$ is, independently, a covalent bond, O, S, or NR$^{Z1}$,
    each Q$^{Z1}$ is, independently, C(=O), S(=O), or S(=O)$_2$, and
    R$^{Z2}$ is optionally substituted C1-20 alkylene or (CH$_2$CH$_2$O)(CH$_2$CH$_2$O)$_n$(CH$_2$CH$_2$), where n is an integer between 0-1000;
Q$^2$ is C(=O) or S(=O)$_2$, and
LG$^2$ is a leaving group selected from Cl, OH, OR$^{LG}$, OC(=O)OR$^{LG}$, or OC(=NR$^{LG}$)NHR$^{LG}$, where each R$^{LG}$ is, independently, optionally substituted C1-C6 alkyl or optionally substituted C3-C9 cycloalkyl, with
an amino nucleophile having the structure NH$_2$WR", where R" is a protein or biologically active or biologically compatible agent, and W is H, O NR$^W$, or NC(=O), where R$^W$ is H or optionally substituted C1-C6 alkyl, optionally in the presence of a peptide coupling reagent; and
(b) contacting the product of step (a) having the following formula,

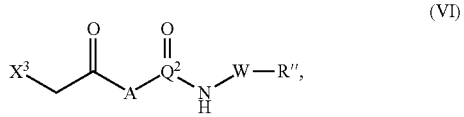

(VI)

with a thiol nucleophile having the structure RSH, where R is a protein or biologically active or biologically compatible agent.

In some embodiments, one equivalent of the amino nucleophile is used.

In some embodiments, A is optionally substituted phenyl, optionally substituted naphthyl, optionally substituted furyl, or optionally substituted thienyl. In further embodiments, A is ortho-phenyl, meta-phenyl, or para-phenyl.

In other embodiments, A is a substructure according to the formula —Ar$^{Z1}$—Z—Ar$^{Z1}$—. In still other embodiments, and A$^{Z2}$ are both phenyl, and Z is a covalent bond, O, optionally substituted C1-20 alkylene, or —(CH$_2$CH$_2$O)(CH$_2$CH$_2$O)$_n$(CH$_2$CH$_2$)—, where n is an integer between 0-1000.

In some embodiments, at least one of R and R" is a protein. In some embodiments, both R and R" are proteins. In further embodiments, the protein is an annexin protein, an antibody, a cytokine, a wild-type protein that includes a free cysteine residue, or a protein modified to include a free cysteine residue.

In some embodiments, at least one of R and R" is a polymer, nucleic acid, carbohydrate, small molecule therapeutic agent, imaging agent, or diagnostic agent (e.g., a radionucleotide, a small molecule therapeutic agent, an optical label, a fluorescent label, a biosynthetic label, or an oligonucleotide). In some embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetraacetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features a method of preparing a conjugate having the following structure,

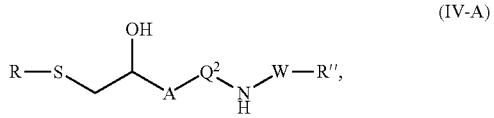

(IV-A)

including
(a) contacting a compound having the following structure,

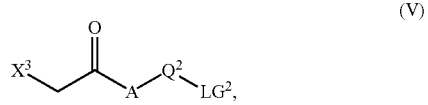

(V)

where X$^3$ is F, Cl, Br, or I, where
A is optionally substituted aryl, optionally substituted heteroaryl, or a substructure according to the formula —Ar$^{Z1}$—Z—Ar$^{Z2}$—, where each of Ar$^{Z1}$ and Ar$^{Z2}$ is, independently, optionally substituted aryl or optionally substituted heteroaryl, and Z is a covalent bond, O, S, NR$^{Z1}$, where R$^{Z1}$ is H or optionally substituted C1-6 alkyl, an optionally substituted C1-20 alkylene, a polyethylene glycol of the structure (CH$_2$CH$_2$O)(CH$_2$CH$_2$O)$_n$(CH$_2$CH$_2$), where n is an integer between 0-1000, or a linking group having the structure —X$^{Z1}$-(Q$^{Z1}$)$_{n3}$-R$^{Z2}$-(Q$^{Z1}$)$_{n4}$X$^{Z1}$, where each of n3 and n4 is, independently, 0 or 1, each X$^{Z1}$ is, independently, a covalent bond, O, S, or NR$^{Z1}$, each Q$^{Z1}$ is, independently, C(=O), S(=O), or S(=O)$_2$, and R$^{Z2}$ is optionally substituted C1-20 alkylene or (CH$_2$CH$_2$O)(CH$_2$CH$_2$O)$_n$(CH$_2$CH$_2$), where n is an integer between 0-1000;

Q$^2$ is C(=O) or S(=O)$_2$, and

LG$^2$ is a leaving group selected from Cl, OH, OR$^{LG}$, OC(=O)OR$^{LG}$, or OC(=NR$^{LG}$)NHR$^{LG}$, where each R$^{LG}$ is, independently, optionally substituted C1-C6 alkyl or optionally substituted C3-C9 cycloalkyl, with an amino nucleophile having the structure NH$_2$WR", where R" is a protein or biologically active or biologically compatible agent, and W is H, O NR$^W$, or NC(=O), where R$^W$ is H or optionally substituted C1-C6 alkyl, optionally in the presence of a peptide coupling reagent; and (b) contacting the product of step (a) having the following formula,

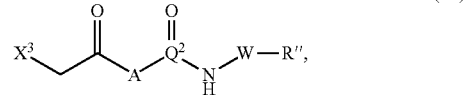

(VI)

with a thiol nucleophile having the structure RSH, where R is a protein or biologically active or biologically compatible agent; and (c) subjecting a composition including the product of step (b) to reducing conditions.

In some embodiments, one equivalent of the amine nucleophile is used.

In some embodiments, NaBH$_3$CN is used in step (c).

In some embodiments, A is optionally substituted phenyl, optionally substituted naphthyl, optionally substituted furyl, or optionally substituted thienyl. In further embodiments, A is ortho-phenyl, meta-phenyl, or para-phenyl.

In other embodiments, A is a substructure according to the formula —Ar$^{Z1}$—Z—Ar$^{Z2}$—. In still other embodiments, Ar$^{Z1}$ and A$^{Z2}$ are both phenyl, and Z is a covalent bond, O, optionally substituted C1-20 alkylene, or —(CH$_2$CH$_2$O)(CH$_2$CH$_2$O)$_n$(CH$_2$CH$_2$)—, where n is an integer between 0-1000.

In some embodiments, at least one of R and R" is a protein. In some embodiments, both R and R" are proteins. In further embodiments, the protein is an annexin protein, an antibody, a cytokine, a wild-type protein that includes a free cysteine residue, or a protein modified to include a free cysteine residue.

In some embodiments, at least one of R and R" is a polymer, nucleic acid, carbohydrate, small molecule therapeutic agent, imaging agent, or diagnostic agent (e.g., a radionucleotide, a small molecule therapeutic agent, an optical label, a fluorescent label, a biosynthetic label, or an oligonucleotide). In some embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features a method of preparing conjugates having the following structure,

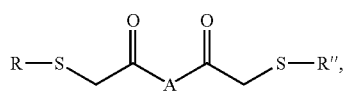

(VII)

comprising
(a) contacting a compound having the structure RSH, where R is a protein or a biologically active or biologically compatible agent with a compound having the following structure,

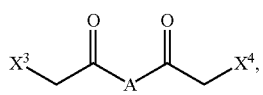

(VIII)

wherein each of $X^3$ and $X^4$ is, independently F, Cl, Br, or I, and

A is optionally substituted aryl, optionally substituted heteroaryl, or a substructure according to the formula —$Ar^{Z1}$—Z—$Ar^{Z2}$—, wherein
each of $Ar^{Z1}$ and $Ar^{Z2}$ is, independently, optionally substituted aryl or optionally substituted heteroaryl, and
Z is a covalent bond, O, S, $NR^{Z1}$, wherein $R^{Z1}$ is H or optionally substituted C1-6 alkyl, an optionally substituted C1-20 alkylene, a polyethylene glycol of the structure $(CH_2CH_2O)(CH_2CH_2O)_n(CH_2CH_2)$, wherein n is an integer between 0-1000, or a linking group having the structure —$X^{Z1}$-$(Q^{Z1})_{n3}$-$R^{Z2}$-$(Q^{Z1})_{n4}X^{Z1}$, wherein
each of n3 and n4 is, independently, 0 or 1,
each $X^{Z1}$ is, independently, a covalent bond, O, S, or $NR^{Z1}$,
each $Q^{Z1}$ is, independently, C(=O), S(=O), or $S(=O)_2$, and
$R^{Z2}$ is optionally substituted C1-20 alkylene or $(CH_2CH_2O)(CH_2CH_2O)_n(CH_2CH_2)$, wherein n is an integer between 0-1000; and
(b) contacting the product of step (a) having the following formula,

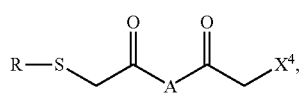

(IX)

with a compound having the structure R"SH, wherein R is a protein or a biologically active or biologically compatible agent.

In some embodiments, A is optionally substituted phenyl, optionally substituted naphthyl, optionally substituted furyl, or optionally substituted thienyl. In further embodiments, A is ortho-phenyl, meta-phenyl, or para-phenyl.

In other embodiments, A is a substructure according to the formula —$Ar^{Z1}$—Z—$Ar^{Z2}$—. In still other embodiments, $Ar^{Z1}$ and $A^{z2}$ are both phenyl, and Z is a covalent bond, O, optionally substituted C1-20 alkylene, or —$(CH_2CH_2O)$ $(CH_2CH_2O)_n(CH_2CH_2)$—, where n is an integer between 0-1000.

In some embodiments, at least one of R and R" is a protein. In some embodiments, both R and R" are proteins. In further embodiments, the protein is an annexin protein, an antibody, a cytokine, a wild-type protein that includes a free cysteine residue, or a protein modified to include a free cysteine residue.

In some embodiments, at least one of R and R" is a polymer, nucleic acid, carbohydrate, small molecule therapeutic agent, imaging agent, or diagnostic agent (e.g., a radionucleotide, a small molecule therapeutic agent, an optical label, a fluorescent label, a biosynthetic label, or an oligonucleotide). In some embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features a method of preparing conjugates having the following structure,

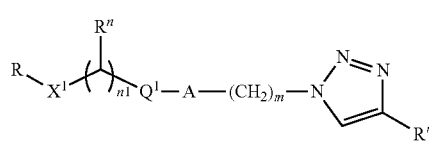

(X)

the method including
contacting
(i) a compound having the following structure,

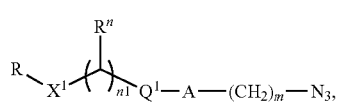

(XI)

where
m is an integer between 0-20;
A is optionally substituted aryl, optionally substituted heteroaryl, or a substructure according to the formula —$Ar^{Z1}$—Z—$Ar^{Z2}$—, where
each of $Ar^{Z1}$ and $Ar^{Z2}$ is, independently, optionally substituted aryl or optionally substituted heteroaryl, and
Z is a covalent bond, O, S, $NR^{Z1}$, where $R^{Z1}$ is H or optionally substituted C1-6 alkyl, an optionally substituted C1-20 alkylene, a polyethylene glycol of the structure (CH$_2$CH$_2$O)(CH$_2$CH$_2$O)$_n$(CH$_2$CH$_2$), where n is an integer between 0-1000, or a linking group having the structure —X$^{Z1}$-(Q$^{Z1}$)$_{n3}$-R$^{Z2}$-(Q$^{Z1}$)$_{n4}$X$^{Z1}$, where each of n3 and n4 is, independently, 0 or 1,
each X$^{Z1}$ is, independently, a covalent bond, O, S, or NR$^{Z1}$,
each Q$^{Z1}$ is, independently, C(=O), S(=O), or S(=O)$_2$, and
R$^{Z2}$ is optionally substituted C1-20 alkylene or (CH$_2$CH$_2$O)(CH$_2$CH$_2$O)$_n$(CH$_2$CH$_2$), where n is an integer between 0-1000;
Q$^1$ is a covalent bond, C(=O), S(=O)$_2$, or optionally substituted C1 alkylene;
n1 is 0 or 1;
X$^1$ is O, S, or NR$^X$, where R$^X$ is H or optionally substituted C1-6 alkyl;
each is, independently, H or optionally substituted C1-6 alkyl; and
R is a protein or a biologically active or biologically compatible agent, with
(ii) a compound having the structure HC≡C—R", where R" is a protein or a biologically active or biologically compatible agent.
In some embodiments, A is optionally substituted phenyl, optionally substituted naphthyl, optionally substituted furyl, or optionally substituted thienyl. In further embodiments, A is ortho-phenyl, meta-phenyl, or para-phenyl.
In other embodiments, A is a substructure according to the formula —Ar$^{Z1}$—Z—Ar$^{Z2}$—. In still other embodiments, Ar$^{Z1}$ and A$^{Z2}$ are both phenyl, and Z is a covalent bond, O, optionally substituted C1-20 alkylene, or —(CH$_2$CH$_2$O)(CH$_2$CH$_2$O)$_n$(CH$_2$CH$_2$)—, where n is an integer between 0-1000.
In some embodiments, at least one of R and R" is a protein. In some embodiments, both R and R" are proteins. In further embodiments, the protein is an annexin protein, an antibody, a cytokine, a wild-type protein that includes a free cysteine residue, or a protein modified to include a free cysteine residue.
In some embodiments, at least one of R and R" is a polymer, nucleic acid, carbohydrate, small molecule therapeutic agent, imaging agent, or diagnostic agent (e.g., a radionucleotide, a small molecule therapeutic agent, an optical label, a fluorescent label, a biosynthetic label, or an oligonucleotide). In some embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.
In certain embodiments, one of R and R" is an annexin protein, and the other is an antibody, a cytokine, a biologically active agent, or a biologically compatible agent.
In another aspect, the invention features a method of preparing conjugates having the following structure,

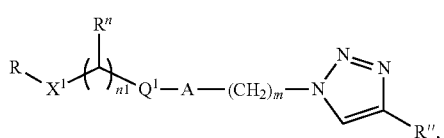

(X)

the method including
(i) contacting a compound having the following structure,

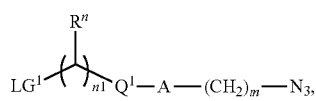

(XII)

where
LG$^1$ is F, Cl, Br, or I,
m is an integer between 0-20;
A is optionally substituted aryl, optionally substituted heteroaryl, or a substructure according to the formula —Ar$^{Z1}$—Z—Ar$^{Z2}$—, where
each of Ar$^{Z1}$ and Ar$^{Z2}$ is, independently, optionally substituted aryl or optionally substituted heteroaryl, and
Z is a covalent bond, O, S, NR$^{Z1}$, where R$^{Z1}$ is H or optionally substituted C1-6 alkyl, an optionally substituted C1-20 alkylene, a polyethylene glycol of the structure (CH$_2$CH$_2$O)(CH$_2$CH$_2$O)$_n$(CH$_2$CH$_2$), where n is an integer between 0-1000, or a linking group having the structure —X$^{Z1}$-(Q$^{Z1}$)$_{n3}$-R$^{Z2}$-(Q$^{Z1}$)$_{n4}$X$^{Z1}$, where each of n3 and n4 is, independently, 0 or 1,
each X$^{Z1}$ is, independently, a covalent bond, O, S, or NR$^{Z1}$,
each Q$^{Z1}$ is, independently, C(=O), S(=O), or S(=O)$_2$, and
R$^{Z2}$ is optionally substituted C1-20 alkylene or (CH$_2$CH$_2$O)(CH$_2$CH$_2$O)$_n$(CH$_2$CH$_2$), where n is an integer between 0-1000;
Q$^1$ is C(=O), S(=O)$_2$, or optionally substituted C1 alkylene; (benzyl claim?)
n1 is 0 or 1;
X$^1$ is O, S, or NR$^X$, where R$^X$ is H or optionally substituted C1-6 alkyl; and
each is, independently, H or optionally substituted C1-6 alkyl;
with
a compound having the structure HC≡C—R", where R" is a protein or a biologically active or biologically compatible agent; and
(ii) treating the product of step (i), where the product has a structure according to the following formula,

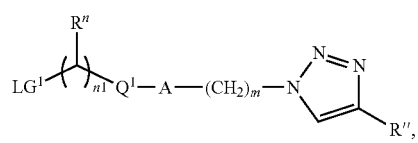

(XIII)

with a compound having the structure R—X$^1$H, where R is a protein or a biologically active or biologically compatible agent, and X' is O, S, or NR$^X$, where R$^X$ is H or optionally substituted C1-6 alkyl.
In some embodiments, A is optionally substituted phenyl, optionally substituted naphthyl, optionally substituted furyl, or optionally substituted thienyl. In further embodiments, A is ortho-phenyl, meta-phenyl, or para-phenyl.
In other embodiments, A is a substructure according to the formula —Ar$^{Z1}$—Z—Ar$^{Z2}$—. In still other embodiments, Ar$^{Z1}$ and A$^{Z2}$ are both phenyl, and Z is a covalent bond, O, optionally substituted C1-20 alkylene, or —(CH$_2$CH$_2$O)(CH$_2$CH$_2$O)$_n$(CH$_2$CH$_2$)—, where n is an integer between 0-1000.

In some embodiments, at least one of R and R" is a protein. In some embodiments, both R and R" are proteins. In further embodiments, the protein is an annexin protein, an antibody, a cytokine, a wild-type protein that includes a free cysteine residue, or a protein modified to include a free cysteine residue.

In some embodiments, at least one of R and R" is a polymer, nucleic acid, carbohydrate, small molecule therapeutic agent, imaging agent, or diagnostic agent (e.g., a radionucleotide, a small molecule therapeutic agent, an optical label, a fluorescent label, a biosynthetic label, or an oligonucleotide). In some embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In still another aspect, the invention features a method of preparing a conjugate having a structure according to a formula selected from,

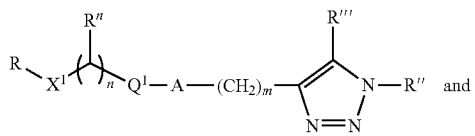
(XIV)

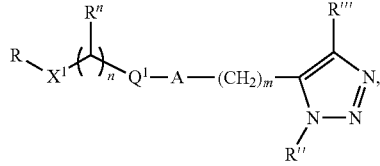
(XV)

the method including contacting a compound having the following structure,

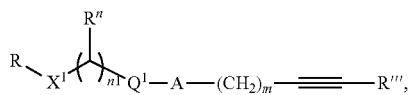
(XVI)

where
m is an integer between 0-20;
A is optionally substituted aryl, optionally substituted heteroaryl, or a substructure according to the formula —Ar$^{Z1}$—Z—Ar$^{Z2}$—, where
each of Ar$^{Z1}$ and Ar$^{Z2}$ is, independently, optionally substituted aryl or optionally substituted heteroaryl, and
Z is a covalent bond, O, S, NR$^{Z1}$, where R$^{Z1}$ is H or optionally substituted C1-6 alkyl, an optionally substituted C1-20 alkylene, a polyethylene glycol of the structure (CH$_2$CH$_2$O)(CH$_2$CH$_2$O)$_n$(CH$_2$CH$_2$), where n is an integer between 0-1000, or a linking group having the structure X$^{Z1}$-(Q$^{Z1}$)$_{n3}$-R$^{Z2}$-(Q$^{Z1}$)$_{n4}$X$^{Z1}$, where
each of n3 and n4 is, independently, 0 or 1,
each X$^{Z1}$ is, independently, a covalent bond, O, S, or NR$^{Z1}$,
each Q$^{Z1}$ is, independently, C(=O), S(=O), or S(=O)$_2$, and
R$^{Z2}$ is optionally substituted C1-20 alkylene or (CH$_2$CH$_2$O)(CH$_2$CH$_2$O)$_n$(CH$_2$CH$_2$), where n is an integer between 0-1000;
Q$^1$ is C(=O), S(=O)$_2$, or optionally substituted C1 alkylene;
n1 is 0 or 1;
X$^1$ is O, S, or NR$^X$, where R$^X$ is H or optionally substituted C1-6 alkyl;
each R" is, independently, H or optionally substituted C1-6 alkyl;
R is a protein or a biologically active or biologically compatible agent; and
R'" is H, optionally substituted C1-20 alkyl, a protein, or a biologically active or biologically compatible agent,
with
a compound having the structure R'"—N$_3$, where R'" is a protein or a biologically active or biologically compatible agent.

In some embodiments, R'" is H.

In some embodiments, R'" is a protein, a biologically active agent, or a biologically compatible agent.

In some embodiments, A is optionally substituted phenyl, optionally substituted naphthyl, optionally substituted furyl, or optionally substituted thienyl. In further embodiments, A is ortho-phenyl, meta-phenyl, or para-phenyl.

In other embodiments, A is a substructure according to the formula —Ar$^{Z1}$—Z—Ar$^{Z2}$—. In still other embodiments, Ar$^{Z1}$ and A$^{Z2}$ are both phenyl, and Z is a covalent bond, O, optionally substituted C1-20 alkylene, or —(CH$_2$CH$_2$O)(CH$_2$CH$_2$O)$_n$(CH$_2$CH$_2$)—, where n is an integer between 0-1000.

In some embodiments, at least one of R and R" is a protein. In some embodiments, both R and R" are proteins. In further embodiments, the protein is an annexin protein, an antibody, a cytokine, a wild-type protein that includes a free cysteine residue, or a protein modified to include a free cysteine residue.

In some embodiments, at least one of R and R" is a polymer, nucleic acid, carbohydrate, small molecule therapeutic agent, imaging agent, or diagnostic agent (e.g., a radionucleotide, a small molecule therapeutic agent, an optical label, a fluorescent label, a biosynthetic label, or an oligonucleotide). In some embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features a method for preparing a conjugate having a structure according to a formula selected from,

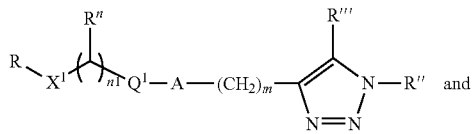 (XIV)

and

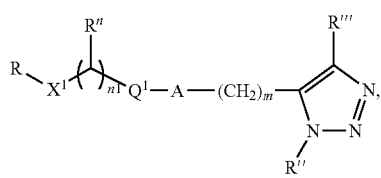 (XV)

the method including
(i) contacting a compound having the following structure,

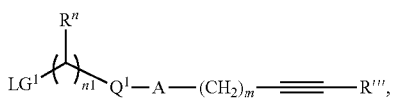 (XVI)

where
LG$^1$ is F, Cl, Br, or I,
m is an integer between 0-20;
A is optionally substituted aryl, optionally substituted heteroaryl, or a substructure according to the formula —Ar$^{Z1}$—Z—Ar$^{Z2}$—, where
  each of Ar$^{Z1}$ and Ar$^{Z2}$ is, independently, optionally substituted aryl or optionally substituted heteroaryl, and
  Z is a covalent bond, O, S, NR$^{Z1}$, where R$^{Z1}$ is H or optionally substituted C1-6 alkyl, an optionally substituted C1-20 alkylene, a polyethylene glycol of the structure $(CH_2CH_2O)(CH_2CH_2O)_n(CH_2CH_2)$, where n is an integer between 0-1000, or a linking group having the structure —X$^{Z1}$-(Q$^{Z1}$)$_{n3}$-R$^{Z2}$-(Q$^{Z1}$)$_{n4}$X$^{Z1}$, where
    each of n3 and n4 is, independently, 0 or 1,
    each X$^{Z1}$ is, independently, a covalent bond, O, S, or NR$^{Z1}$,
    each Q$^{Z1}$ is, independently, C(=O), S(=O), or S(=O)$_2$, and
    R$^{Z2}$ is optionally substituted C1-20 alkylene or $(CH_2CH_2O)(CH_2CH_2O)_n(CH_2CH_2)$, where n is an integer between 0-1000;
Q$^1$ is C(=O), S(=O)$_2$, or optionally substituted C1 alkylene;
n1 is 0 or 1;
X$^1$ is O, S, or NR$^X$, where R$^X$ is H or optionally substituted C1-6 alkyl;
each R$''$ is, independently, H or optionally substituted C1-6 alkyl; and
R$'''$ is H, optionally substituted C1-20 alkyl, a protein, or a biologically active or biologically compatible agent
with
a compound having the structure R''—N$_3$, where R'' is a protein or a biologically active or biologically compatible agent; and (ii) treating the product of step (i), where the product has a structure according to the following formula,

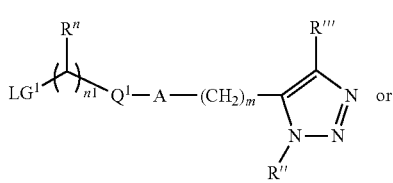 (XVII) or

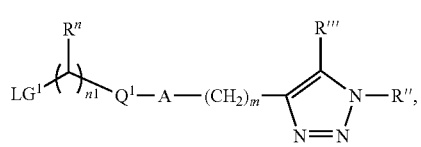 (XVIII)

with a compound having the structure R—X$^1$H, where R is a protein or a biologically active or biologically compatible agent, and X$^1$ is O, S, or NR$^X$, where R$^X$ is H or optionally substituted C1-6 alkyl.

In some embodiments, R''' is H.

In some embodiments, R''' is a protein, a biologically active agent, or a biologically compatible agent.

In some embodiments, A is optionally substituted phenyl, optionally substituted naphthyl, optionally substituted furyl, or optionally substituted thienyl. In further embodiments, A is ortho-phenyl, meta-phenyl, or para-phenyl.

In other embodiments, A is a substructure according to the formula —Ar$^{Z1}$—Z—Ar$^{Z2}$—. In still other embodiments, Ar$^{Z1}$ and A$^{Z2}$ are both phenyl, and Z is a covalent bond, O, optionally substituted C1-20 alkylene, or —(CH$_2$CH$_2$O)(CH$_2$CH$_2$O)$_n$(CH$_2$CH$_2$)—, where n is an integer between 0-1000.

In some embodiments, at least one of R and R'' is a protein. In some embodiments, both R and R'' are proteins. In further embodiments, the protein is an annexin protein, an antibody, a cytokine, a wild-type protein that includes a free cysteine residue, or a protein modified to include a free cysteine residue.

In some embodiments, at least one of R and R'' is a polymer, nucleic acid, carbohydrate, small molecule therapeutic agent, imaging agent, or diagnostic agent (e.g., a radionucleotide, a small molecule therapeutic agent, an optical label, a fluorescent label, a biosynthetic label, or an oligonucleotide). In some embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R'' is an annexin protein, and the other is an antibody, a cytokine, a biologically active agent, or a biologically compatible agent.

In a further aspect, the invention features a method of preparing a conjugate including
(a) contacting
  (i) a nucleophile-containing macromolecule R—X$^1$H, where R is a protein or a biologically active or biologically compatible agent, and X$^1$ is S, O, or NR$^X$, where R$^X$ is H or optionally substituted C1-6 alkyl;

with
(ii) a quinone compound according to the following formula,

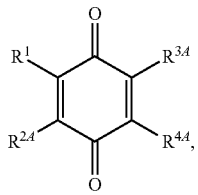

(XIX-A)

where
each of $R^{2A}$, $R^{3A}$, and $R^{4A}$ is selected, independently, from H, F, Cl, Br, I, $SR^5$, $R^6$, and $OR^7$; and
each of $R^5$, $R^6$, and $R^7$ is, independently H, optionally substituted C1-C6 alkyl, optionally substituted C1-C6 alkaryl, or optionally substituted C6-C10 aryl; and
where at least two of $R^1$, $R^{2A}$, $R^{3A}$, and $R^{4A}$ are H;
to form a conjugate including a covalent bond between the X' group and a carbon of the quinone compound; and
(b) contacting said conjugate of step (a) with a nucleophile-containing macromolecule having the structure $R''X^2H$, where R" is a protein, a biologically active, or a biologically compatible agent; and $X^2$ is S, O, or $NR^X$ where $R^X$ is H or optionally substituted C1-6 alkyl,
and where the product conjugate includes a covalent bond that forms between $X^2$ and a carbon of the quinone moiety.

In another aspect, the invention features a method that includes
(a) contacting
(i) a nucleophile-containing macromolecule $R—X^1H$, where R is a protein or a biologically active or biologically compatible agent, and $X^1$ is S, O, or $NR^X$, wherein $R^X$ is H or optionally substituted C1-6 alkyl;
with
(ii) a quinone compound according to the following formula,

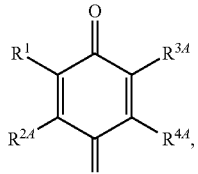

(XIX-A)

where
each of $R^1$, $R^{2A}$, $R^{3A}$, and $R^{4A}$ is selected, independently, from H, F, Cl, Br, I, $SR^5$, $R^6$, and $OR^7$; and
each of $R^5$, $R^6$, and $R^7$ is, independently H, optionally substituted C1-C6 alkyl, optionally substituted C1-C6 alkaryl, or optionally substituted C6-C10 aryl;
to form a conjugate that includes a covalent bond between said $X^1$ group and a carbon of said quinone compound; and (b) optionally contacting the conjugate of step (a) with a bifunctional compound according to the formula, HY-L-YH, where each Y is, independently, a covalent bond, S, NH, or O, and L is a linker group selected from C1-C20 alkylene;
$(CH_3CH_2O)(CH_2CH_2O)_n(CH_2CH_3)$, wherein n is an integer between 0-1000;
a peptide having between 2-25 amino acid residues; or
a peptoid having between 2-25 residues;
where a covalent bond forms between a Y group of said bifunctional compound and a carbon of said conjugate; and
optionally subjecting a composition that includes the product of step (a) and/or step (b) to oxidizing conditions.

In some embodiments, the method includes subjecting a composition that includes the conjugate to oxidizing conditions.

In some embodiments, $R^{2A}$, $R^{3A}$, and $R^{4A}$ are H.

In other embodiments, one or two of $R^1$, $R^{2A}$, $R^{3A}$, and $R^{4A}$ are optionally substituted C1-C6 alkyl.

In some embodiments, one or two of $R^1$, $R^{2A}$, $R^{3A}$, and $R^{4A}$ is F, Cl, Br, or I.

In other embodiments, the nucleophile-containing macromolecule is R—SH.

In some embodiments, the nucleophile-containing macromolecule is contacted with a quinone compound of Formula (XIX-A) to form the following conjugate,

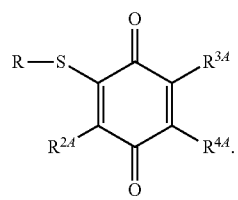

(XX-A)

In further embodiments, the conjugate has the following structure,

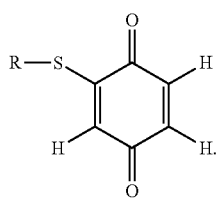

(XX-B)

In some embodiments, $R^{2A}$ and $R^{3A}$, or $R^{2A}$ and $R^{4A}$, or $R^{3A}$ and $R^{4A}$ are both optionally substituted C1-C6 alkyl.

In certain embodiments, the method also includes contacting the conjugate with a nucleophile-containing macromolecule having the structure $R''X^2H$, where R" is a protein or a biologically active or biologically compatible agent; and $X^2$ is S, O, or NH, and where the product conjugate includes a covalent bond that forms between $X^2$ and a carbon of the quinone moiety.

In some embodiments, the method includes further subjecting a composition that includes the product conjugate to oxidizing conditions.

In certain embodiments, the product conjugate has a structure according to one of the following formulas,

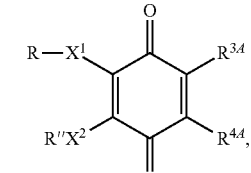
(XXI-A)

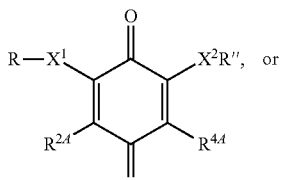
(XXI-B)

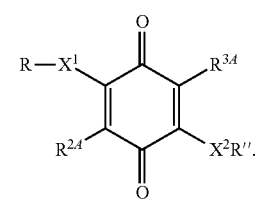
(XXI-C)

In some embodiments, $R^{2A}$ and $R^{3A}$ are both H or optionally substituted C1-C6 alkyl in Formula (XXI-A);

$R^{2A}$ and $R^{4A}$ are both H or optionally substituted C1-C6 alkyl in Formula (XXI-B); or $R^{3A}$ and $R^{4A}$ are both H or optionally substituted C1-C6 alkyl in Formula (XXI-C).

In some embodiments, $X^1$ is S.

In other embodiments, $X^2$ is S.

In certain embodiments, one or both of R and R″ is a protein (e.g., a protein that is an annexin protein, an antibody, a cytokine, a wild-type protein that includes a free cysteine residue, or a protein modified to include a free cysteine residue).

In other embodiments, one or both of R and R″ is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R″ is an annexin protein, and the other is an antibody, a cytokine, a biologically active agent, or a biologically compatible agent.

In another aspect, the invention features a method for preparing a conjugate having the following formula,

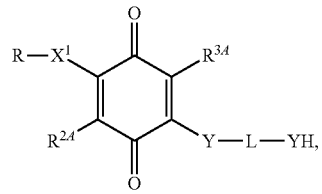
(XXII)

or a linkage isomer thereof, the method including (a) contacting (i) a compound according to Formula (XX-C),

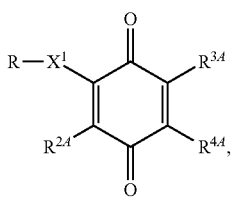
(XX-C)

where R is a protein or a biologically active or biologically compatible agent, $X^1$ is S, O, or NH, and each of $R^{2A}$, $R^{3A}$, and $R^{4A}$ is H or optionally substituted C1-C6 alkyl, where at least one of $R^{2A}$, $R^{3A}$, and $R^{4A}$ is H;

with (ii) a bifunctional compound according to the following formula, HY-L-YH, where each Y is, independently, a covalent bond, S, NH, or O, and L is a linker group selected from C1-C20 alkylene;

$(CH_3CH_2O)(CH_2CH_2O)_n(CH_2CH_3)$, where n is an integer between 0-1000;

a peptide having between 2-25 amino acid residues; or a peptoid having between 2-25 residues;

where a covalent bond forms between a Y group of the bifunctional compound and a carbon of the quinone ring;

and (b) optionally subjecting a composition including the product of (a) to oxidizing conditions.

In some embodiments, the product conjugate is

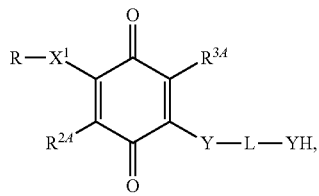
(XXII-A)

where $R^{2A}$ an are, independently, H and $R^{3A}$ or optionally substituted C1-C6 alkyl.

In other embodiments, the product conjugate is

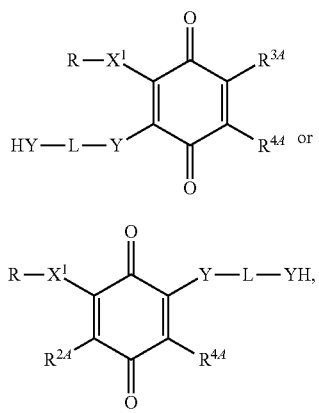

(XXII-B)

(XXII-C)

where $R^{2A}$ and $R^{3A}$ are, independently, H or optionally substituted C1-C6 alkyl.

In some embodiments, $X^1$ is S.

In other embodiments, one or both Y groups is S.

In certain embodiments, R is a protein (e.g., a protein that is an annexin protein, an antibody, a cytokine, a wild-type protein that includes a free cysteine residue, or a protein modified to include a free cysteine residue).

In other embodiments, R is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, R is an annexin protein, and the other is an antibody, a cytokine, a biologically active agent, or a biologically compatible agent.

In a further aspect, the invention features a method of crosslinking two benzoquinone conjugates that includes
(a) contacting a first benzoquinone conjugate (e.g., any of the conjugates described herein) with
(b) a bifunctional compound according to the following formula,
HY-L-YH, wherein each Y is, independently, a covalent bond, S, NH, or O, and L is a linker group selected from
C1-C20 alkylene;
$(CH_3CH_2O)(CH_2CH_2O)_n(CH_2CH_3)$, wherein n is an integer between 0-1000;
a peptide having between 2-25 amino acid residues; and
a peptoid having between 2-25 residues;
where a covalent bond forms between a Y group of said bifunctional compound and a carbon of said conjugate producing a Y-L-YH tethered ring;
and
(c) treating the adduct formed by (a) and (b) with a second benzoquinone conjugate to tether the two quinone rings In another aspect, the invention features a method of synthesizing a conjugate according to the following formula,

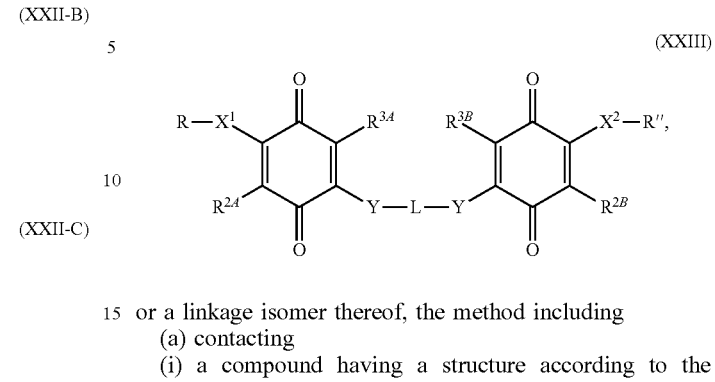

(XXIII)

or a linkage isomer thereof, the method including
(a) contacting
(i) a compound having a structure according to the following formula,

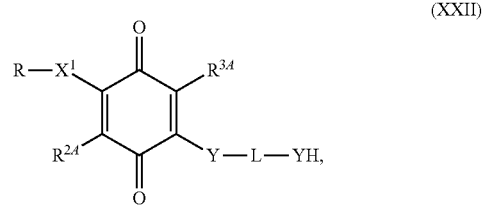

(XXII)

or an isomer thereof, where
R is a protein or a biologically active or biologically compatible agent;
$X^1$ is S, O, or NH
$R^{2A}$ and $R^{3A}$ are, independently, H, F, Cl, Br, I, or optionally substituted C1-C6 alkyl;
each Y is, independently, a covalent bond, O, S, or NH; and
L is a linker group selected from C1-C20 alkylene; $(CH_3CH_2O)(CH_2CH_2O)_n(CH_2CH_3)$, where n is an integer between 0-1000; a peptide having between 2-25 amino acid residues; or a peptoid having between 2-25 residues;
with
(ii) a compound according to the following formula,

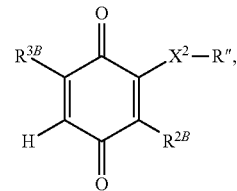

or an isomer thereof, where
$X^2$ is S, O, or NH
$R^{2B}$ and $R^{3B}$ are, independently, H, F, Cl, Br, I, or optionally substituted C1-C6 alkyl;
each Y is O, S, or NH; and
R" is a protein or a biologically active or biologically compatible agent; and
optionally
(b) subjecting a composition including the product of (a) to oxidizing conditions.
In some embodiments, $X^1$ is S.
In other embodiments, $X^2$ is S.

In still other embodiments, one or both Y groups are S or where one or both Y groups are a covalent bond.

In some embodiments, L is C1-C20 alkylene.

In certain embodiments, $R^{2A}$ and $R^{3A}$ are both H or both optionally substituted C1-C6 alkyl.

In still other embodiments, $R^{2B}$ and $R^{3B}$ are both H or both optionally substituted C1-C6 alkyl.

In certain embodiments, one or both of R and R" is a protein (e.g., a protein that is an annexin protein, an antibody, a cytokine, a wild-type protein that includes a free cysteine residue, or a protein modified to include a free cysteine residue).

In other embodiments, one or both of R and R" is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb 212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features a method of synthesizing a conjugate according to the following formula, (XXIII)

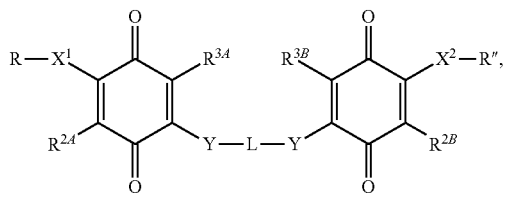

or a linkage isomer thereof, the method including
(a) contacting
(i) a compound according to the following formula, (XXIV)

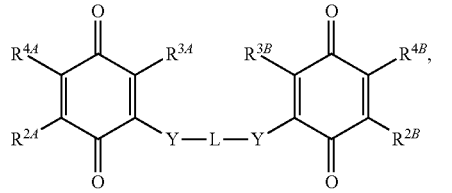

or a linkage isomer thereof,
where
each Y is a covalent bond, O, S, or NH;
each of $R^{2A}$, $R^{3A}$, $R^{2B}$, and $R^{3B}$ is, independently, H or optionally substituted C1-C6 alkyl;
each of $R^{4A}$ and $R^{4B}$ is, independently, H, F, Cl, Br, I, or SR''', wherein R''' is H, optionally substituted C1-6 alkyl, a protein, a biologically active agent, or a biologically compatible agent;
L is a linker group selected from C1-C20 alkylene; $(CH_3CH_2O)(CH_2CH_2O)_n(CH_2CH_3)$, where n is an integer between 0-1000; a peptide having between 2-25 amino acid residues; or a peptoid having between 2-25 residues;
with
(ii) a compound $R-X^1H$, where R is a protein, a biologically active agent, or a biologically compatible agent, and $X^1$ is O, NH, or S;
(b) optionally subjecting a composition including the product of step (a) to oxidizing conditions,
(c) contacting the conjugate obtained from step (a) or from the sequence of steps (a) and (b) with a compound $R''-X^2H$, where R" is a protein, a biologically active agent, or a biologically compatible agent, and $X^2$ is O, NH, or S; and
(d) optionally subjecting a composition including the product of step (c) to oxidizing conditions.

In some embodiments, $X^1$ is S.

In other embodiments, $X^2$ is S.

In still other embodiments, one or both Y groups are S or where one or both Y groups are a covalent bond.

In some embodiments, L is C1-C20 alkylene.

In certain embodiments, $R^{2A}$ and $R^{3A}$ are both H or both optionally substituted C1-C6 alkyl.

In still other embodiments, $R^{2B}$ and $R^{3B}$ are both H or both optionally substituted C1-C6 alkyl.

In certain embodiments, one or both of R and R" is a protein (e.g., a protein that is an annexin protein, an antibody, a cytokine, a wild-type protein that includes a free cysteine residue, or a protein modified to include a free cysteine residue).

In other embodiments, one or both of R and R" is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In still another aspect, the invention features a method of synthesizing a conjugate according to the following formula, (XXV)

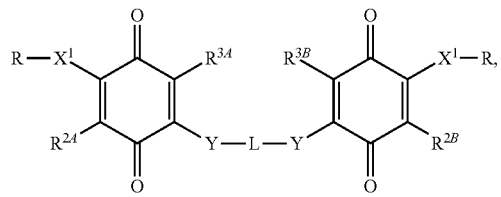

or a linkage isomer thereof, the method including
(a) contacting a compound according to the following formula,

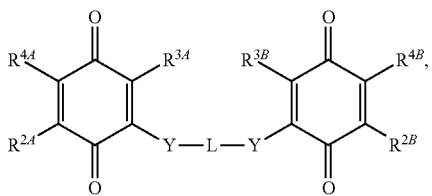

(XXIV)

or a linkage isomer thereof,
where
each Y is a covalent bond, O, S, or NH;
each of $R^{2A}$, $R^{3A}$, $R^{2B}$, and $R^{3B}$ is, independently, H or optionally substituted C1-C6 alkyl;
each of $R^{4A}$ and $R^{4B}$ is, independently, H, F, Cl, Br, I, or SR''', wherein R''' is H, optionally substituted C1-6 alkyl, a protein, a biologically active agent, or a biologically compatible agent;
L is a linker group selected from C1-C20 alkylene; $(CH_3CH_2O)(CH_2CH_2O)_n(CH_2CH_3)$, where n is an integer between 0-1000; a peptide having between 2-25 amino acid residues; or a peptoid having between 2-25 residues;
with a compound R—$X^1$H, wherein R is a protein, a biologically active agent, or a biologically compatible agent, and $X^1$ is O, NH, or S; and
(b) optionally subjecting the product thereby obtained to oxidizing conditions.

In some embodiments, $X^1$ is S.
In other embodiments, $X^2$ is S.
In still other embodiments, each of $R^{4A}$ and $R^{4B}$ is H.
In still other embodiments, one or both Y groups are S or where one or both Y groups are a covalent bond.
In some embodiments, L is C1-C20 alkylene.
In certain embodiments, $R^{2A}$ and $R^{3A}$ are both H or both optionally substituted C1-C6 alkyl.
In still other embodiments, $R^{2B}$ and $R^{3B}$ are both H or both optionally substituted C1-C6 alkyl.
In certain embodiments, one or both of R and R'' is a protein (e.g., a protein that is an annexin protein, an antibody, a cytokine, a wild-type protein that includes a free cysteine residue, or a protein modified to include a free cysteine residue).
In other embodiments, one or both of R and R'' is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.
In certain embodiments, one of R and R'' is an annexin protein, and the other is an antibody, a cytokine, a biologically active agent, or a biologically compatible agent.
In still another aspect, the invention features a method of synthesizing a conjugate including contacting (a) R—SH, where R is a protein or a biologically active or biologically compatible agent and —SH represents a free thiol group,
with
(b) a quinone compound selected from

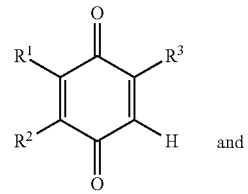

(XXVI-A)

and

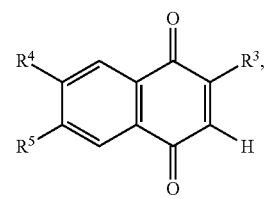

(XXVI-B)

where
each of R', $R^2$, $R^4$, and $R^5$ is selected, independently, from H, optionally substituted C1-C6 alkyl, optionally substituted C6-C10 aryl, —$X(CH_2)_nC(\!=\!O)R'$, —$X(CH_2)_nSO_2R'$, where n is an integer between 0-4, R' is a protein or biologically active or biologically compatible agent, and X is absent, S, O, or NR'', where R'' is H, optionally C1-C6 alkyl, optionally substituted C6-C10 aryl, or optionally substituted arylsulfonyl; and
$R^3$ is H, F, Cl, I, SR'', or OR'', where R'' is H, optionally C1-C6 alkyl, optionally substituted C6-C10 aryl, or optionally substituted arylsulfonyl.

In certain embodiments, one or both of R and R'' is a protein (e.g., a protein that is an annexin protein, an antibody, a cytokine, a wild-type protein that includes a free cysteine residue, or a protein modified to include a free cysteine residue).
In other embodiments, one or both of R and R'' is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.
In certain embodiments, one of R and R'' is an annexin protein, and the other is an antibody, a cytokine, a biologically active agent, or a biologically compatible agent.
In some embodiments, the method further includes treating the conjugate with a compound that includes polyethylene glycol (e.g., PEG-thiol) or a polysialic acid (e.g., polysialic acid thiol).

In certain embodiments, the method further includes subjecting the conjugate to oxidizing conditions.

In another aspect, the invention features a method of preparing a conjugate, the method including a cycloaddition reaction between (a) a quinone compound having a structure according to one of the following structures,

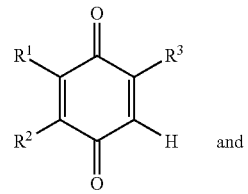

(XXVI-A)

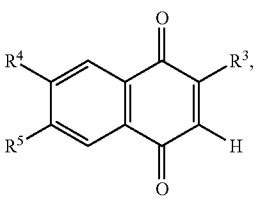

(XXVI-B)

where each of $R^1$, $R^2$, $R^4$, and $R^5$ is selected, independently, from H, optionally substituted C1-C6 alkyl, optionally substituted C6-C10 aryl, —X(CH$_2$)$_n$C(=O)R', —X(CH$_2$)$_n$SO$_2$R', where n is an integer between 0-4, R' is a protein or biologically active or biologically compatible agent, and X is absent, S, O, or NR", where R" is H, optionally C1-C6 alkyl, optionally substituted C6-C10 aryl, or optionally substituted arylsulfonyl; and $R^3$ is H, F, Cl, I, SR", or OR", where R" is H, optionally C1-C6 alkyl, optionally substituted C6-C10 aryl, or optionally substituted arylsulfonyl;

and (b) a diene compound selected from optionally substituted butadiene, optionally substituted cyclopentadiene, optionally substituted furyl, or optionally substituted cyclohexadienyl, where the diene compound is optionally substituted with 1, 2, 3, or 4 groups selected from optionally substituted C1-C6 alkyl, optionally substituted C6-C10 aryl, —X(CH$_2$)$_n$(C(=O))$_m$R', —X(CH$_2$)$_n$(SO$_2$)$_m$R', wherein n is an integer between 0-4, m is 0 or 1, R' is a protein, a biologically active agent, or a biologically compatible agent, and X is a covalent bond, S, O, or NR", wherein R" is H, optionally C1-C6 alkyl, optionally substituted C6-C10 aryl, or optionally substituted arylsulfonyl.

In another aspect, the invention features a conjugate prepared according to any of synthetic methods described herein.

In still another aspect, the invention features a composition that includes a conjugate prepared according to any of the methods described herein. In some embodiments, the composition is a pharmaceutical composition.

In another aspect, the invention features a conjugate having a structure according to the following formula,

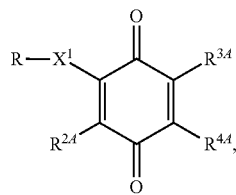

where each of $X^1$ and $X^2$ is, independently, S, O, or NH;

each of R and R" is, independently, a protein or biologically active or biologically compatible agent;

each of $R^{2A}$, $R^{3A}$, and $R^{4A}$ is selected, independently, from H, F, Cl, Br, SR$^5$, R$^6$, OR$^7$, and —X$^2$R", and each of $R^5$, $R^6$, and $R^7$ is, independently, H, optionally substituted C1-C6 alkyl, optionally substituted C1-C6 alkaryl, or optionally substituted C6-C10 aryl; and where at least two of $R^{2A}$, $R^{3A}$, and $R^{4A}$ are H, and where one and only one of $R^{2A}$, $R^{3A}$, and $R^{4A}$ can be X$^2$R".

In some embodiments, the conjugate has a structure according to one of the following formulas,

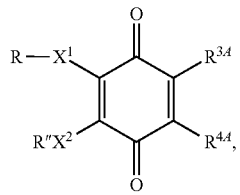

(XXI-A)

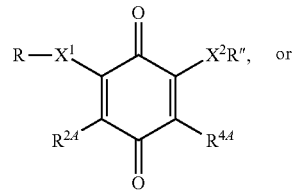

(XXI-B)

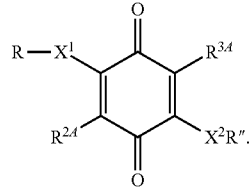

(XXI-C)

In certain embodiments, each of $R^{2A}$, $R^{3A}$, $R^{4A}$ is, independently, H or optionally C1-C6 alkyl.

In other embodiments, the conjugate has a structure according to one of the following formulas,

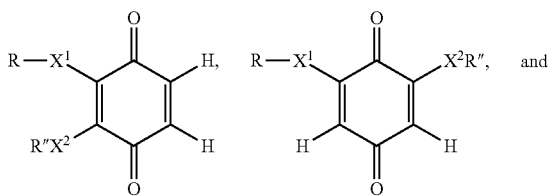

-continued

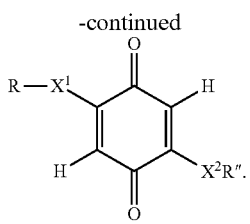

In certain embodiments, $X^2$ is S.

In some embodiments, $X^1$ is S.

In other embodiments, at least one of R and R" is a protein (e.g., a protein that is an annexin protein, an antibody, a cytokine, a wild-type protein that includes a free cysteine residue, or a protein modified to include a free cysteine residue).

In other embodiments, one or both of R and R" is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In another aspect, the invention features a conjugate according to the following formula,

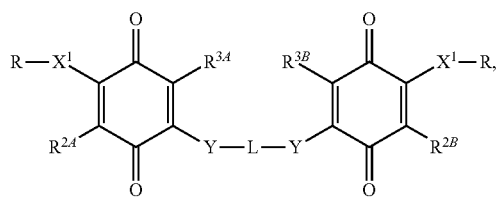

(XXIII)

or a linkage isomer thereof,
where
each of $X^1$ and $X^2$ is, independently, S, O, or NH;
each of R and R" is, independently, is a protein or a biologically active or biologically compatible agent;
each Y is, independently, a covalent bond, O, S, or NH; and
L is a linker group selected from C1-C20 alkylene; $(CH_3CH_2O)(CH_2CH_2O)_n(CH_2CH_3)$, where n is an integer between 0-1000; a peptide having between 2-25 amino acid residues; or a peptoid having between 2-25 residues.

In some embodiments, each Y group is a covalent bond.
In other embodiments, L is a C1-C20 alkylene.
In some embodiments, $X^1$ is S.
In still other embodiments, $X^2$ is S.
In other embodiments, at least one of R and R" is a protein (e.g., a protein that is an annexin protein, an antibody, a cytokine, a wild-type protein that includes a free cysteine residue, or a protein modified to include a free cysteine residue).

In other embodiments, one or both of R and R" is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In still another embodiment, the invention features a conjugate according to the following formula,

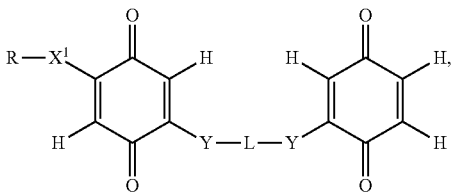

where
$X^1$ is S, O, or NH;
R is a protein or a biologically active or biologically compatible agent;
each Y is, independently, a covalent bond, O, S, or NH; and
L is a linker group selected from C1-C20 alkylene; $(CH_3CH_2O)(CH_2CH_2O)_n(CH_2CH_3)$, where n is an integer between 0-1000; a peptide having between 2-25 amino acid residues; or a peptoid having between 2-25 residues.

In some embodiments, $X^1$ is S.
In other embodiments, each Y group is a covalent bond.
In certain embodiments, L is a C1-C20 alkylene.
In still other embodiments, R is protein (e.g., an antibody or a protein modified to include a free cysteine residue).

In other embodiments, at least one of R and R" is a protein (e.g., a protein that is an annexin protein, an antibody, a cytokine, a wild-type protein that includes a free cysteine residue, or a protein modified to include a free cysteine residue).

In other embodiments, one or both of R and R" is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In still another aspect, the invention features a conjugate having a structure according to one of the following formulas,

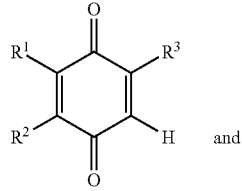

(XXVI-A)

and

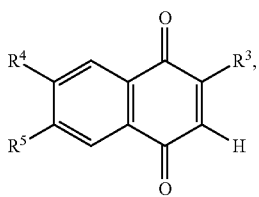

(XXVI-B)

where
each of R', R², R⁴, and R⁵ is selected, independently, from
H,
optionally substituted C1-C6 alkyl,
optionally substituted C6-C10 aryl,
—X(CH₂)$_n$C(=O)R' or —X(CH₂)$_n$SO₂R', where n is an integer between 0-4, R' is a protein or biologically active or biologically compatible agent, and X is absent, S, O, or NR", where R" is H, optionally C1-C6 alkyl, optionally substituted C6-C10 aryl, or optionally substituted arylsulfonyl, and
X¹R, where X¹ is S, O, or NH and R is a protein or biologically active or biologically compatible agent; and
R³ is H, F, Cl, I, SR", or OR", where R" is H, optionally C1-C6 alkyl, optionally substituted C6-C10 aryl, or optionally substituted arylsulfonyl, and
where one and only one of R¹, R², R⁴, and R⁵ can be X¹R.
In some embodiments, X¹ is S.
In other embodiments, X is S.
In other embodiments, at least one of R and R" is a protein (e.g., a protein that is an annexin protein, an antibody, a cytokine, a wild-type protein that includes a free cysteine residue, or a protein modified to include a free cysteine residue).

In other embodiments, one or both of R and R" is a biologically active agent or a biologically compatible agent (e.g, a polymer, nucleic acid, carbohydrate (e.g., a monosaccharide, a disaccharide, an oligosaccharide, or a polysaccharide), small molecule therapeutic agent, imaging agent, or diagnostic agent). In further, embodiments, the polymer includes polyethylene glycol, the carbohydrate is polysialic acid, or the diagnostic agent is selected from a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red, phycobiliproteins, [18F]-labeled benzaldehyde, [18F]-labeled fluoro-2-deoxyglucose (FDG), tetracetyl fluoroglucose (TAFg), or a fluorescence energy transfer (FRET) donor or acceptor.

In certain embodiments, one of R and R" is an annexin protein, and the other is an antibody, a cytokine, a biologically active agent, or a biologically compatible agent.

In still another aspect, the invention features a conjugate having a structure according to the following formula,

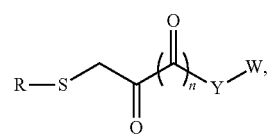

(XXVII)

where
R is a protein, a biologically active agent, or a biologically compatible agent;
Y is a covalent bond, O, or NR$^Y$, where R$^Y$ is H, optionally substituted C1-6 alkyl or optionally substituted aryl;
n is 0 or 1; and
W is optionally substituted alkyl or aryl.

In certain embodiments, the conjugate has the following structure,

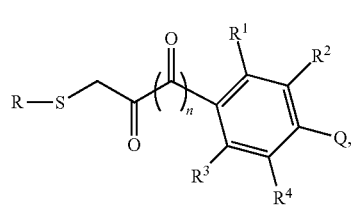

(XXVIII)

or an isomer thereof, where R¹, R², R³, and R⁴ are selected, independently, from H, halogen, optionally substituted C1-6 alkyl, or optionally substituted aryl, Q is COR⁵, SO₂NR⁶R⁷, or OR⁶; and each of R⁵, R⁶, and R⁷ is, independently, H, optionally substituted alkyl or optionally substituted aryl, where Q includes a covalent bond to a protein, a biologically active agent, or a biologically compatible agent.

In other embodiments, W includes a protein, a biologically active agent, or a biologically compatible agent.

In certain embodiments, n is 1
In other embodiments, n is 0.
In still other embodiments, R is selected from the group consisting of annexin proteins, α-1-antiprotease, human sonic hedgehog N-terminal protein, oncostatin M, primary ribosomal protein S4, a wild-type protein that includes a free thiol group, a protein modified to include a free thiol group, an antibody, a minibody, a diabody, and an affybody.

In a further aspect, the invention features a conjugate having a structure according to the following formula,

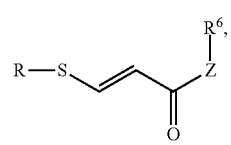

(XXIX)

where
R is a protein, a biologically active agent, or a biologically compatible agent;
Z is O or NR⁷; and
each of R⁶ and R⁷ is, independently, H, optionally substituted C1-6 alkyl, and where one of R⁶ and R⁷ includes a covalent bond to protein, a biologically active agent, or a biologically compatible agent.

In further embodiments, R is selected from the group consisting of annexin proteins, α-1-antiprotease, human sonic hedgehog N-terminal protein, oncostatin M, primary ribosomal protein S4, a wild-type protein that includes a free thiol group, a protein modified to include a free thiol group, an antibody, a minibody, a diabody, and an affybody.

In still another aspect, the invention features a conjugate having a structure according to the following formula,

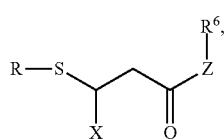

(XXX)

where

R is a protein, a biologically active agent, or a biologically compatible agent;

X is H, optionally substituted C1-6 alkyl, or optionally substituted aryl;

Z is O or $NR^7$; and each of $R^6$ and $R^7$ is, independently, H, optionally substituted C1-6 alkyl, and where one of $R^6$ and $R^7$ includes a covalent bond to protein, a biologically active agent, or a biologically compatible agent.

In some embodiments, R is selected from the group consisting of annexin proteins, α-1-antiprotease, human sonic hedgehog N-terminal protein, oncostatin M, primary ribosomal protein S4, a wild-type protein that includes a free thiol group, a protein modified to include a free thiol group, an antibody, a minibody, a diabody, and an affybody.

In any of the synthetic methods described herein, the method can further include treating the product conjugate with a compound that includes polyethylene glycol (e.g., PEG-thiol) or a polysialic acid (e.g., polysialic acid thiol).

Where a conjugate includes a quinone (e.g, a 1,4-benzoquinone) moiety, the invention also encompasses the related dihydroquinone analogue (see, e.g., compounds of Formula (I) in Scheme 13) and the corresponding aromatized diphenol compound (see, e.g., compounds of Formula (II) in Scheme 13).

Any of the conjugates herein can also feature more than one covalent bond (e.g., two, three, or four covalent bonds) between a protein, a biologically active agent, or a biologically active agent (see, e.g., Schemes 14 and 15).

Conjugates that are prepared from, e.g., α-halocarbonyl moieties, and which include one or more additional nucleophilic groups can also form tetrahedral adducts by nucleophilic addition to the carbonyl group (see, e.g., Scheme 14). Such conjugates are also encompassed by the present invention.

The invention also encompasses linkage isomers of the exemplary conjugates shown herein that include, e.g., a phenyl group, a naphthyl group, a group according to substructure A, or a quinone group. Linkage isomers are illustrated by, e.g., the compounds of Formulas (II-A), (II-B), and (II-C), which are ortho-, meta-, and para-substituted isomers. As a further example, addition of two different nucleophilic groups, $Nuc^1$ and $Nuc^2$ (which may be on separate molecular entities or may be found on the same molecular entity) to 1,4-benzoquinone can produce linkage isomers according to any of Formulas (XXXI-A), (XXXI-B), and (XXX-C):

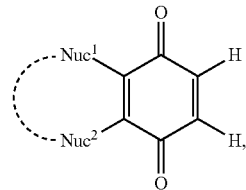

(XXXI-A)

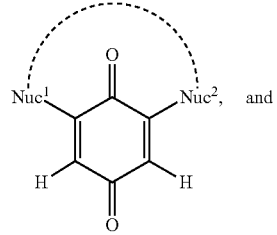

(XXXI-B)

and

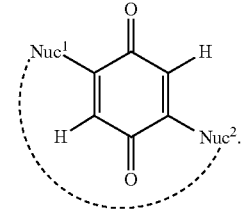

(XXXI-C)

In another aspect, the invention features a conjugate prepared according to any of the synthetic methods described herein.

In still another aspect, the invention features a composition that includes any of the conjugates described herein or any conjugate prepared according to any of the synthetic methods described herein.

In another aspect, the invention features a pharmaceutical composition that includes any of the conjugates described herein or any conjugate prepared according to any of the synthetic methods described herein.

In still another aspect, the invention features a pharmaceutical composition that includes a conjugate prepared according to any of methods described herein, or any of the conjugates described herein, and a pharmaceutically acceptable excipient.

In another aspect, the invention features a method of delivering a therapeutic agent to a cell undergoing necrosis or apoptosis, the method including contacting said cell with an agent that is any of the conjugates described herein, or any conjugate prepared according to any of the synthetic methods described herein, or a protein conjugate that includes an annexin protein. In some embodiments, protein conjugates exclude fusion proteins where the portion that includes the annexin protein(s) is directly conjugated via a peptide bond to the portion containing the therapeutic agent (e.g., a protein) to be delivered. It is understood that the protein conjugates can include an annexin-containing protein that is conjugated to other fusion proteins for selective delivery of the fusion protein to a cell that is undergoing necrosis or apoptosis.

In a related aspect, the invention features a method of treating or preventing a disease or condition characterized by necrosis or apoptosis, the method including contacting said cell with an agent that is any of the conjugates described herein, or any conjugate prepared according to any of the synthetic methods described herein, or a protein conjugate that includes an annexin protein. In some embodiments, protein conjugates exclude fusion proteins where the portion that includes the annexin protein(s) is directly conjugated via a peptide bond to the portion containing the therapeutic agent (e.g., a protein) to be delivered. It is understood that the protein conjugates can include an annexin-containing protein that is conjugated to other fusion proteins for selective delivery of the fusion protein to a cell that is undergoing necrosis or apoptosis.

In another aspect, the invention features a method of delivering a therapeutic agent to a cell undergoing necrosis or apoptosis, where the method includes contacting a cell with an agent that is a protein conjugate that includes an annexin protein, and where the protein conjugate includes two or more proteins that are covalently tethered via a site-specific linking group (e.g., the linker site-specifically forms a covalent bond to protein thiol groups). In some embodiments, protein conjugates exclude fusion proteins where the portion that includes the annexin protein(s) is directly conjugated via a peptide bond to the portion containing the therapeutic agent (e.g., a protein) to be delivered. It is understood that the protein conjugates can include an annexin-containing protein that is conjugated to other fusion proteins for selective delivery of the fusion protein to a cell that is undergoing necrosis or apoptosis.

In still another aspect, the invention features a method of delivering a therapeutic agent to a cell undergoing necrosis or apoptosis, where the method includes contacting a cell with protein conjugate that includes an annexin protein, and where the protein conjugate is prepared using one or more site-specific linkers to form one or more covalent bonds (e.g., to protein thiol groups) between the proteins comprising said protein conjugate. In some embodiments, protein conjugates exclude fusion proteins where the portion that includes the annexin protein(s) is directly conjugated via a peptide bond to the portion containing the therapeutic agent (e.g., a protein) to be delivered. It is understood that the protein conjugates can include an annexin-containing protein that is conjugated to other fusion proteins for selective delivery of the fusion protein to a cell that is undergoing necrosis or apoptosis.

Exemplary annexin proteins that can be used in any of the methods and conjugates described herein are described in, e.g., Moss et al, "Annexins: from structure to function," *Physiol. Rev.* 82(2):331-71 (2002), which is hereby incorporated by reference. For example, wild-type annexin proteins, annexin proteins that have been modified to include a free thiol group, diannexin, fusion proteins that include one or more annexins, and multimeric forms of annexin can be used in the methods and conjugates described herein. In some embodiments, protein conjugates exclude fusion proteins where the portion that includes the annexin protein(s) is directly conjugated via a peptide bond to the portion containing the therapeutic agent (e.g., a protein) to be delivered. It is understood that the protein conjugates can include an annexin-containing protein that is conjugated to other fusion proteins for selective delivery of the fusion protein to a cell that is undergoing necrosis or apoptosis. In some embodiments, the annexin is or includes annexin I, III, IV, V (e.g., annexin V-128), VI, and/or VIII. In further embodiment, the annexin is or includes annexin 5. In some embodiments, the annexin may be further modified (e.g., to include a covalent attachment to another protein, a biologically active agent, or a biologically compatible agent) according to methods known in the art or according to any of the methods described herein.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "CX-CY-alkyl", wherein x is 1-5 and y is 2-10 indicates a particular alkyl group (straight- or branched-chain) of a particular range of carbons. For example, the expression C1-C6-alkyl includes, but is not limited to, methyl, ethyl, propyl, butyl, isopropyl, tert-butyl, isobutyl, n-pentyl, and n-hexyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems can be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "biologically compatible" refers to compounds that do not have biological activity and are non-toxic and non-inflammatory to, e.g., humans.

The term "cycloaddition" refers to a pericyclic chemical reaction, in which two or more unsaturated molecules (or parts of the same molecule) combine with the formation of a cyclic adduct in which there is a net reduction of the bond multiplicity.

The term "fusion protein" includes a single molecular entity having at least two polypeptide domains that are not normally present in a single, natural polypeptide, and where the polypeptide domains are linked by a polypeptide chain. Thus, naturally occurring proteins are not "fusion proteins", as used herein.

The term "heteroaryl," as used herein, represents an aromatic (i.e., containing 4n+2 pi electrons within the ring system) mono-, bi-, or tricyclic-membered ring having between 5-14 ring members and containing one, two, three, or four heteroatoms independently selected from the group consisting of nitrogen, oxygen, and sulfur. Exemplary heteroaryls include, but are not limited to, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl (e.g., 1,3,4-thiadiazole), isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl, tetrahydrofuranyl, dihydropyranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like.

The term "subject" is intended to include organisms, e.g., prokaryotes and eukaryotes, which are capable of suffering from or afflicted with a disease, disorder or condition. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, arthritis, atherothrombosis, plaque rupture, or Crohn's disease. In another embodiment, the subject is a cell.

The term "peptide" includes chains of amino acids linked by peptide bonds. The term "peptide" can also refer to a "protein" or "polypeptide", which are compounds made of amino acids arranged in a linear chain and folded into a globular form. A variety of polypeptides or proteins may be used within the scope of the methods and compositions provided herein. In certain embodiments, the proteins may comprise antibodies or fragments of antibodies containing an antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the common amino acids found in naturally occurring proteins, or at least one modified or unusual amino acid. Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. Polypeptides made synthetically may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Protein, polypeptide and peptide sequences can be found at computerized databases known to those of ordinary skill in the art. One such database is the National Center for Biotechnology Information's GenBank and GenPept databases. Alternatively, various commercial preparations of proteins, polypeptides, and peptides are known to those of skill in the art.

The term "peptoid" refers to poly-N-substituted glycines, where the N-substituent can be, for example, the side chains of natural or unnatural amino acids. Exemplary peptoids can have e.g., 2-25 residues.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers to any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "prevent," as used herein, refers to prophylactic treatment or treatment that prevents one or more symptoms or conditions of a disease, disorder, or conditions described herein. Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein, or a pharmaceutically acceptable salt or solvate thereof, or a pharmaceutical composition thereof, can be acute, short-term, or chronic. The doses administered may be varied during the course of preventative treatment.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition;

preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Where a group is substituted, the group may be substituted with e.g., 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, halogen (—F, —Cl, —Br, or —I), azido (—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2H$), carboxylic ester (—$CO_2R'$), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, C1-6 alkyl, C2-6 alkenyl, C2-6 alkynyl, aryl, or heteroaryl. In some embodiments, the substituent groups themselves may be further substituted with, for example, 1, 2, 3, 4, 5, or 6 substituents as defined herein. For example, a C1-6 alkyl, phenyl, or heteroaryl group may be further substituted with 1, 2, 3, 4, 5, or 6 substituents as described herein.

The present invention includes all isomeric (e.g., enantiomeric, diastereomeric, and geometric (or conformational)) forms of the compounds; for example, syn and anti isomers, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The present invention includes all pharmaceutically acceptable isotopically-labeled compounds of the invention, wherein one or more atoms are replaced by atoms having the same atomic number, but an atomic mass or mass number different from the atomic mass or mass number usually found in nature. Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Salts derived from appropriate bases include alkali metal, alkaline earth metal, and ammonium salts. Representative alkali or alkaline earth metal salts include sodium, lithium, potassium, calcium, magnesium, and the like. One class of salts includes the pharmaceutically acceptable salts. The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

The term "antibody" is used in the broadest sense and specifically covers, for example, single monoclonal antibodies, antibody compositions with polyepitopic specificity, single chain antibodies, and fragments of antibodies. "Antibody" as used herein includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired agonistic or antagonistic properties described herein. Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Chothia et al., *J. Mol. Biol.*, 186:651-663 (1985); Novotny et al., *Proc. Natl. Acad. Sci. USA*, 82:4592-4596 (1985)]. The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively. Antibodies and antibody fragments are further described herein.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., *Sequences of Proteins of Immunological Interest*, National Institutes of Health, Bethesda, Md. (1987)). The constant domains are not involved directly in binding an antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include chimeric, hybrid and recombinant antibodies produced by splicing a variable (including hypervariable) domain of the antibody of interest with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in Monoclonal Antibody Production Techniques and Applications, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552-554 (1990).

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may include residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

A "human antibody" is one which possesses an amino acid sequence which corresponds to that of an antibody produced by a human and/or has been made using any of the techniques for making human antibodies known in the art or as disclosed herein. This definition of a human antibody includes antibodies comprising at least one human heavy chain polypeptide or at least one human light chain polypeptide, for example an antibody comprising murine light chain and human heavy chain polypeptides. Human antibodies can be produced using various techniques known in the art. In one embodiment, the human antibody is selected from a phage library, where that phage library expresses human antibodies (Vaughan et al. *Nature Biotechnology*, 14:309-314 (1996): Sheets et al. *PNAS*, (USA) 95:6157-6162 (1998)); Hoogenboom et al., *Mol. Biol.* 227:381 (1991); Marks et al., *J. Mol. Biol.* 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology*, 10: 779-783 (1992); Lonberg et al., *Nature*, 368: 856-859 (1994); Morrison, *Nature*, 368:812-13 (1994); Fishwild et al., *Nature Biotechnology*, 14: 845-51 (1996); Neuberger, *Nature Biotechnology*, 14: 826 (1996); Lonberg et al., *Intern. Rev. Immunol.*, 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and*

*Cancer Therapy*, Alan R. Liss, p. 77 (1985); Boerner et al., *J. Immunol.*, 147 (1):86-95 (1991); and U.S. Pat. No. 5,750,373.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region (using herein the numbering system according to Kabat et al., supra). The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cγ2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" in one chain thereof and a corresponding introduced "cavity" in the other chain thereof; see U.S. Pat. No. 5,821,333). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of a Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc.gamma.RIII only, whereas monocytes express Fc.gamma.RI, Fc.gamma.RII and Fc.gamma.RIII. FcR expression on hematopoietic cells is summarized in Table 3 on page 464 of Ravetch and Kinet, Annu. Rev. Immunol., 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA), 95:652-656 (1998).

"Human effector cells" are leukocytes which express one or more FcRs and perform effector functions. Preferably, the cells express at least Fc.gamma.RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR.

Moreover, a preferred FcR is one which binds an IgG antibody (a gamma receptor) and includes receptors of the Fc.gamma.RI, Fx.gamma.RII, and Fc.gamma.RIII subclasses, including allelic variants and alternatively spliced forms of these receptors. Fc.gamma.RII receptors include Fc.gamma.RIIA (an "activating receptor") and Fc.gamma.RIIB (an "inhibiting receptor"), which have similar amino acid sequences that differ primarily in the cytoplasmic domains thereof. Activating receptor Fc.gamma.RIIA contains an immunoreceptor tyrosine-based activation motif (ITAM) in its cytoplasmic domain. Inhibiting receptor Fc.gamma.RIIB contains an immunoreceptor tyrosine-based inhibition motif (ITIM) in its cytoplasmic domain (reviewed in Daron, Annu. Rev. Immunol., 15:203-234 (1997)). FcRs are reviewed in Ravetch and Kinet, Annu. Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol., 117:587 (1976); and Kim et al., J. Immunol., 24:249 (1994)).

DETAILED DESCRIPTION OF THE INVENTION

The methods of conjugate formation described herein employ the specificity of α-haloacetophenone moieties, benzylic halides, quinones, and related electrophilic functional groups for addition reactions and displacements by nucleophiles (e.g., free thiol groups). The methods also employ the potential for useful secondary reactions in certain systems that augment the stability of the initial product. Conjugates prepared according to these methods can include various groups. For example, macromolecules (e.g., polymers such as polyethylene glycols, nucleic acids, carbohydrates (e.g., monosaccharides, disaccharides, oligosaccharides, or polysaccharides) such as polysialic acid, proteins conjugated as homo or hetero-dimers, or proteins conjugated to various small molecule therapeutic, imaging, diagnostic, or optical agents) can be used or prepared in the methods described herein. The present invention further relates to methods of making and using the conjugates themselves or as components in microarrays, the production of fine chemicals and kits, radio-labeling, molecular and optical imaging applications, and the diagnosis and treatment of disorders. In some embodiments, protein conjugates (e.g., those that include one or more annexin proteins) can also be used in these applications.

Conjugates

The methods described herein can be used to prepare conjugates that include a bifunctional linker derived from α-halocarbonyl, alkaryl halide, and quinone reagents, and related moieties. Exemplary conjugates can include a protein (e.g., a protein that is an antibody or a protein modified to include a free cysteine residue) or a biologically active or biologically compatible agent (e.g., polymer, a nucleic acid, carbohydrate, small molecule therapeutic agent, imaging agent, or diagnostic agent).

The methods described herein employ nucleophilic groups (e.g., amino, hydroxyl, or thio functional groups) on the, e.g., proteins, biologically active agents, or biologically compatible agents that can react with electrophilic groups such as α-halo carbonyls, alkaryl halides, quinones, or electrophiles derived from carboxylic and sulfonyl functional groups. Thiol nucleophiles (e.g., cysteine residues) are particularly useful in these methods. If a suitable functional group is not present or not available for reaction with an electrophile, the compound to be conjugated can be modified according to methods known in the art that permit the introduction of an appropriate nucleophilic group (for example, a protein can be modified using protein synthesis methods known in the art to introduce, e.g., a cysteine residue) while retaining any beneficial properties (e.g., therapeutic activity) of the compound.

Protein Conjugates

Chemical crosslinkers and bioconjugation reagents are valuable tools that have been used for a variety of purposes, especially to link biological macromolecules and diverse polymers to both small and large molecular entities whose properties may be enhanced by such combinations. Prominent applications include covalent protein crosslinking techniques to conjugate antibodies, polyethylene glycol polymers, or imaging agents, immobilize ligands, attach haptens to carrier proteins, and stabilize folded protein structures and protein interaction complexes. The present invention applies to all such applications in which thiol groups can be exploited in selective reactions with α-halo-acetophenones and α-haloalkylbenzene derivatives.

Protein-Protein Dimers

Protein dimerization is a natural phenomenon that has important functional consequences in a variety of contexts. Protein-protein interactions are important for regulating functions and for transport across membranes. A number of proteins self-associate to form dimers within protein networks and cascades. (Marianayagam et al., TIBS, 27, 618-625, 2004). Receptor dimerization has been established as a general mechanism for the initiation of signal transduction, and many cell-surface receptors are believed to be activated by such a process, (Rodriguez-Frade et al., *Trends in Immunology*, 22:612-617, 2001; Wang et al., *Annu. Rev. Immunol.* 27:29-60, 2009). These interactions, however, are most often noncovalent and transient. Covalent dimers have been produced synthetically either by disulfide formation from the oxidation of protein thiols or by standard crosslinking techniques (*Bioconjugate Techniques*, Academic Press, New York, 2nd edition, 2008, (Au: G. T. Hermanson) using organic chemical coupling reactions. However, the cross-linking reactions that have been employed are usually not specific and, lacking a specific biochemical driving force that has evolved for functional reasons, are often quite slow in driving protein dimerization to completion (Ashworth et al., *J Cell Sci.* 112:3549-58, 1999). Unnatural covalent dimers that have been produced synthetically by disulfide formation often possess short lifetimes in vivo.

Two factors that impose barriers to dimerization are the limiting solution concentrations of proteins required for homogeneous reaction media, and steric compression resulting from forcing large entities into close proximity. These conditions are often difficult to overcome in actual practice. One strategy is to employ the chemistry of thiol groups to form protein dimers. Disulfide motifs have been used in many instances for coupling biological entities, since the thiol group lends itself to selective redox modifications that do not interfere with other protein functional groups. In principle, with knowledge of structure, cysteines can be installed in each monomeric component and oxidation reactions can create disulfide-linked dimers; specificity, however, can be difficult to achieve when multiple cysteines are present. Cross-linking by bis-maleimide reagents represents another tack. Recently, Rotkoski et al. (*Bioconjug Chem.* 21:1691-702, 2010) have used bis- and tris-maleimides in conjunction with variants of ribonuclease A to form dimers and trimers of these proteins. The generality of this method is presently unclear and, further, each condensation to form thio-succinimides creates a new enantiomeric center that may produce complex mixtures that are difficult to resolve into separate components. These reagents have been most successful when the target entities are in close proximity, as in the case of protein subunits or in membranes. Additionally, maleimide-thiol adducts are unstable over time. This property limits their utility in therapeutics as both duration of action and storage properties are compromised.

Given the limitations of forming stable disulfide dimers in vivo, and the apparent difficulty of preparing homogeneous dimers site specifically using other coupling methods, efficient methods for site-specific protein dimer formation would be useful. Although fusion proteins prepared by recombinant techniques are known in the art and are useful as therapeutics, chemically produced fusions are not limited to fusions at protein termini and can adapt to a wide variety of chemical structures and crosslinks for the preparation of target conjugates. Thus, increasing the range of novel chemical structures by the introduction of chemical modification techniques expands the fusion protein playing field, currently dominated by molecular biology approaches that are limited to protein termini and peptide crosslinks (Schmidt, Curr Opin. in Drug Discovery & Development, 12:284-295, 2009).

To effect site-specific protein dimer formation, two steps are generally necessary to crosslink the component proteins. It is advantageous if the first step can be carried out by using a large excess of the small molecule conjugating reagent so that the rate of formation of the intermediate mono-conjugate can be selectively formed at a practical rate, as exemplified by α-halo-acetophenone methods described herein. The second dimer forming step may be more challenging as the protein concentrations may be difficult to manipulate due to the need to balance solubility with concentration and rate considerations. Therefore, intrinsically rapid coupling reactions are clearly desirable for conjugating proteins in relatively dilute solutions, and these are often at odds with the demands of site-selectivity.

α-Halocarbonyl and Related Conjugates

α-Halocarbonyl reagents, activated halide reagents (e.g., alkaryl halides such as benzyl halide), and related species are known alkylating agents that are capable of labeling amino- and thio-nucleophiles. For example, phenacyl bromides have been used to modify protein nucleophiles. We have discovered that a number of α-halocarbonyl and alkaryl halide species are capable of site-selectively labeling protein cysteine thiols. In one embodiment, we have exploited this preference to selectively prepare protein conjugates by using bifunctional groups that include an additional functional group $QO_2H$ that can be independently modified, chemospecifically by compounds of the structure RYH, where R represents, e.g., a protein, a biologically active agent, or a biologically compatible agent and YH represents a nucleophilic functional group such as hydroxy, thio, or amino (Scheme 1).

Scheme 1

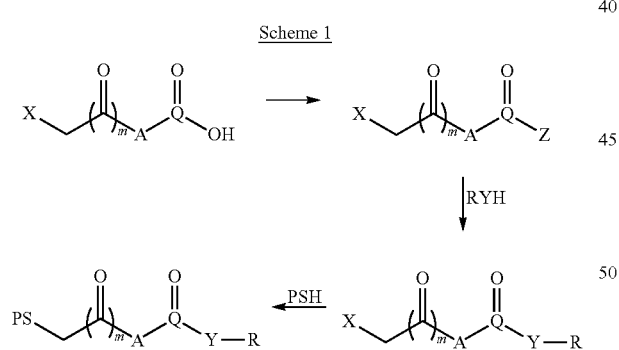

In Scheme 1 and other schemes described herein, substructure A can be selected from a variety of groups, including aryl (e.g., phenyl) and heteroaryl groups. In other embodiments, substructure A is, e.g., optionally substituted naphthyl, by analogy to the exemplary phenacyl chemistry described herein. In still other embodiments, substructure A may represent optionally substituted furan, thiophene, or other non-nucleophilic heterocycles containing two or more heteroatoms capable of bearing protein and biologically active or biologically compatible agents. Additionally, substructure A can include an aryl or heteroaryl group that is linked to another aryl or heteroaryl group via a covalent bond or a molecular linker (e.g., a C1-20 alkyl group, a bis-thioether group, or a polyethylene glycol linker). Exemplary, non-limiting substructures A are shown below in Scheme 2.

Scheme 2

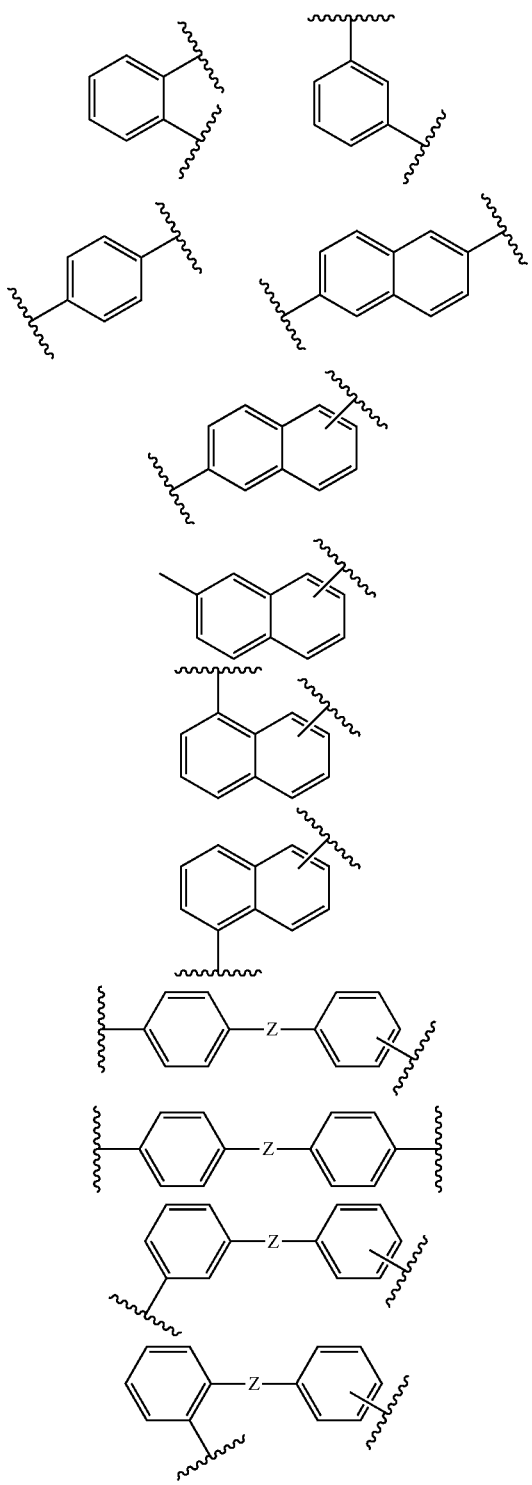

The linking group Z can be, for example, a covalent bond, an optionally substituted C1-20 alkylene group, a polyethyleneglycol group, or a C1-C20 dithioether group. The groups of substructure A, including those shown in Scheme 2, can include additional substituent groups.

For example, in various embodiments, the thiol moieties of free cysteines of proteins (e.g., compounds represented by the formula "PSH") can undergo site-specific alkylation reactions with halo acetyl groups linked to e.g., aromatic or heteroaromatic rings, by displacement of the halide, to form the corresponding protein thioethers as shown in Scheme 3. In some embodiments, the thioether can be part of a phenacyl system (substructure A=phenyl) in which the substituents can independently carry protein and biologically active or biologically compatible agents as part of sulfonamides, carboxamides, esters, and sulfones, etc. These intermediates can be prepared via reactions of appropriately constructed protein and biologically active or biologically compatible agents by reactions known in the art to activate carboxylic acids, sulfonic acids and the like.

Scheme 3

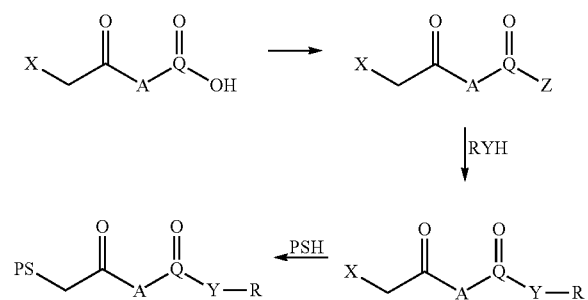

Similar procedures can be used for bifunctional groups having an alkaryl halide group (i.e., compounds of Scheme 1, where m=0).

In other embodiments, the bifunctional linker group includes only α-halocarbonyl or benzylic halide functional groups as exemplified by Scheme 4, where "PSH" represents a protein, biologically active agent, or biologically compatible agent that includes a nucleophilic thiol group. These reagents can be used to prepare symmetrical conjugates (that is, conjugates where both P groups are the same compound) or asymmetrical conjugates (conjugates where each P group is a different compound).

Scheme 4

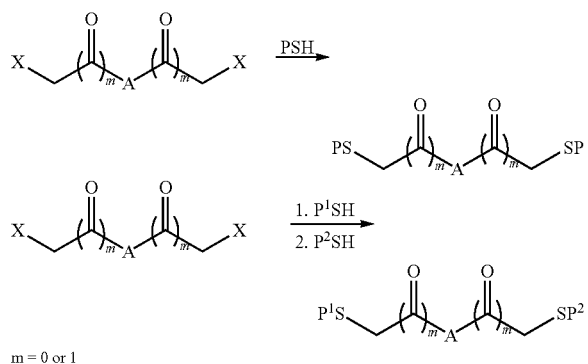

m = 0 or 1

In various embodiments, a nucleophilic group, e.g. a cysteine thiol group, in a protein can undergo alkylation reactions with α-halo-ketones or alkaryl halides to form, e.g., the corresponding thioethers. Reaction of haloketones and alkaryl halides can occur with oxygen, nitrogen, and sulfur nucleophiles (e.g., Erian et al., *Molecules* 8:793-865, 2003). Molecules containing α-bromoacetyl moieties are known to react preferentially with cysteine and methionine residues of proteins. The corresponding chlorides tend to be less reactive than the bromides, and the iodides are more reactive. We have in a broad survey established that bromoacetyl and chloroacetyl moieties linked to aromatic systems are sufficiently activated for alkylation of protein thiols. They, along with the corresponding iodides, are attractive substrates since such α-haloacetophenones bearing amide or sulfonamide ring substituents can be obtained commercially and/or prepared synthetically by those skilled in the art. Commercially useful protein and biologically active or biologically compatible agents (e.g., polyethylene glycol polymers or small molecule therapeutics) can be selectively linked through activated carboxy or sulfonoxy substituents without disturbing the bromo acetyl group or other halocarbonyls as described herein.

In schemes described herein, PSH can be a protein containing at least one free thiol such as natural proteins such as annexin proteins, α-1-antiprotease, human sonic hedgehog N-terminal protein, oncostatin M, primary ribosomal protein S4, and other targetable free cysteines (e.g., annexins I, III, IV, V, VI and VIII, V-128). The present invention can also be applied to antibodies, minibodies, diabodies, affibodies and the like, and mutant proteins in which amino acid residues have been mutated to cysteines.

In a general method, the protein is dissolved in a suitable solvent or buffer. A desired amount of the protein solution is incubated with the α-halo-carbonyl species for about 1-10 hours at a pH of about 6-10 and at a temperature of about 10-60° C. After the incubation is complete, the solution is subjected to centrifuge filtration. Removal of the excess reagents followed by optional purification provides the corresponding 2-thioalkyl-acetophenone systems or its analogs.

In certain embodiments, the chemoselective conversion of the carbonyl species to oximes using aminoxy substrates may be carried out. For example, as shown in Scheme 5, condensation of bifunctional reagents with aminoxy substrates containing an R" group that is, e.g., a protein, a biologically active agent, or a biologically compatible agent, results in the conjugation of an additional protein, biologically active agent, or biologically compatible agent to the protein target. A corresponding mono-oxime conjugate containing an aminoxy terminal side chain (from reaction of a bis-aminoxy substrates and the like) in lieu of a protein and biologically active or biologically compatible agents (not shown) would permit further modifications of the conjugated protein via a three step process. These reagents can be prepared according to procedures analogous to those described in U.S. patent application Ser. No. 13/030,772, International Patent Application No. PCT/US2011/025413, and PCT Publication No. WO2010/040147, each of which is hereby incorporated by reference.

Scheme 5

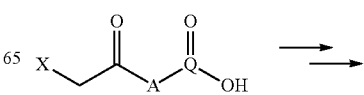

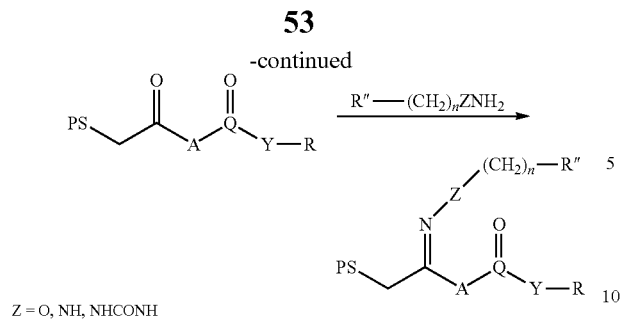

Z = O, NH, NHCONH

Alternatively, the alpha thiol carbonyl conjugate, the primary protein conjugate, may convert to a stable secondary product in which the alpha carbonyl is further reacted with a proximal protein nucleophile, that confers additional stability to the system as represented in Scheme 1. In still other embodiments, a hydrazine or semicarbazide can be used to form conjugates other than an oxime (Scheme 5), since reaction of a hydrazine or semicarbazide with the α-carbonyl group can provide the corresponding hydrazone or semicarbazone respectively. For this embodiment and the use of bis-aminoxy linkers to form oximes incorporating aminoxy functions for further protein and biologically active or biologically compatible agents linkage (see, e.g., PCT Publication No. WO2010/040147).

In a general method, the species (13) is dissolved in a suitable solvent or buffer. A desired amount of the solution of (13) is incubated with a solution containing the carbonyl modifier for about 1-24 hours at a pH of about 3-11 and at a temperature of about 10-60° C. After the incubation is complete, the solution is subjected to centrifuge filtration. Removal of the excess reagents followed by optional purification provides the corresponding oxime or oxime analog product.

Exemplary Bifunctional Reagents

Exemplary bifunctional reagents that can be used to prepare the conjugates described herein are shown in Scheme 6, where Z can be, for example, a covalent bond, a C1-20 alkylene, 0, or a polyethylene glycol link, and representative X groups include Cl, Br, and I.

Scheme 6

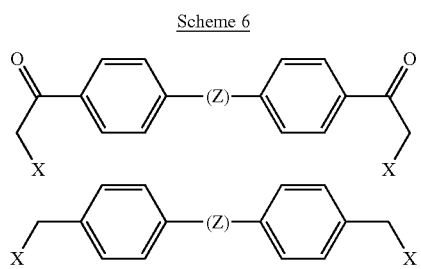

For example, the reagents shown in Scheme 6 can be treated with, e.g., proteins P that include a nucleophilic group (e.g., a thiol group) to form homodimers (Scheme 7).

Scheme 7

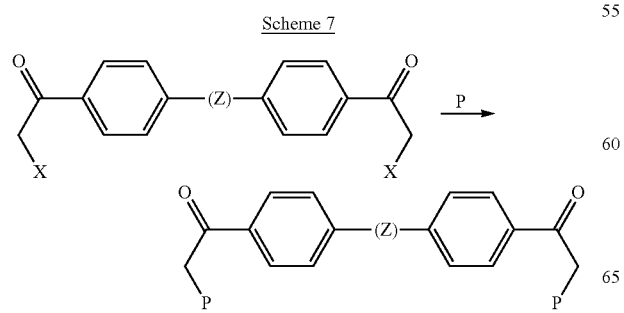

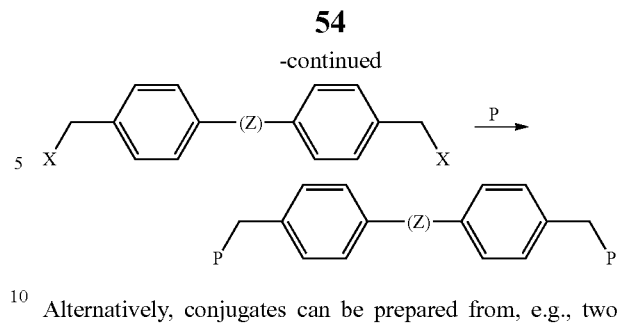

Alternatively, conjugates can be prepared from, e.g., two different proteins (e.g., thiol-containing entities) using stepwise methodologies as shown in Scheme 8 with two differing nucleophilic reagents P and P' as the second reaction is often much slower than the first. Any homodimer species formed can be separated from monomers, e.g., by centrifugation or HPLC.

Scheme 8

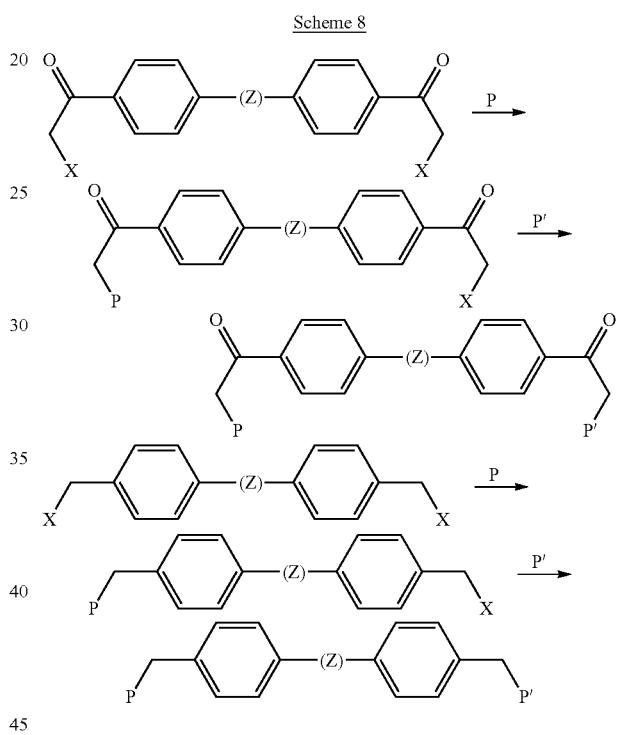

The differential reactivity of α-halo acetophenone functional groups compared to the corresponding benzylic halides also can be exploited in the preparation of heterodimers and other conjugates (Scheme 9). For example, for the differentially activated halides shown below, the first protein moiety can be introduced selectively by displacement of the halide, alpha to the carbonyl, followed by reaction of the benzylic halide. This principle of exploiting differential reactivity by mixing groups of varying, but specific, thiol reactivity can be further extended to include halo-acetamides and the like, in conjunction with more reactive functions such as a-haloacetophenones.

Scheme 9

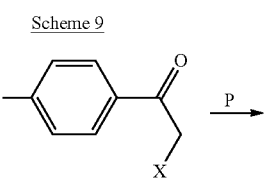

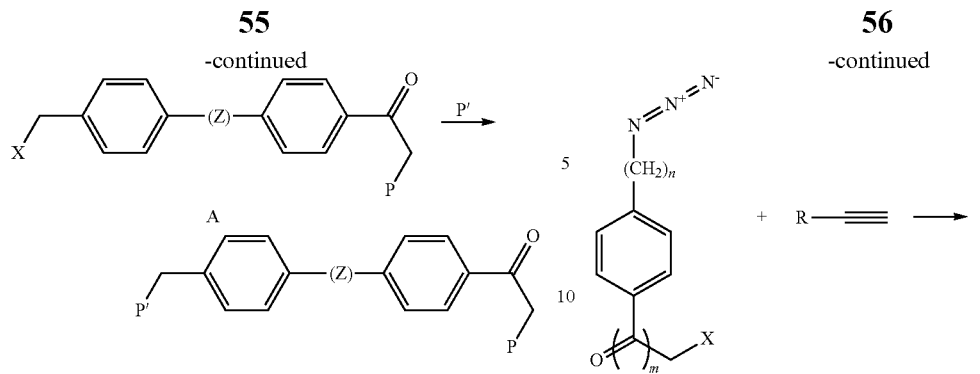

It is to be noted that additional systems can be derived from all the foregoing containing ketone moieties by reduction of the carbonyls. Further, these synthetic schemes can be generalized to other biologically active agents or biologically compatible agents.

Conjugates Including Alkyne and Azide Groups for Cycloaddition

Yet another significant application of a-halobenzyl and a-halo-acetophenones is represented by the heterobifunctional substrates below containing azide or alkyne functionality (Scheme 10). These two functional groups can undergo a Huisgen 1,3-dipolar cycloaddition reaction, a transformation that is regarded as the exemplar of "click chemistry." The facility with which this reaction proceeds, however, is dependent upon a number of factors that impact its rate. For example, the chemistry generally requires the addition of cupric salts to be practical. The use of cupric salts in conjunction with the synthesis of protein conjugates is somewhat limiting because of its potential toxicity, interferences with other metals bound by the native protein, and the difficulties associated with manufacturing. Catalysis of this reaction has also been described using the enzyme acetylcholinesterase as a template: when this enzyme is incubated with libraries of acetylenes and azides, cycloaddition is catalyzed by binding complementary entities in appropriate apposition for reaction.

Scheme 10

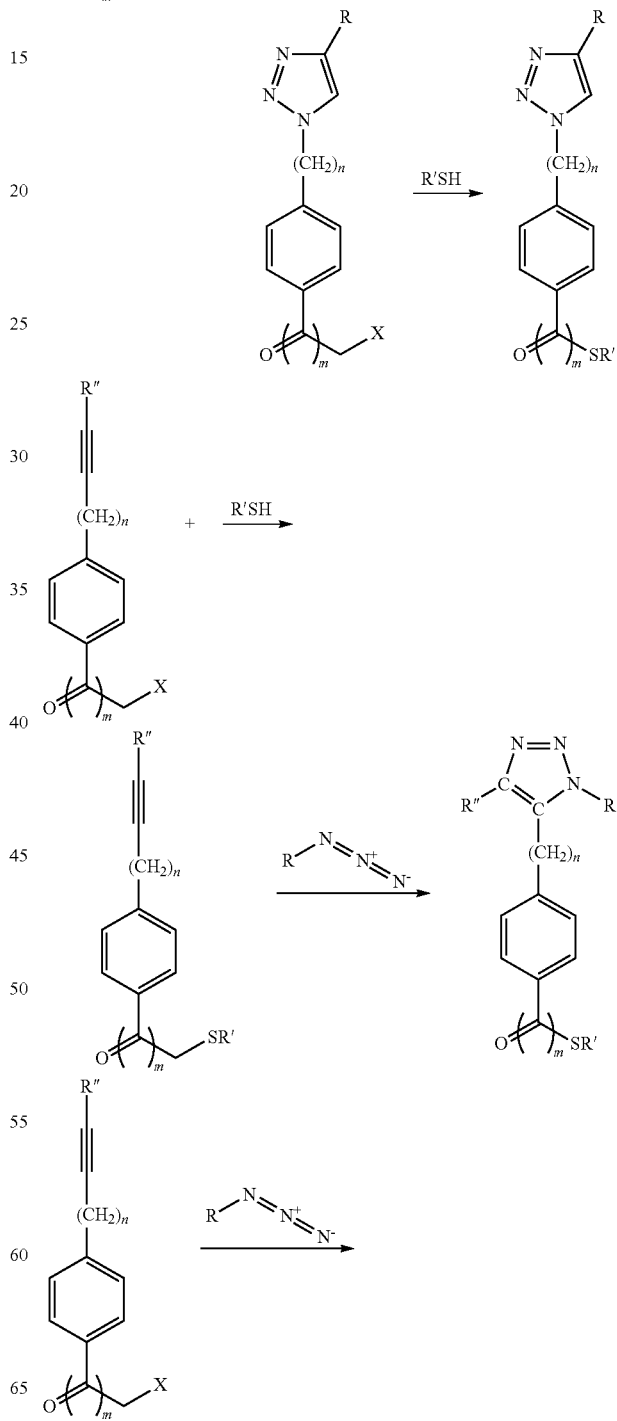

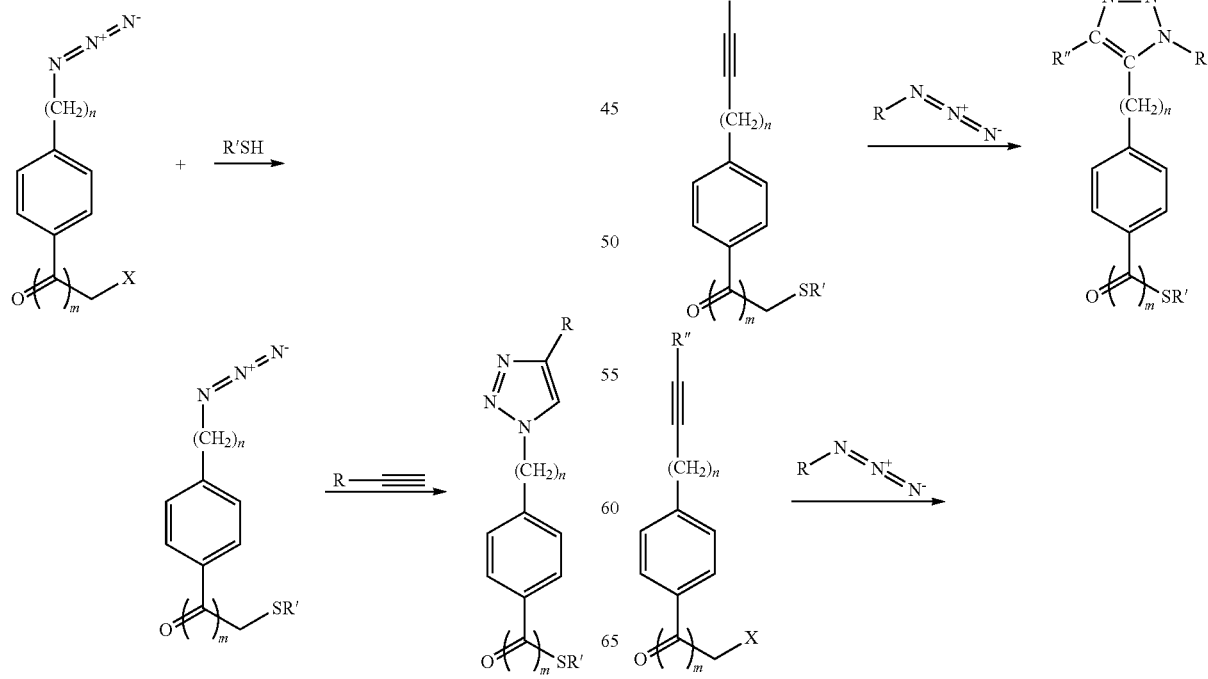

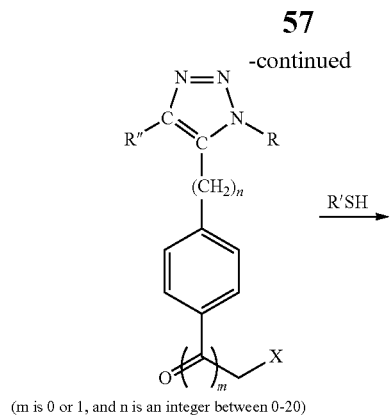

(m is 0 or 1, and n is an integer between 0-20)

The halo and azide functionality can be independently processed in the production of heterodimers. A variety of macromolecules and/or drugs can be combined by first displacing the halide and then adding an alkyne-containing entity to the azide in a 1,3-dipolar addition, or vice versa. An alternative scheme in which both the halide-containing moiety and the alkyne are linked to the ring and the azide is borne by a separate molecule also provides similarly useful heterobifunctional adducts.

The general utility of halomethyl ketones in pairings with cysteine nucleophiles can be exploited using ω-acetylenic halomethyl ketones (Scheme 11). The latter can then be condensed with various azide containing payloads in the above manner.

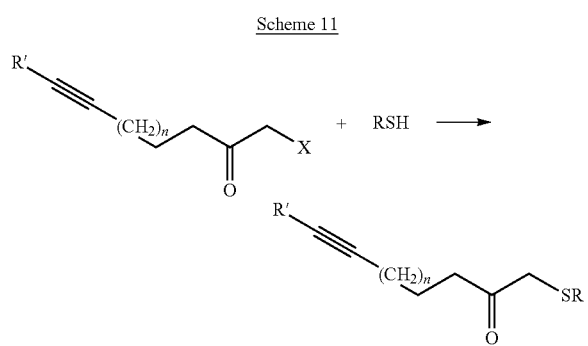

Reduced Conjugates

The conjugated products of α-haloacetophenone substrates, or any other bifunctional reagent that includes a carbonyl group, can also be reduced to the corresponding alcohols (Scheme 12). Reducing agents such as sodium cyanoborohydride ($NaBH_3CN$) are capable of quantitatively reducing the ketone. Chiral reduction of the ketone is also possible using methods and reagents known in the art. The reduction affords a new class of compounds incorporating a benzylic alcohol function that can be used in addition to, or in lieu of, their unsaturated precursors. Reduction eliminates the ketone as a point of attack by biological nucleophiles and enzymes and can afford a more chemically stable functional group. Indeed, we have found pegylated conjugates that include a benzylic alcohol moiety are more stable over a broader pH range than their unsaturated precursors. Accordingly, the increased stability may offer particular advantages in certain applications.

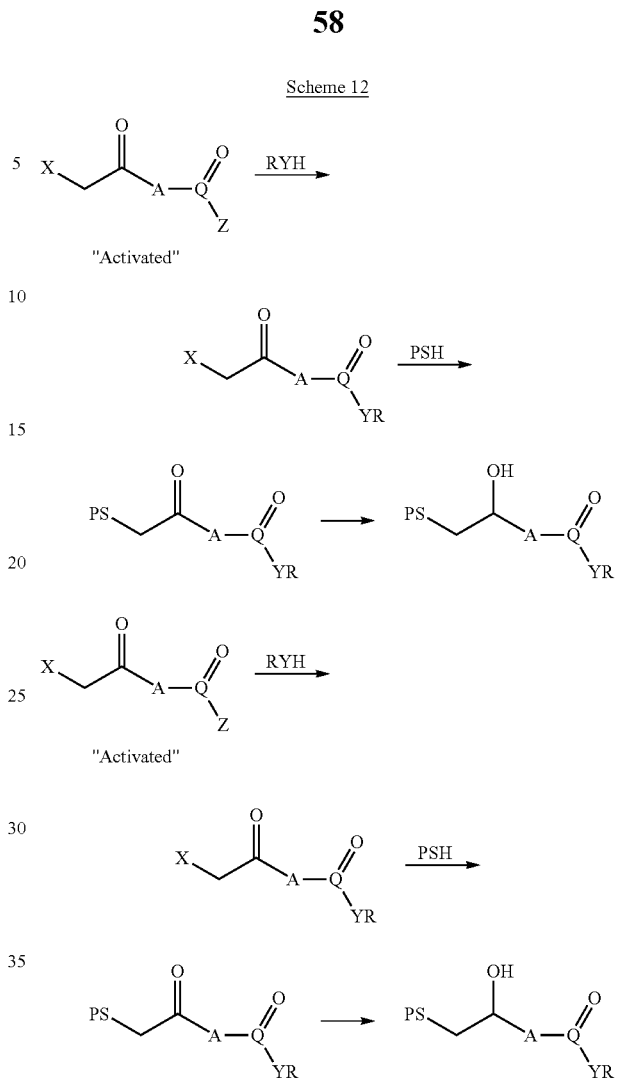

In keeping with the utility of benzylic type conjugates, we have investigated various benzylic halides as substrates for proteins containing free thiols, and found them to be excellent substrates. For example, we have prepared proteins conjugated to polyethylene glycol polymers using the same type of protocols employed for the α-thioacetophenone system. Although displacements of halides from benzylic halides are not as rapid as observed for the corresponding a-haloacetophenones, we have successfully prepared protein conjugates, site-specifically and quantitatively. Thus, we have produced yet another class of conjugates and conjugated products which do not possess the alcohol and ketone functions of the aforementioned systems. Conjugates and conjugated products derived from benzylic halides may provide special stability characteristics that can be employed to extend the duration of action of protein therapeutics.

The scope of conjugated products available from halide-based substrates, incorporating the features above, can be further extended and applied to numerous applications.

Benzoquinone and Related Conjugates

Nucleophilic additions to 1,4-benzoquinones can occur rapidly under a variety of conditions including reactions in aqueous media, and a proposed mechanism for nucleophilic addition is shown in Scheme 13.

Scheme 13

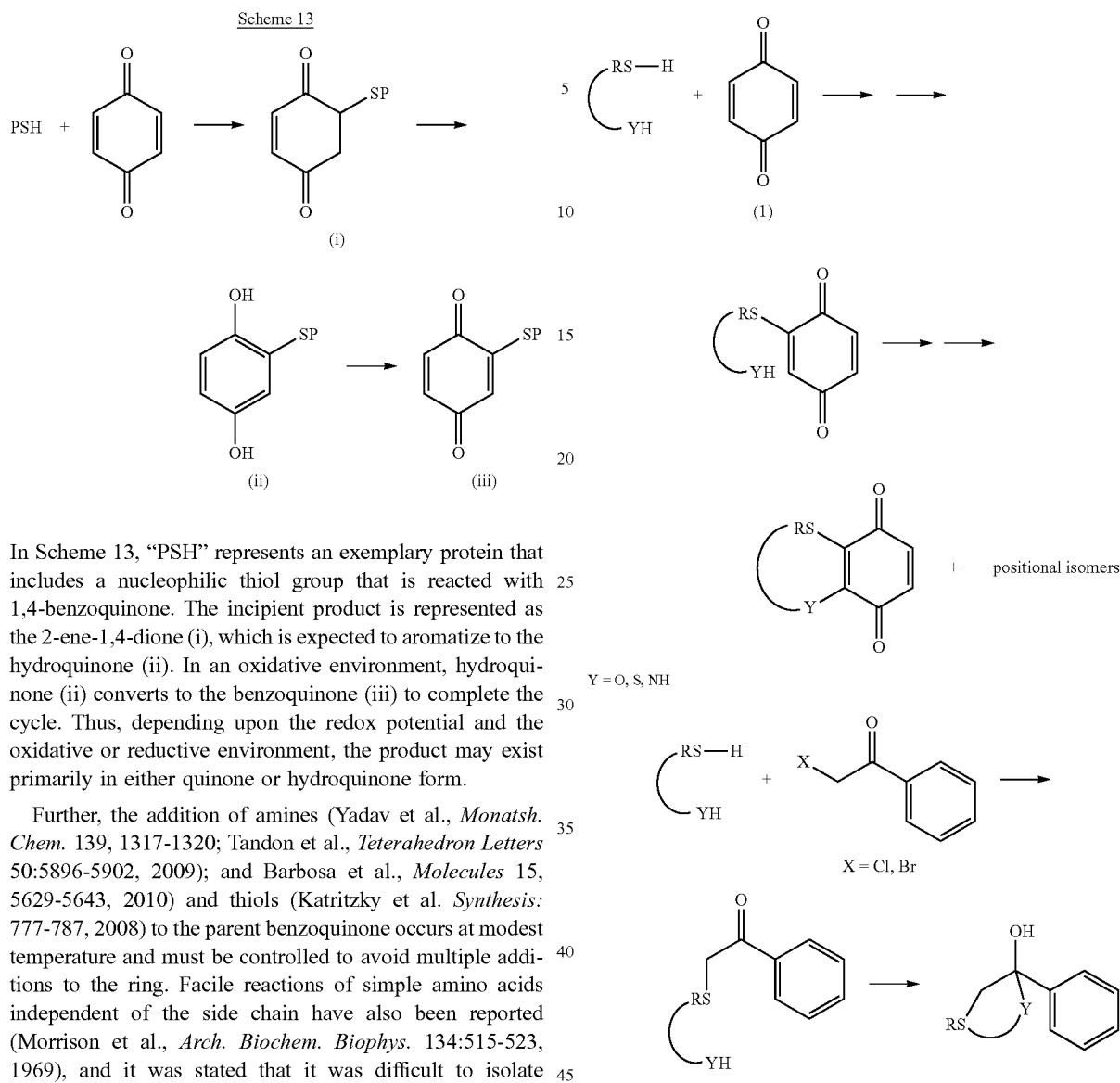

In Scheme 13, "PSH" represents an exemplary protein that includes a nucleophilic thiol group that is reacted with 1,4-benzoquinone. The incipient product is represented as the 2-ene-1,4-dione (i), which is expected to aromatize to the hydroquinone (ii). In an oxidative environment, hydroquinone (ii) converts to the benzoquinone (iii) to complete the cycle. Thus, depending upon the redox potential and the oxidative or reductive environment, the product may exist primarily in either quinone or hydroquinone form.

Further, the addition of amines (Yadav et al., Monatsh. Chem. 139, 1317-1320; Tandon et al., Teterahedron Letters 50:5896-5902, 2009); and Barbosa et al., Molecules 15, 5629-5643, 2010) and thiols (Katritzky et al. Synthesis: 777-787, 2008) to the parent benzoquinone occurs at modest temperature and must be controlled to avoid multiple additions to the ring. Facile reactions of simple amino acids independent of the side chain have also been reported (Morrison et al., Arch. Biochem. Biophys. 134:515-523, 1969), and it was stated that it was difficult to isolate appreciable quantities of the mono-substituted benzoquinone since the second mole equivalent added so rapidly. The 1,4-benzoquinone reaction of horse heart cytochrome c, which contains no free cysteines, was also reported: conjugate formation was attributed to protein primary amino groups or the phenolic groups of tyrosines.

The synthetic methods described herein can also be employed with compounds (e.g., proteins) that include more than one nucleophilic group. For example, Scheme 14 shows a possible mode of reactivity when either a 1,4-benzoquinone reagent or an α-halo carbonyl reagent is combined with a compound (e.g., a protein, a biologically active agent, or a biologically compatible agent) that includes two nucleophilic groups. For example, the two nucleophilic groups can add to different carbons of a benzoquinone ring. When an α-halo carbonyl reagent is used, one nucleophilic moiety can displace the halo leaving group, and the second nucleophilic group can form, e.g., a tetrahedral adduct with the carbonyl group.

These modes of reactivity are also available to compounds (e.g. proteins, biologically active agents, or biologically compatible agents) that include more than two nucleophilic group (e.g., three or four nucleophilic groups). For example, proteins, which contain diverse nucleophiles, successive intramolecular reactions between such nucleophiles and the quinone ring can occur as shown in Scheme 15.

Scheme 15

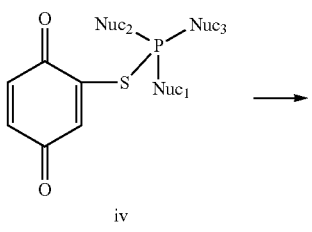

iv

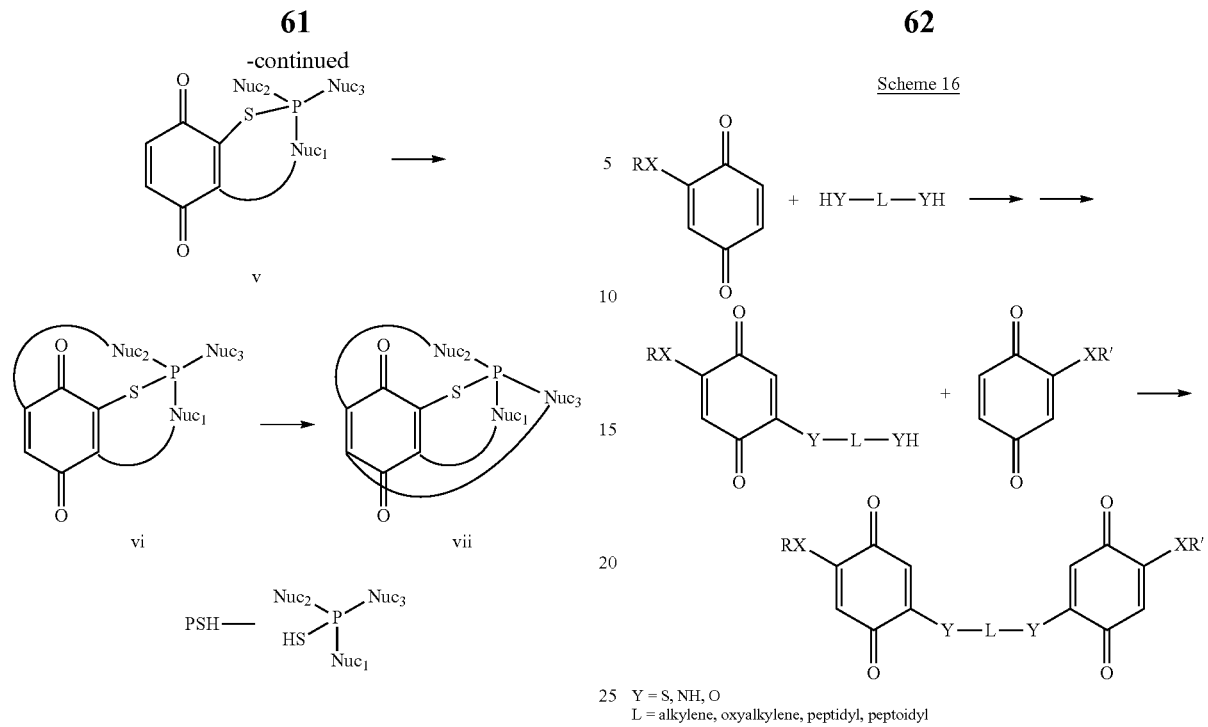

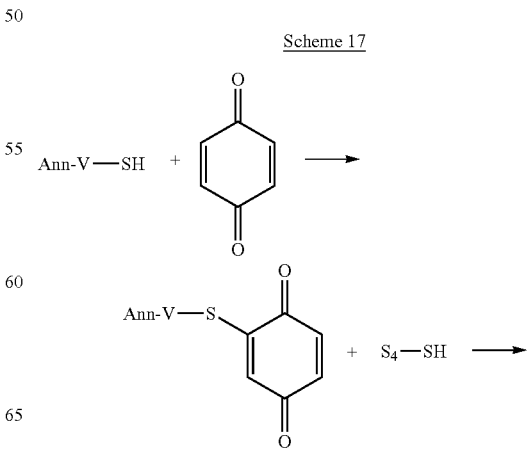

Y = S, NH, O
L = alkylene, oxyalkylene, peptidyl, peptoidyl

In this scheme, the protein PSH includes a thiol nucleophilic group as well as three other nucleophilic groups ($Nuc_1$, $Nuc_2$, and $Nuc_3$). Thus, depending upon the reactivity of the substituted quinone and the reactivity of protein nucleophiles well-disposed for reaction in intermediate (iv), the quinone may ultimately be up to tetra-substituted by a single conjugated protein (as in intermediate (vii)). While 1,4-benzoquinone is used for exemplary purposes, other quinone reagents (e.g., substituted quinones or isomeric benzoquinones) can also be used in the methods.

Accordingly, benzoquinone chemistry can serve as a useful strategy for preparing, e.g., commercially useful conjugates by judiciously controlling reaction conditions. The chemistry of 1,4-benzoquinones is described herein, and analogous methods can be used to prepare conjugates using 1,2- or 1,3-benzoquinones.

Conjugates Via Thiol-Reactive 1,4-Benzoquinones 1,4-Benzoquinone systems can be exploited as site-specific labeling agents of proteins containing free thiols. The regiospecificity of attack may depend upon the pattern and extent of ring substitution. For example, with 2-bromo-1,4-benzoquinone (3) the primary ribosomal protein S4 from *E. coli* (S4 protein; Bellur et al., *Nucleic Acids Res.* April; 37(6):1 886-96, 2009), reacts predominantly by adding to the ring and eliminating bromine. By contrast, wild-type annexin V, which also possesses a lone free cysteine, predominantly reacts by adding to the ring without elimination of bromine Apparently, the pattern of cysteine reactivity of protein targets is dependent upon the steric accessibility of the protein thiol in its local environment. We have found that in certain instances, the free cysteine thiols of two separate protein molecules can be linked to a single 1,4-benzoquinone ring. In other instances, binary units (e.g., quinone rings, each bearing a protein), can be linked in series (Scheme 16, shown for one positional isomer). Accordingly, quinones can be used as scaffolds to conjugate thiol-containing proteins to produce, e.g., homo- or hetero-protein dimers, or to conjugate biologically active or biologically compatible agents to a target protein.

For example, the protein annexin V can be conjugated to the S4 protein, by first labeling annexin V with 1,4-benzoquinone and then treating the resulting conjugate with the S4 protein (Scheme 15). Similarly, we have prepared dimers of S4 thiol that are selectively conjugated by a single 1,4-benzoquinone ring (Scheme 16). Alternatively, a process to crosslink binary benzoquinone-protein units can be employed such that the proteins can reside on separate quinones (Scheme 17). Thus, based on the variable requirements of the quinone ring for conjugating specific entities, the appropriate strategies can be identified and employed to guide the most effective use of quinones as site-specific reagents for the conjugation of protein and biologically active or biologically compatible agents to proteins, and specifically, as mediators of protein dimer formation.

The various scenarios we have developed for exploiting 1,4-benzoquinone reactivity in the production of protein conjugates bearing commercially viable protein and biologically active or biologically compatible agents are described in the figures below (Schemes 17-19).

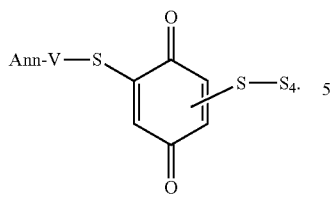

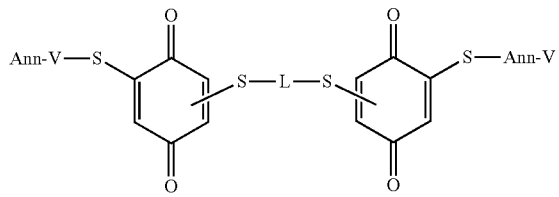

(7)

Ann-V—SH = Annexin V

Parent 1,4-Benzoquinone

In the simple case of addition to the parent quinone without a leaving group substituent (Scheme 20, illustrated for conjugating a protein and biologically active or biologically compatible agents to a protein), there is no prospect for elimination of an atom or group by a displacement reaction under physiological conditions of temperature and pH, and the free cysteine adds to the quinone in Michael fashion to form a conjugate. Thus, the reactive quinone can be first conjugated to the protein target, thereby producing the hydroquinone, which is then oxidized to the quinone oxidation state. The oxidation can be accomplished either spontaneously in the presence of oxygen, or by the use of oxidizing reagents such as excess benzoquinone, $CeSO_4$, potassium ferricyanide, cerium ammonium nitrate, or various other oxidizing agents known in the art to effect redox transformations. A second Michael addition to the ring with the desired protein or biologically active or biologically compatible agent is then implemented.

Scheme 18

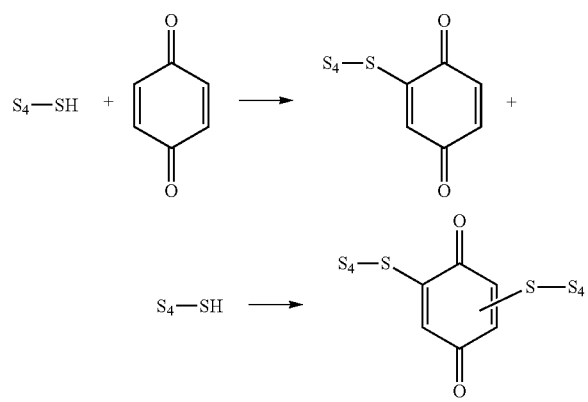

Scheme 19

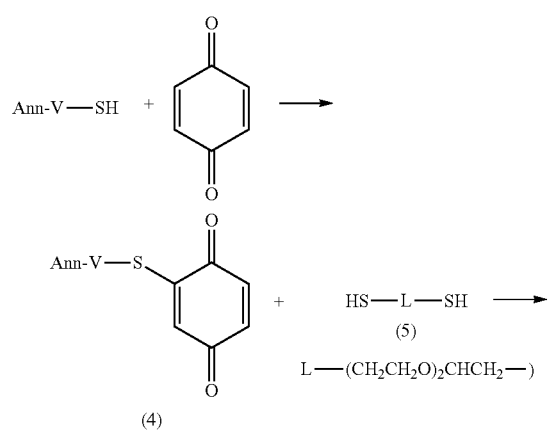

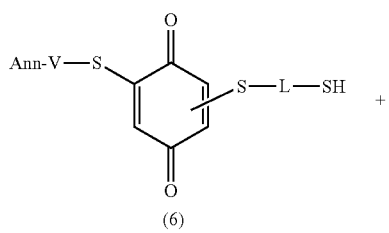

Scheme 20

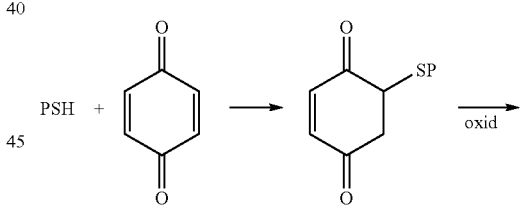

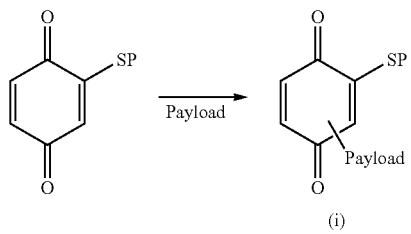

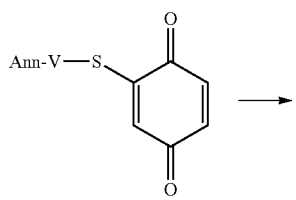

Alternatively, the parent system can be exploited by inverting the addition steps, as in Scheme 21, to first label quinones to carry a biologically active or biologically compatible agent (e.g., a polyethylene glycol polymer) as a ring substituent, which is then reacted with the target protein to produce the hydroquinone product.

Scheme 21

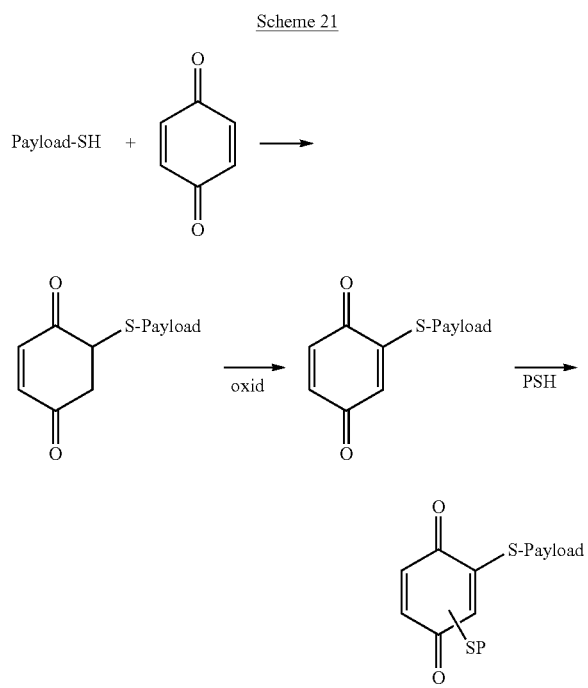

As indicated above, we have discovered that 1,4-benzoquinone can be exploited as a site-specific labeling agent of several proteins containing free thiols, and can be used to crosslink protein and biologically active or biologically compatible agents to the target protein or to produce homo- or hetero-protein dimers. In certain instances, the free cysteine thiols of two separate protein molecules can be linked to a single 1,4-benzoquinone ring. As examples, homodimers of the S4 protein (S4-BQ-S4), and the heterodimers of S4 and annexin V, annexin V and annexin V-128, have been prepared site-specifically (e.g., to a single site on the protein framework), by attachment of the quinone to the free thiol of each protein component.

Monosubstituted 1,4-Benzoquinones

Monosubstituted quinones can also be used in any of the methods described herein. Exemplary monosubstituted quinones include haloquinones, alkylthioquinones, or alkylquinones. For instances in which the quinone is substituted with an atom or a group X that can function as a leaving group (Scheme 22) a scenario in which X is displaced to give the substituted quinone can obtain. This displacement allows for a second addition to the ring (with thiol bearing protein and biologically active or biologically compatible agents) without an oxidation step which can have advantages. Thus two successive additions to the ring can be effected resulting in attachment of the protein PSH to the quinone framework, followed by the addition of the second protein or biologically active or biologically compatible agent to the ring (or vice versa). Additionally, the use of certain monosubstituted benzoquinones (e.g., alkylquinones) can be used to block certain positions of the quinone ring from reacting with the nucleophilic group, thereby guiding the regiochemistry of the reaction sequence.

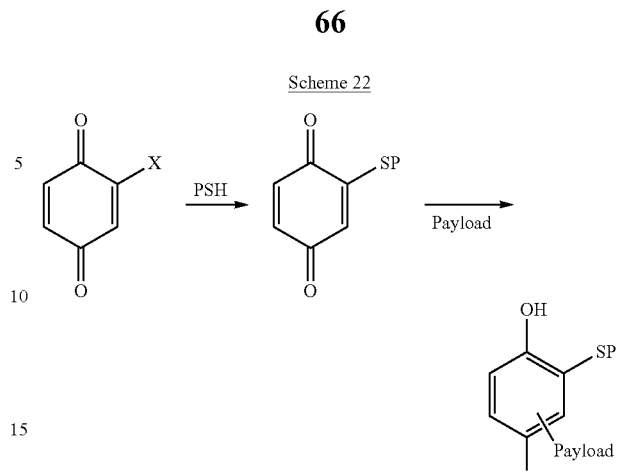

Disubstituted 1,4-Benzoquinones

Disubstituted 1,4-benzoquinones can be useful substrates for introducing two entities onto a ring in tandem displacement reactions. Disubstituted 1,4-benzoquinones such as 2,6-dibromo-1,4-benzoquinones are available commercially. Similarly, dialkylquinones can also be used in the methods described herein. Tandem additions to the quinone are possible through the sequence described in Scheme 23.

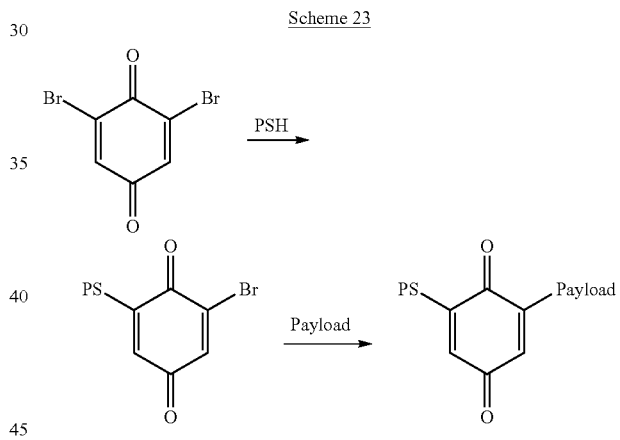

It will be appreciated that the pattern of reactivity of the protein will dictate the sequence to be employed. It will also be appreciated by those trained in the art that, having the three possible options allows for flexibility in design of quinones carrying protein and biologically active or biologically compatible agents. For example, if the protein is not able to displace a potential leaving group, but able to add nucleophiles to the ring, then ring reactions can be accomplished through sequence A. Alternatively, if the protein is capable of displacing leaving group substituents, it can be directed toward particular positions of the ring.

Protein Crosslinking: "One Ring, One Protein"

We have established that 1,4-benzoquinones can act as highly specific and reactive labeling reagents of cysteine thiols of diverse proteins, e.g., annexin V, annexin V-128, and S4. The general nature of this reaction defines a path to protein dimers in stepwise fashion: (1) conjugation of the quinone to the protein, (2) oxidation of the product hydroquinone, and (3) addition of a second protein thiol. Whereas the formation of monoconjugates between protein and quinone substrates has proved to be general, the coupling reaction of the second protein could, in certain instances, be challenging. In instances where addition of a second protein to a quinone ring may be difficult to effect, an alternative strategy has been developed that is based on the specificity of binary 1,4-benzoquinone-protein units as thiol-protein acceptors. In this manner, protein dimers and multimers can be prepared. We have combined two such units to give dimers by employing bis-thiol coupling regents so that each ring need not bear more than one protein molecule (Scheme 22).

For example, we have been able to achieve annexin V homodimers corresponding to (7) by condensing a first binary annexin V-1,4-benzoquinone unit (4) with the bis-thiol (5, X=S) to give the tethered system (6) (Scheme 17). Reaction of the latter with a second binary annexin V-1,4-benzoquinone unit results in the homodimer (7). This stepwise sequence, generalized in Scheme 3, can be adapted to the synthesis of heterodimers by choosing distinct protein and biologically active or biologically compatible agents RSH and R'SH. There are additional variants which achieve the objective of preparing bis-quinones bearing separate protein and biologically active or biologically compatible agents. that are shown in Scheme 24, illustrated for 1,4-benzoquinone. Eq. 1 utilizes the parent bis-quinone (8) as a substrate for coupling proteins (protein and biologically active or biologically compatible agents) to form dimers. Another variant, which employs the unsymmetrical bis-quinone (9), can accept a second protein or biologically active or biologically compatible agent to form a dimer.

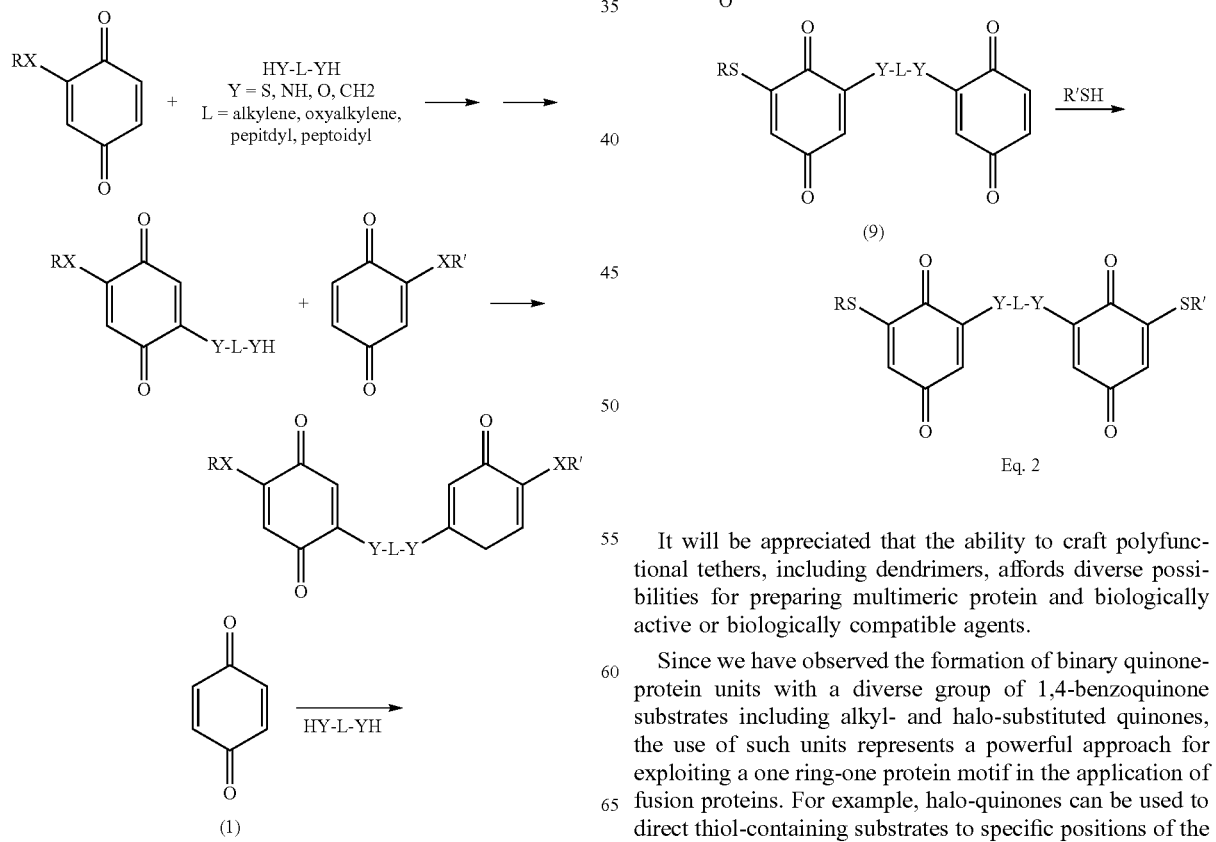

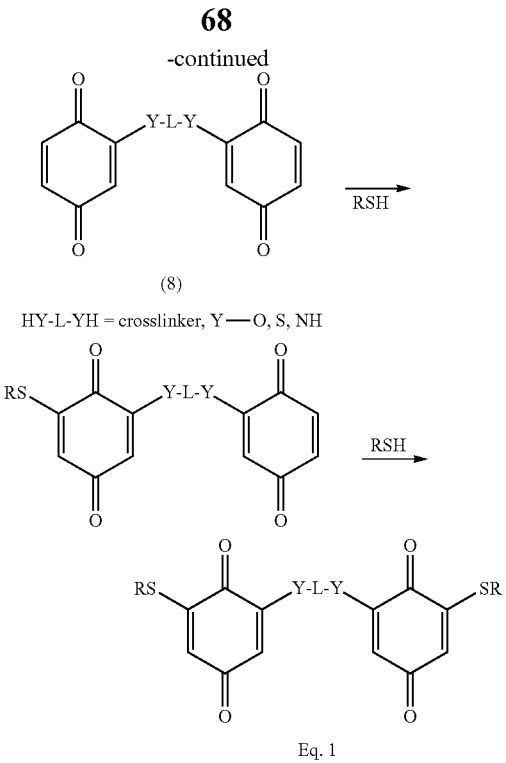

It will be appreciated that the ability to craft polyfunctional tethers, including dendrimers, affords diverse possibilities for preparing multimeric protein and biologically active or biologically compatible agents.

Since we have observed the formation of binary quinone-protein units with a diverse group of 1,4-benzoquinone substrates including alkyl- and halo-substituted quinones, the use of such units represents a powerful approach for exploiting a one ring-one protein motif in the application of fusion proteins. For example, halo-quinones can be used to direct thiol-containing substrates to specific positions of the ring via displacement reactions of halide. Alkyl substituents can be used to block specific positions of the ring to facilitate the formation of homogeneous products and limit toxic mechanisms.

Further, a variety of tethers can be envisaged which employ alkyl, alkylene oxides, peptide or peptoid chains to join two quinone rings. The nucleophiles that initiate attack on the quinone framework may be oxygen-, nitrogen- or sulfur-based (X=O,S,N). Since alcohols, amines and thiols are all capable of being introduced onto quinone rings by specific displacements of nucleofuges, there is the prospect of combining various imaging agents, drugs and the like, with quinone substrates.

As shown in Scheme 25, bis-quinones in which alkyl chains are linked directly to the quinone ring can be prepared by a chemist of ordinary skill by methods known in the art: (Russell et al., *J. Chem. Soc., Chem. Commun.,* 1987; Witiak et al. *Med. Chem.* 1989, 32, 1636-1642). Still other exemplary methods are described in (Dillmore et al., *Langmuir* 20(17):7223-31, 2004; Yeo et al., Langmuir 22(25):10816-20, 2006; and Yousaf et al., *J. Am. Chem. Soc.* 121, 4286-4287, 1999). These analogs may be especially useful in the formation of multimers as the carbon chain tether is not displaceable by nucleophiles.

Diels-Alder Reactions of Quinones

Quinones offer another opportunity for conjugate formation as these are well-known Diels-Alder dienophiles. The mode of reactivity is illustrated in Scheme 26 for a protein and biologically active agents-bearing dienes. The Diels-Alder reaction can be exploited to crosslink protein and biologically active or biologically compatible agents to proteins either by derivatizing the diene or the 1,4-benzoquinone, with the protein and biologically active or biologically compatible agents to be conjugated. The Diels-Alder reaction constitutes an excellent version of "click chemistry" in the fashion of 1,3-dipolar addition reactions as the chemistry is orthogonal to protein chemistry and is accelerated by water (Michito et al., *Science* 312:251-254, 2006, and references therein) and various catalysts.

Scheme 26

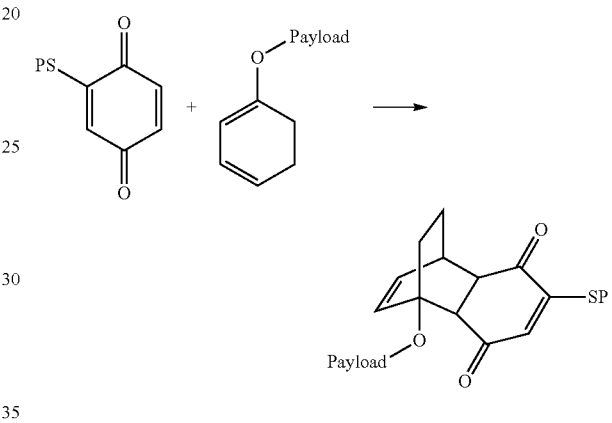

There are precedents for facile reactions of thio-substituted p-benzoquinone with dienes such as cyclopentadiene, and we have successfully performed novel Diels-Alder reactions of protein-1,4-benzoquinone conjugates to demonstrate the feasibility.

It will also be appreciated that the reactions of thiol nucleophiles cited above, can be effected by amines (e.g., Katritzky et al., *Synthesis* 777-787, 2008). These entities constitute another opportunity to exploit the conjugation of proteins to protein and biologically active or biologically compatible agents where the protein and biologically active or biologically compatible agents is attached to an appropriate amine.

An extraordinary feature of quinone reactions of thiol-containing species which possess nucleophiles in the vicinity of a reactive thiol, is the possibility of multiple attachments to the quinone acceptor (Scheme 13). The reaction of the second nucleophile gives cyclized product and provides a basis for additional stability of quinone conjugates and related conjugated products. This feature can be especially advantageous for instances where duration of action is essential, e.g., therapeutic proteins, antibody conjugates. We have shown for instance that 2-aminoethylmercaptan derivatives have a strong tendency to form six member rings and that certain proteins appear to undergo secondary reactions when conjugated to 1,4-benzoquinones (Scheme 27). This feature may be exploited in the design of mutant proteins by fusing suitably designed peptide moieties that contain cysteine and lysine in proper apposition for tandem quinone reactions.

Scheme 25

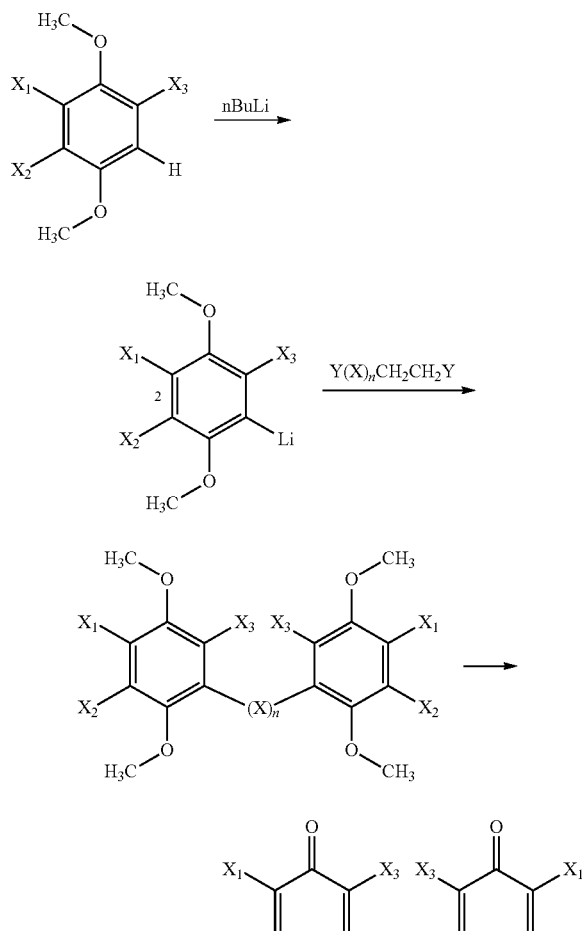

Y = I, Br, Cl; X = CH$_2$, CH$_2$CH$_2$O,; n = 0-40

Scheme 27

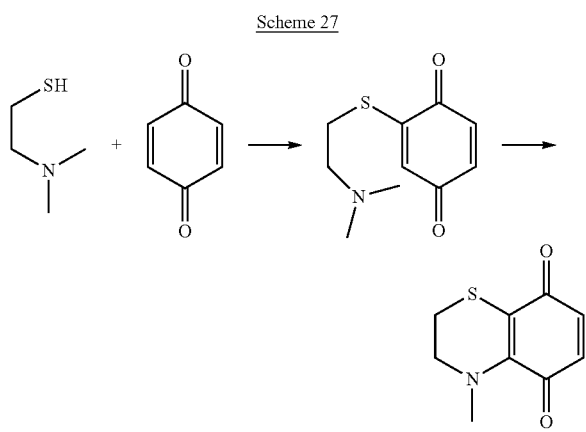

Halopyruvate Reagents

Halopyruvate reagents can also be used to prepare conjugates described herein. Halopyruvates have been primarily studied in enzyme reactions where they are usually used as mimics of substrates for pyruvate-processing enzymes. In some instances, pyruvates have proved to react selectively with protein thiols, but they have also demonstrated a proclivity to covalently label other nucleophilic amino acid side chains (e.g., Korotchkina et al., *Arch Biochem Biophys*, 369(2)277-87, 1999; Stamps et al., *Biochemistry*, 37(28): 10195-202, 1998; Abeysinghe et al., *J. Mol. Biol.* 220(1): 13-16, 1991; Huynh, *Arch. Biochem. Biophys.* 284(2):407-12, 1999; and Vlahos et al., *J. Biol. Chem.* 265(33):20384-9, 1990).

Exemplary methods are described herein. For example, in Schemes 28-31, PSH can be a protein containing at least one free thiol such as natural proteins as annexin V, α-1-antiprotease, human sonic hedgehog N-terminal protein, oncostatin M, primary ribosomal protein S4, and proteins containing targetable free cysteines (e.g., annexins I, III, IV, V, VI and VIII). The present invention can also be applied to antibodies, minibodies, diabodies, affybodies and the like, and mutant proteins in which amino acid residues have been mutated to cysteines.

In various embodiments, the thiol group of free cysteines of proteins can undergo an alkylation reaction with α-halo pyruvyl systems to form the corresponding thioether by displacement of the halide as shown in Scheme 28.

Scheme 28

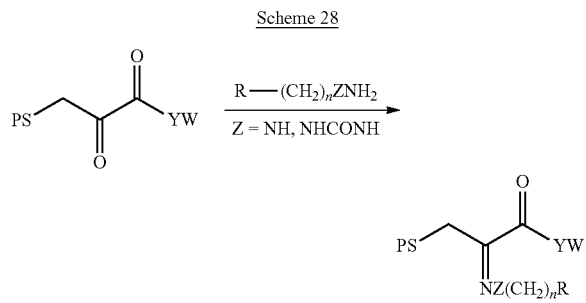

Y = NR (R = H, optionally substituted alkyl or aryl), O, or a covalent bond W = H, optionally substituted alkyl, optionally substituted aryl, a protein, a biologically active agent, or a biologically compatible agent n = 0 or 1

In certain preferred embodiments, the thioether can be a β-thioether as part of an α-ketoamide (Y=N), α-keto acid (YW=OH), α-keto ester (Y=OR, R=alkyl or optionally substituted aryl or payload), or α-diketone network. In other preferred embodiments the thioether may be a β-thio-α-diketone. In still other important above embodiments, the thioether produced may be part of a network containing a heterocyclic moiety in Y or W.

The pyruvate entity may be in the form of an ester or amide function that carries a desired protein, biologically active agent, or biologically compatible in Scheme 28. Site specific alkylation of proteins such as annexin V, α-antiprotease, or human sonic Hedgehog N-terminal protein and the aforementioned affords several additional possibilities for functionalizing the activated carbonyl group within the α-dicarbonyl linkage. In certain embodiments, the chemoselective conversion of the α-dicarbonyl species to oximes using aminoxy substrates can be carried out.

In a general method, the pyruvate is dissolved in a suitable solvent or buffer. A desired amount of the pyruvate solution is incubated with a solution containing the carbonyl modifier for about 1-24 hours at a pH of about 3-11 and at a temperature of about 10-60° C. After the incubation is complete, the solution is subjected to centrifuge filtration. Removal of the excess reagents followed by optional purification provides the corresponding oxime or oxime analog product.

As described herein for, e.g., conjugates derived from α-halocarbonyl and related functional groups, in some instances it may be desirable to convert the α-carbonyl of the protein conjugate to a hydroxy function by reduction using, e.g., sodium cyanoborohydride (Scheme 29).

Scheme 29

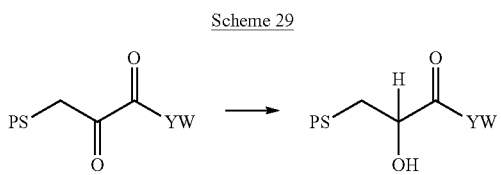

Acrylic Acid Derivatives and their Cyclic Analogs

In various embodiments, the thiol groups of free cysteines of proteins can undergo alkylation reactions with acrylic acid derivatives to form either the 3-propanoyl product when X is H, alkyl, or another non-displaceable group, or the β-thio-acryloyl adduct when X is a displaceable group such as bromine (Schemes 30 and 31). As shown in Scheme 29, in some embodiments, the Z group may also include a linker to a moiety R that is another protein, biologically active group, or biologically compatible group.

Scheme 30

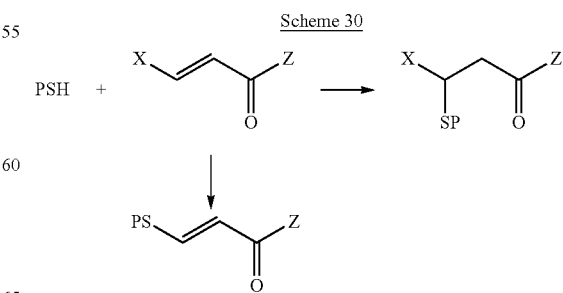

Z = H, alkyl, aryl, alkoxy, aryloxy, or NR$_2$, where each R is H, alkyl, or aryl Scheme 31

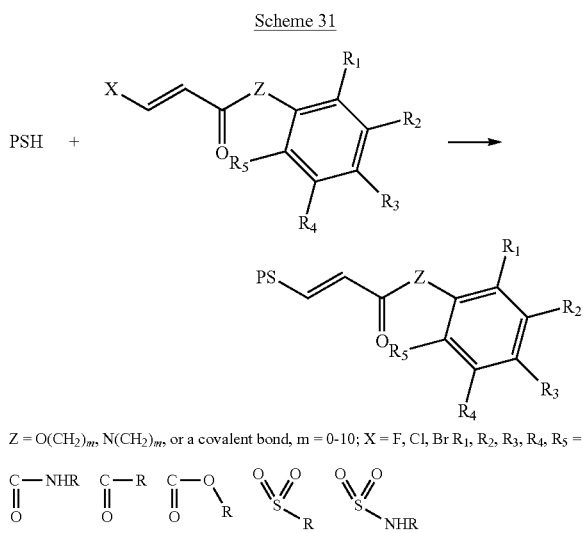

Z = O(CH$_2$)$_m$, N(CH$_2$)$_m$, or a covalent bond, m = 0-10; X = F, Cl, Br R$_1$, R$_2$, R$_3$, R$_4$, R$_5$ =

$\underset{O}{\overset{}{C}}$—NHR  $\underset{O}{\overset{}{C}}$—R  $\underset{O}{\overset{}{C}}$—O\_R  $\overset{O}{\underset{R}{\overset{\|}{S}}}\overset{O}{\|}$  $\overset{O}{\underset{NHR}{\overset{\|}{S}}}\overset{O}{\|}$ In a general method, the protein is dissolved in a suitable solvent or buffer. A desired amount of the protein solution is incubated with the acrylic acid derivative for about 1-10 hours at a pH of about 6-10 and at a temperature of about 10-60° C. After the incubation is complete, the solution is subjected to centrifuge filtration. Removal of the excess reagents followed by optional purification provides the corresponding 3-thio substituted carbonyl systems.

Peptides, Polypeptides and Proteins

Proteins, peptides, and polypeptides may be made by any technique known to those of skill in the art, including the expression of proteins, polypeptides or peptides through standard molecular biological techniques, the isolation of proteins or peptides from natural sources, or the chemical synthesis of proteins or peptides. Exemplary peptides, polypeptides, and proteins that can be used in the methods described herein are also described in, for example, U.S. Patent Publication No. 20100099649, which is herein incorporated by reference in its entirety. Still others include annexins, α-1-antiprotease, human sonic hedgehog N-terminal protein, oncostatin M, primary ribosomal protein S4, and, generally, other targetable free cysteines.

Modified proteins can also be used in the methods described herein, where the native sequence or molecule is altered in such a way without materially altering the membrane binding affinity of the protein. Such modified proteins can be produced by chemical, genetic engineering, or recombinant techniques. The modification can include sequence modification through the addition of several amino acid residues, and/or an addition/deletion of an amino acid at a single site on the native or genetically engineered sequence. In the context of the present invention, modified proteins include proteins modified to include a cysteine residue having a free thiol (—SH) group.

For example, a modified protein can have an amino acid sequence with at least one amino acid substitution (e.g., 2, 3, 4, 5, 6, 7, 8, 9, 10, 11, or 12 substitutions) compared to the naturally occurring sequence. The protein may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. Alternatively, the modified protein has an amino acid sequence that has at least 35%, 40%, 50%, 60%, 65%, 70%, 75%, 80%, 85%, 90%, or 95% identity to the amino acid sequence of the naturally occurring peptide.

Biologically Active and Biologically Compatible Agents

In addition to proteins, other biologically active agents and biologically compatible agents can be used in the methods described herein. Exemplary agents include polymers (e.g., polyethylene glycol), nucleic acids, carbohydrates (e.g., monosaccharides, disaccharides, oligosaccharides, and polysaccharides) such as polysialic acid, small molecule therapeutic agents, imaging agents, diagnostic agents, prophylactic agents, and optical agents. The resultant conjugates be used, e.g., for targeted delivery of the biologically active agent or the biologically active agents. Conjugates that include annexin proteins may be of particular interest. As shown herein in the Examples, the annexin conjugates prepared retain their biological activity post-modification. Further, the use of these conjugates (e.g., conjugates that include an annexin protein) as couriers to elevated sites of apoptosis/necrosis may be useful in methods of medical treatment and may be particularly important in the case of heart and cells of other vital organs. See, e.g., Kenis et al., "Annexin A5 uptake in ischemic myocardium: demonstration of reversible phosphatidylserine externalization and feasibility of radionuclide imaging," J. Nucl. Med. 51(2):259-67, 2010.

In addition to the use of the conjugates described herein for methods of selective delivery of therapeutic agents to sites of elevated apoptosis and necrosis. The preparation of fusion proteins is well known in the art (see, e.g., Chamow et al., Antibody Fusion Proteins, Wiley-Liss, 1999). For example, recombinant DNA methods can be used to prepare fusion proteins. In particular, fusion proteins that include annexin can be useful for targeted delivery of therapeutic agents. Exemplary fusion proteins that include annexin are described in, e.g., U.S. Pat. Nos. 7,407,475 and 7,262,167.

The conjugates and fusion proteins can also include, in addition to an annexin protein, various proteins, biologically active agents, or biologically compatible agents, including those described in U.S. Pat. Nos. 7,906,118 and 7,534,585, herein incorporated by reference in its entirety. Exemplary groups can be selected from a cytokine, a stem cell growth factor, a lymphotoxin, a hematopoietic factor, a colony stimulating factor (CSF), an interferon (IFN), erythropoietin, thrombopoietin, or a combination thereof.

Exemplary cytokines include interleukins (IL), interferons (IFN), chemokines, tumor necrosis factor receptor ligands (e.g. 4-1BBL, OX40L, GITRL), killing inhibitor receptor (KIR) ligands, killing activatory receptor (KAR) ligands, IFN regulatory factors (IRFs) and B cell stimulatory factors. For example, the conjugates can include cytokines such as MIF (macrophage migration inhibitory factor), HMGB-1 (high mobility group box protein 1), TNF-α (tumor necrosis factor α), any of interleukins 1-19 and 23-24, any of chemokines 5, 10, 19, and 21, MCP-1 (monocyte chemotactic protein-1), any of macrophage inflammatory proteins1A and 1B, ENA-78, MCP-1 (monocyte chemoattractant protein), GRO-.beta., Eotaxin, interferon-α, interferon-β, interferon-γ, G-CSF, GM-CSF, SCF, PDGF, MSF, Flt-3 ligand, erythropoietin, thrombopoietin, CNTF, leptin, oncostatin M, VEGF, EGF, FGF, P1GF, insulin, hGH, calcitonin, Factor VIII, IGF, somatostatin, tissue plasminogen activator, and LIF.

Anti-cancer antibodies can also be used in the conjugates or fusion proteins described herein. For example, anti-cancer antibodies include, but are not limited to, hR1 (anti-IGF-1R) hPAM4 (anti-MUC1), hA20 (anti-CD20), hA19 (anti-CD19), hIMMU31 (anti-AFP), hLL1 (anti-CD74), hLL2

(anti-CD22), hMu-9 (anti-CSAp), hL243 (anti-HLA-DR), hMN-14 (anti-CEA), hMN-15 (anti-CEA), hRS7 (anti-EGP-1) and hMN-3 (anti-CEA)

In particular, the use of fusion proteins and/or of conjugates that include annexin can be useful for the treatment or prevention of diseases characterized by increased necrotic or apoptotic activity in cells. For example, the conjugates and fusion proteins can be used for the treatment or prevention of cancer and other proliferative diseases, inflammation and inflammatory diseases (e.g., inflammatory bowel disease and rheumatoid arthritis) Crohn's disease, and diabetes.

Cancers that may be treated according to the methods described herein include, but are not limited to, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

Proliferative diseases that may be treated according to the methods described herein include dyslasia, benign dysproliferative disorders, leukoplakia, Bowen's disease, keratoses, Farmer's Skin, solar cheilitis, solar keratosis, obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Still other proliferative diseases are described in U.S. Pat. Nos. 5,639,600 and 7,087,648, hereby incorporated by reference.

Therapeutic Agents

Exemplary classes of therapeutic agents include, but are not limited to carbohydrates, anti-microbials, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogel and ramatroban, antibodies, neurotransmitters, psychoactive drugs, oligonucleotides, proteins, lipids, and combinations thereof.

Additional therapeutic agents that can be used in the methods described herein include, without limitation, growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutylric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothcnic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active or biologically compatible agent can be an anti-inflammatory agent, such as an NSAID, corticosteriod, or COX-2 inhibitor, e.g., rofecoxib, celecoxib, valdecoxib, or lumiracoxib. The therapeutic agent may also include antibiotics.

Diagnostic Agents

Exemplary diagnostic agents which can be used in the methods described herein include, without limitation, imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials. Other diagnostic agents that can be used in the methods described herein include those described in U.S. Patent Publication No. 20100099649, which is herein incorporated by reference in its entirety.

Antibodies and Antibody Fragments

Any of the conjugates described herein can include an antibody or an antibody fragment as described herein. The use of antibodies and antibody fragments in methods of treatments and in the preparation of immunoconjugates has been reviewed in: Holliger et al., *Nature Biotechnology*, 23(9):1126-1136 (2005); Wu et al., *Nature Biotechnology* 23(9):1137-1146 (2005); Tanaka et al., *Cell Cycle* 7(11): 1568-1574 (2008); Kreitman, *The AAPS Journal*, 8(3): E532-E551 (2006); and Hudson et al., *Nature Medicine*, 9(1):129-132 (2003), each of which is hereby incorporated by reference.

Antibodies include intact monoclonal and polyclonal antibodies, as well as various genetically engineered antibodies.

Antibody fragments can be produced using standard methods. Exemplary antibody fragments include monovalent (e.g., Fab, scFv, single variable $V_H$ domain, and single variable $V_L$ domain fragments) and divalent fragments (e.g., Fab'$_2$ fragments, diabodies, triabodies, tetrabodies, and minibodies). Truncated versions of monoclonal antibodies, for example, can be produced by recombinant methods in which plasmids are generated that express the desired monoclonal antibody fragment(s) in a suitable host. Ladner (U.S. Pat. Nos. 4,946,778 and 4,704,692) describes methods for preparing single polypeptide chain antibodies. Ward et al., Nature 341:544-546, 1989, describes the preparation of heavy chain variable domain which have high antigen-binding affinities. McCafferty et al. (Nature 348:552-554, 1990) show that complete antibody V domains can be displayed on the surface of fd bacteriophage, that the phage binds specifically to antigen, and that rare phage (one in a million) can be isolated after affinity chromatography. Boss et al. (U.S. Pat. No. 4,816,397) describes various methods for producing immunoglobulins, and immunologically functional fragments thereof, that include at least the variable domains of the heavy and light chains in a single host cell. Cabilly et al. (U.S. Pat. No. 4,816,567) describes methods for preparing chimeric antibodies.

Immunoconjugates

The invention also provides for the preparation of immunoconjugates and the use of these compounds, or compositions thereof, in methods of medical treatment. For example, any of the proteins described herein can further include an intact antibody or fragment, a single-chain variable fragment (scFv), a diabody, a minibody, or a scFv-Fc fragment. The use of immunoconjugates allows for the targeted delivery of a therapeutic to particular cells (e.g., tumor cells; see, e.g., Mak et al., Primer to the Immune Response, page 277, Academic Press, 2008). Annexin conjugates have also been studied for these applications (see, e.g., Backer et al., "Adapter protein for site-specific conjugation of payloads for targeted drug delivery," Bioconjug. Chem. 15(5):1021-9, 2004, and Tanaka et al., "Preparation and characterization of a disulfide-linked bioconjugate of annexin V with the B-chain of urokinase: an improved fibrinolytic agent targeted to phospholipid-containing thrombi," Biochemistry, 35(3):922-9, 1996). Accordingly, the preparation and study of cytokine immunoconjugates (e.g., cytokines conjugated to annexin) is of great interest for developing new therapeutic methods. For example, a tumor-targeting antibody-(Interferon α) conjugate has been prepared and studied for efficacy in the treatment of lymphoma (Rossi et al., Blood, 114:3864-3871, 2009). Accordingly, such strategies may be applied to the present multimeric proteins (e.g., dimeric cytokines) for the targeted delivery of these compounds to a cell.

EXAMPLES

The following examples are meant to indicate the intrinsic specificity of the labeling components in the aforementioned specifications. A person trained in the art will appreciate the range of these examples demonstrating specificity on cysteine thiols such as annexin Cys-315, which, hitherto, have been challenging to site-specifically label.

In all the examples described herein, annexin V and annexin V-128 retain their biological activity when modified at their respective single cysteines. For example, the $Ca^{2+}$ dependent binding abilities of the modified proteins for 1:1 DOPC:DOPS liposomes (dioleoylphosphatidyl serine=DOPS, dioleoylphosphatidylcholine=DOPC) are not different from the native protein itself.

Mass Spectrometry

Samples for mass spectrometry analysis were prepared using Varian OMIX C4 Ziptips and eluted into 90% acetonitrile, 10% water, with 0.1% formic acid.

For ESI-Mass spec, the samples were infused to a LCQ classic (Thermo) with a flow rate of 10 μL/min. Experimental conditions were as follows: spray voltage at 3 KV and capillary voltage and temperature at 47V and 250 degrees C., respectively. The data were collected continuously for 4 minutes and then were deconvoluted and analyzed by software ProMass (Thermo).

For MALDI, the samples were mixed with 10 mg/ml alpha-cyano-4-hydroxy-cinnamic acid matrix (1:1 volume) before being spotted on a MALDI plate using the dry droplet technique. The samples were analyzed using a Bruker Daltonics Ultraflex TOF/TOF with linear mode and a laser power at 40-50%. Instrument settings were as follows: IS1 at 25.04 kV, IS2 at 23.21 kV, lens at 6.81 kV, and pulsed ion extraction at 18 ns. 500-1000 shots were typically collected for a spectrum. The data were analyzed using software FlexAnalysis by Broker Daltonics.

Example 1

Site-Specific Labeling of Recombinant Human Alpha-1 Antitrypsin or E. coli 30S Ribosomal Protein S4

Recombinant human alpha-1 antitrypsin or E. coli 30S ribosomal protein S4 (1-5 micromolar) was treated with 1 mM 3-bromopyruvate in 100 mM phosphate buffered saline at pH 8.0 at 25° C. After 5 minutes, the protein had completely reacted site-specifically as indicated by the shift of the parent mass to a single peak from 44,440 to 44,S26 (alpha-I), or from 23,338 to 23,424 (S4 protein).

Example 2

Site-Specific Labeling of Alpha-1 Antitrypsin or S4 Protein alpha-1 Antitrypsin or S4 protein (1-5 micromolar) was treated with 1 mM 3-bromoacetophenone in 100 mM phosphate buffered saline at pH 8.0 at 25° C. After five minutes, the protein had completely site-specifically reacted as indicated by the shift of the parent mass at 44,440 to a single peak at 44,SS8 (alpha-I), or from 23,338 to 23,456 (S4 protein).

Example 3

Site-Specific Labeling of Human Annexin V

Human annexin V (1-5 micromolar) was treated with 10 mM 3-bromo acetophenone in 100 mM triethanolamine, pH 8.0, at 25° C. After 20 minutes, the protein had completely reacted site-specifically as indicated by the shift of the parent mass at 35,805 to a single peak at 35,923.

Example 4

Site-Specific Labeling of Human Annexin V by 1,4-Benzoquinone

Wild type human annex in V (1-5 micromolar) was treated with 100 micromolar 1,4-benzoquinone in 100 mM phosphate buffered saline at pH 8.0 at 25° C. After five minutes, the protein had completely reacted site-specifically as indicated by the shift of the parent mass at 35,805 to 35,913 (the combined mass of parent annexin and 1,4.benzoquinone.

Example 5

Site-Specific Labeling of the Primary Ribosomal Protein 84 from E. coli

Ribosomal protein 84 from *E. coli* (1-5 micromolar) was treated with 100 micromolar 1,4-benzoquinone in 100 mM phosphate buffered saline at pH 8.0 at 25° C. After five minutes, the protein had completely reacted as indicated by the shift of the parent mass at 23,338, to 23,446, (the combined mass of parent Ribosomal protein S4 and 1,4-benzoquinone).

Example 6

Site-Specific Labeling of Recombinant Human Alpha-1 Antitrypsin or E. coli 30S Ribosomal Protein S4

Recombinant human alpha-1 antitrypsin or *E. coli* 30S ribosomal protein S4 (1-5 micromolar) was treated with 1 mM 3-bromopyruvate in 100 mM phosphate buffered saline at pH 8.0 at 25° C. After 5 minutes, the protein had completely reacted site-specifically as indicated by the shift of the parent mass to a single peak from 44,440 to 44,S26 (alpha-I), or from 23,338 to 23,424 (S4 protein).

Example 7

Site-Specific Labeling of S4 Protein

S4 protein (1-5 micromolar) was treated with 10 mM 3-bromocyclohex-en-1-one in 100 mM phosphate buffered saline at pH8.0 at 25° C. After 5 min, the protein had completely reacted site specifically as indicated by the shift of the parent mass at 23,338 to a single peak at 23,432.

Example 8

Conjugation of Human Annexin V and the Primary Ribosomal Protein S4 from E. coli by 1,4-Benzoquinone Wild type human annexin V (1-5 micromolar) was treated with 100-1000 micromolar 1,4-benzoquinone in 100 mM phosphate buffered saline at pH 8.0 at 25° C. After five minutes, the protein had completely reacted site-specifically as indicated by the shift of the parent mass at 35,805 to 35,913 (the combined mass of parent annexin and 1,4-benzoquinone). The binary product was purified through centrifuge filtration and used freshly for subsequent reactions described below.

The annexin-benzoquinone was then incubated with 1 molar equivalent of purified *E. coli* 84 protein (free of TCEP, b-ME etc) in pH 8.0 PBS at room temperature for 16 hours. The mass spectrum shows an almost quantitative reaction towards an annexin-84 heterodimer conjugated by a benzoquinone moeity.

Example 9

Conjugation of the Primary Ribosomal Protein 84 from E. coli by 1,4-Benzoquinone to Form Homodimers Ribosomal protein 84 from *E. coli* (1-5 micromolar) was treated with 100 micromolar 1,4-benzoquinone in 100 mM phosphate buffered saline at pH 8.0 at 25° C. After five minutes, the protein had completely reacted as indicated by the shift of the parent mass at 23,338, to 23,446 (the combined mass of parent Ribosomal protein 84 and 1,4-benzoquinone). The binary product was purified through centrifuge filtration and used freshly for subsequent reactions described below.

The ribosomal protein 84-benzoquinone was then incubated with 1 molar equivalent of purified *E. coli* 84 protein (free of TCEP, b-ME etc) in pH8.0 PBS at room temp for two hours. The mass spectrum shows an almost quantitative reaction towards an 84 homodimer conjugated by a benzoquinone moeity.

Example 10

Crosslinking of Annexin V-I,4-Benzoquinone Units by 2,2'-(ethylenedioxy)-diethanethiol Annexin V was first reacted with 1 mM benzoquinone in pH8 PBS buffer at room temp for 5 minutes. This produced a nearly homogeneous product of annexin-benzoquinone as described in Example 7. After centrifuge filtration, the annexin-benzoquinone was further reacted with 10 mM compound of 2,2'-(ethylenedioxy)-diethanethiol in pH8 PBS buffer at room temp for 30 minutes. The mass spectrum suggests a homogeneous product in which one equivalent of 2,2'-(ethylenedioxy)-diethanethiol is added to the annexin-benzoquinone unit. After centrifuge filtration, the tethered product was incubated with one molar equivalent of annexin-benzoquinone in pH8 PBS at room temp overnight. The mass spectrum shows a peak corresponding to the annexin homodimer formed through linkage of annexin-benzoquinone units. The conversion is estimated to be greater than 30%.

Example 11

Reaction of 1,4-Benzoquinones with Cysteine Thiols of Proteins

Site-Specific Formation of the Heterodimer Conjugate of Annexin V and Annexin V-128

10 μM Annexin V was reacted with 1 mM 1,4-benzoquinone in pH 8.0 phosphate buffer at room temperature for 5 minutes. The reaction leads to the complete conversion of annexin V, which becomes fused to 1,4-benzoquinone specifically via a thiol-group (annexin-S-benzoquinone, annexin-S-BQ) as detected by LCQ-MS. After separation of the small molecule fraction by centrifuge filtration, annexin-S-BQ was then incubated with an equimolar amount of annexin V-128, which produces annexin-V conjugated by benzoquinone to annexinV-128 thiol-specifically. The yield of the heteroconjugate is approximately 50%, as shown by SDS-PAGE and LCQ-MS.

Site-Specific Formation of the Heterodimer Conjugate of Annexin V & *E. coli* Ribosomal Protein S4 Mediated by 1,4-Benzoquinone The reaction between *E. coli* ribosomal protein S4 and annexin V was carried out as above. A stable product is obtained in which the S4 protein and annexin V are both thiol-specifically linked to benzoquinone to give the conjugated product as above. The yield is greater than 50%, based on analysis by SDS-PAGE and LCQ-MS.

Site-Specific Formation of the Conjugated Heterodimer of Annexin V & α1-Antiprotease Mediated by 1,4-Benzoquinone The reaction between α1-antiprotease and annexin V was carried out as above. A stable product is obtained in which α1-antiprotease and annexin V are both thiol-specifically linked to benzoquinone to give the conjugated product as above.

Site-Specific Formation of the Homodimer of Annexin V Conjugated by 2,2'-Ethylenedioxy)diethanethiol 10 μM annexin-S-BQ is reacted with 1 mM HS—$(CH_2)_2O(CH_2)_2O(CH_2)_2SH$ (2,2'-ethylenedioxy)diethanethiol, HS-PEG2-SH)) compound in pH 8.0 phosphate buffer at room temperature for 1 hour. This leads to quantitative formation of an annexin-S-BQ-S-PEG2-SH adduct, as detected by LCQ-MS. After separation of the small molecule fraction using centrifuge filtration, annexin-S-BQ-S-PEG2-SH was incubated with an equimolar amount of annexin-S-BQ in pH8.0 phosphate buffer at room temp overnight. A homodimer corresponding to annexin-S-BQ-S-PEG2-S-BQ-S-annexin is produced in 40-60% yield (based on SDS-PAGE and LCQ-MS analyses).

Site-Specific Formation of the Heterodimer of Annexin V and Annexin V-128 Conjugated by 2,2'-Ethylenedioxy)diethanethiol 10 μM Annexin-S-BQ-S-PEG2-SH is reacted with 1 mM benzoquinone in pH 8.0 phosphate buffer at room temperature for 5 minutes. This leads to a complete conversion to an annexin-S-BQ-S-PEG2-S-BQ product as detected by LCQ-MS. After separation of the small molecule fraction using centrifuge filtration, the protein product was then incubated with an equimolar amount of annexin V-128 in pH 8.0 phosphate buffer at room temperature overnight. The reaction with annexin V-128 forms the conjugated product corresponding to annexin-S-BQ-S-PEG2-S-BQ-S-annexin-V-128: in this product, each annexin protein is thiol-specifically linked to their respective benzoquinone rings.

Site-Specific Formation of the Heterodimer of Annexin V and α1-Antiprotease, Conjugated by 2,2'-Ethylenedioxy) diethanethiol 10 μM annexin-S-BQ-S-PEG2-SH is reacted with 1 mM benzoquinone in pH8.0 phosphate buffer at room temperature for 5 minutes. This leads to complete conversion to an annexin-S-BQ-S-PEG2-S-BQ product based on analysis by LCQ-MS. After separation of the small molecule fraction using centrifuge filtration, the protein product is then incubated with an equimolar amount of alpha-1 antitrypsin. The reaction with alpha-1 antitrypsin produces annexin-S-BQ-S-PEG2-S-BQ-alpha-antiprotease as indicated by SDS-PAGE.

Site-Specific Thiolation of 1,4-Benzoquinone Leading to Proteins Conjugated to PEG Polymers 10 μM annexin-BQ is treated with a five molar excess of PEG-SH (20 KDa) in pH8.0 phosphate buffer at room temperature overnight. A product corresponding to annexin-V-BQ-S-PEG with a yield approximating 50-60% as estimated by SDS-PAGE is obtained.

1 mM PEG-SH (20 KDa) is treated with a 10× molar excess of benzoquinone in pH8.0 phosphate buffer at room temperature for 5 minutes to yield a product corresponding to PEG-S-BQ. After separation of the small molecule fraction using centrifuge filtration, 10-20 μM PEG-S-BQ is further reacted with an equimolar amount of annexin V-128 or alpha-1 antitrypsin in pH8.0 phosphate buffer at room temperature overnight. The reaction leads to the pegylated products of PEG-S-BQ-annexin-V 128 or PEG-S-BQ-alpha-1 antiprotease with yields approximating 30-40%, as detected by SDS-PAGE.

Example 12

Site-Specific Crosslinking of $PEGNH_2$ (20K) to Alpha-1 Antiprotease via 4-Bromomethylbenzoic acid 10 μM alpha-1 antiprotease is incubated with a 5× molar excess of 4-bromomethyl-benzoylamide of $PEGNH_2$ (20 KDa) [prepared from 4-bromomethylbenzoic acid and ethyl chloroformate, which is then added in excess to $PEGNH_2$ 20K and stirred overnight] in pH8.0 phosphate buffer at room temperature overnight. The reaction with alpha-1 antiprotease yields 4-alpha-1-S-benzyl-PEGamide, as detected by SDS-PAGE.

Example 13

Site-Specific Crosslinking of $PEGNH_2$ (20K) to Annexin V-128 Via 4-Bromoacetylbenzoic acid 10 μM annexin V-128 is treated with a 5× molar excess of 3- or 4-bromoacetylbenzoyl-PEGamide (prepared from 3- or 4-bromoacetylbenzoic acid and ethyl chloroformate, which is then added in excess to $PEGNH_2$-20K and stirred overnight) in pH 8.0 phosphate buffer at room temperature. SDS-PAGE and MALDI mass spectrometry indicated the formation of the conjugated pegylated product.

Example 14

Synthesis and Study of an Annexin V/IL-10 Conjugate (Scheme 32)

Annexin V or annexin V-128 (concentration varied from several μg/ml to several mg/ml) was incubated with 10 mM PLP in 25 mM PBS (pH 6.5) at 37° C. for 4-16 hours. After the incubation, the sample was subjected to centrifuge filtration to remove excess PLP from solution and then analyzed by mass spectrometry. Various aminoxy substrates, which form oximes with carbonyl species, were used to distinguish the N-terminal keto-amide product of the annexin protein from that of the parent and to demonstrate that the product was obtained in excellent yield.

The resulting annexin ketoamide was then incubated with 100 mM bis-1,6-aminoxy hexane at room temperature for 4 to 16 hours. The reaction mixture was constantly shaken. After terminating the reaction, the sample was subjected to centrifuge filtration to remove the excess bis-aminoxy compound from solution. The 6-aminoxy-oxime of annexin V or V-128 was thus obtained.

Scheme 32

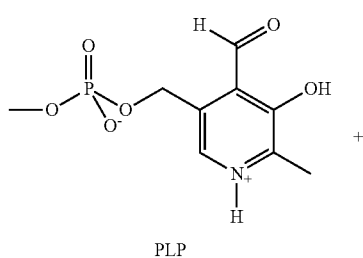

PLP

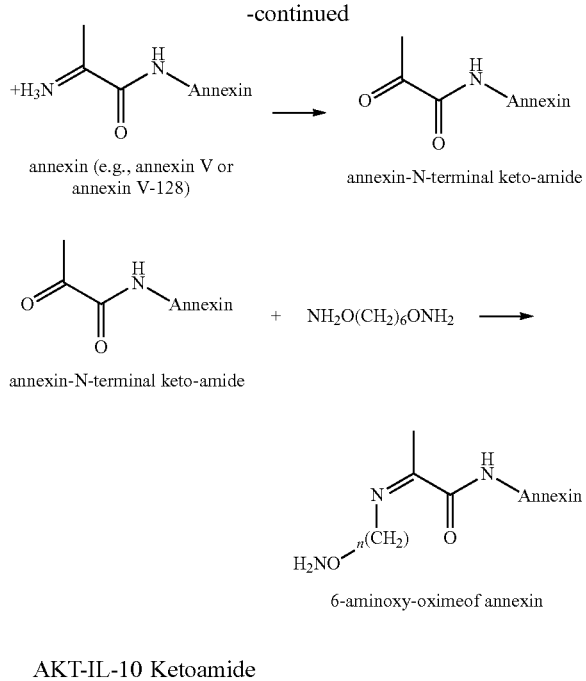

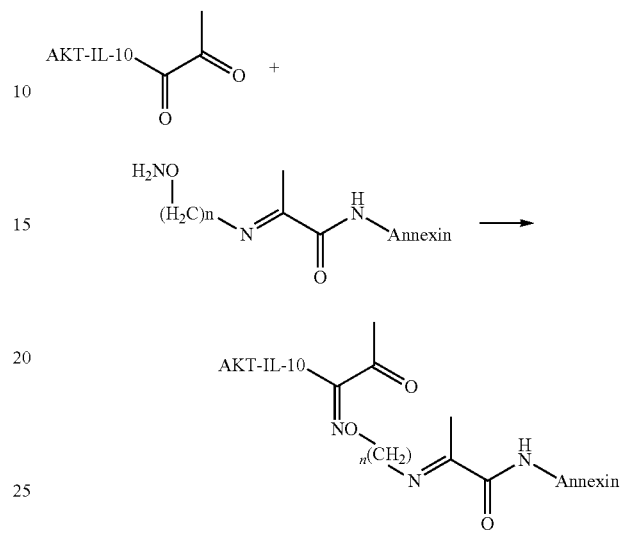

annexin protein and IL-10 (Scheme 33) was established by mass spectrometry analysis of the enzymatically digested heterodimer.

AKT-IL-10 Ketoamide

IL-10 was cloned and expressed with the tripeptide N-terminal extension alanine-lysine-threonine (AKT) to give AKT-IL-10. (Witus et al., *J Am Chem Soc.* 132:16812-7, 2010). The AKT-IL-10 was then treated with PLP as above for 16 hours; the small molecule fraction was then separated, and the N-terminal keto amide of AKT-IL-10 was thus obtained.

Reaction Between the N-Terminal Ketoamide of AKT-IL-10 and 6-Aminoxyannexin

6-Aminoxy-annexin, obtained as described above, was incubated with 30 micromolar N-terminal ketoamide of AKT-IL-10 at room temperature overnight, at pH 6.5 in 25 mM PBS. The structure of the crosslinked product of the Crosslinking of 6-Aminoxy-Annexin and 6-Aminoxy-AKT-IL-10 to Form the Conjugate Aminoxy annexin V oxime was incubated with 1 mM terephthaldehyde at room temperature for 10 min (buffer, pH). The reaction to form the mono-aldoxime with the protein species is complete within 10 minutes. Only one of the two aldehyde groups of the substrate is consumed. The annexin-aldehyde (was then treated with the 6-aminoxy-AKT-IL-10. Using conditions described herein, the 6-aminoxy-oxime of AKT-IL-10 was then condensed with the annexin mono-aldoxime to give the terephthaldehyde-linked conjugate (Scheme 34).

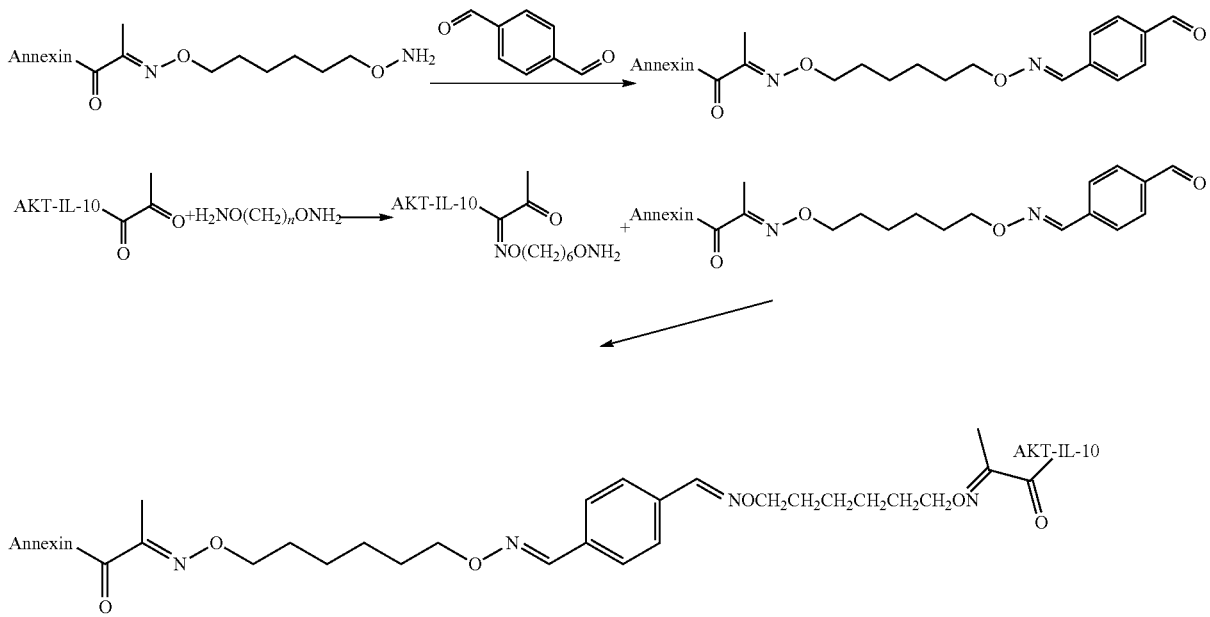

Evaluation of the Efficacy of Annexin:IL-10 Conjugates in an Arthritis Animal Model.

The annexin:IL-10 conjugates A and B of Scheme 35 were each evaluated for their therapeutic efficacy in chronic inflammatory arthritis in mice by injecting them into joints. TNF transgenic (TNF-Tg) mice were used as a model of chronic inflammatory arthritis. Either conjugate A or conjugate B was injected into joints of TNF-Tg mice. MRI and lymphatic imaging were used during the 4-months following injection to assess changes in synovial volume and lymph flow from joint tissues to local draining lymph nodes. Joint inflammation, bone erosion, and cartilage loss were examined by histologic analyses. Lymphatic vessel formation was assessed using immunohistochemistry. Intra-articular administration of either conjugate A or conjugate B significantly attenuated the increase in synovial volume and increased lymphatic vessel number in joint sections compared to IL-10 during the 4-month period. This was accompanied by reduced inflammation area, bone erosion, cartilage loss, and osteoclast numbers. Lymph flow from joints to local draining lymph nodes was slower in TNF-Tg mice than in wild-type littermates and was significantly improved with either conjugate A or conjugate B as compared with treatment by IL-10. Conjugate A or conjugate B also exhibited greater duration of action and less systemic toxicity than IL-10.

Scheme 35

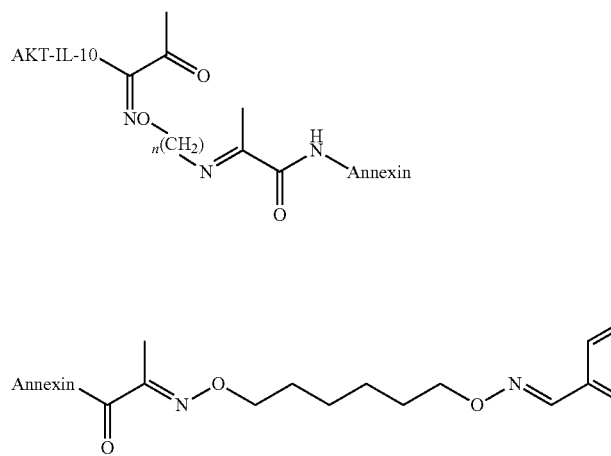

Conjugate A

Conjugate B

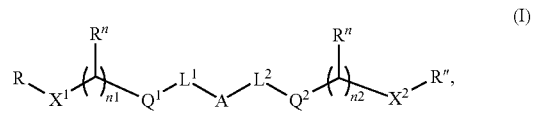

Example 15

Reaction of 1,3-Cyclopentadiene with the 1:1 Conjugate of Annexin V and 1,4-Benzoquinone Cyclopentadiene was freshly prepared and dissolved in methanol to a final concentration of 100 mM. Annexin V-1,4-benzoquinone, prepared according to the methods described herein, was also prepared to a 20 µM final concentration in 25 mM phosphate buffer (pH=6.5).

Annexin V-1,4-benzoquinone (100 µL) was then mixed with cyclopentadiene (20 µL) at 4° C. for 20 minutes. Analysis by mass spectroscopy confirmed that the Diels-Alder adduct was formed. Annexin V under the same conditions does not react with cyclopentadiene.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A conjugate having the following structure, $$R-X^1-(\phantom{X})_{n1}-Q^1-L^1-A-L^2-Q^2-(\phantom{X})_{n2}-X^2-R'', \quad (I)$$

with $R^n$ substituents on each bracketed unit wherein

A is optionally substituted aryl, optionally substituted heteroaryl, or a substructure according to the formula —Ar$^{Z1}$—Z—Ar$^{Z2}$—, wherein each of Ar$^{Z1}$ and Ar$^{Z2}$ is, independently, optionally substituted aryl or optionally substituted heteroaryl, and Z is a covalent bond, O, S, NR$^{Z1}$, wherein R$^{Z1}$ is H or optionally substituted C1-6 alkyl, an optionally substituted C1-20 alkylene, a polyethylene glycol of the structure (CH$_2$CH$_2$O)(CH$_2$CH$_2$O)$_n$(CH$_2$CH$_2$), wherein n is an integer between 0-1000, or a linking group having the structure —X$^{Z1}$-(Q$^{Z1}$)$_{n3}$-R$^{Z2}$-(Q$^{Z1}$)$_{n4}$ X$^{Z1}$, wherein each of n3 and n4 is, independently, 0 or 1, each $X^{Z1}$ is, independently, a covalent bond, O, S, or $NR^{Z1}$, each $Q^{Z1}$ is, independently, C(=O), S(=O), or $S(=O)_2$, and $R^{Z2}$ is optionally substituted C1-20 alkylene or polyethyleneoxide $(CH_2CH_2O)(CH_2CH_2O)_n(CH_2CH_2)$, wherein n is an integer between 0-1000;

each of $L^1$ and $L^2$ is, independently, a covalent bond or optionally substituted C1-C6 alkylene;

$Q^1$ is a covalent bond, C(=O), $S(=O)_2$, or C1 alkylene;

$Q^2$ is C(=O) or $S(=O)_2$;

each of n1 and n2 is, independently, 0 or 1;

$X^1$ is S;

$X^2$ is O, S, or $NR^X$, wherein $R^X$ is H or optionally substituted C1-6 alkyl;

each $R''$ is, independently, H or optionally substituted C1-6 alkyl;

R is a globular protein; and

R" is a protein, a biologically active agent, or a biologically compatible agent;

wherein each said protein independently comprises at least three amino acids linked by peptide bonds; and wherein optional substituents, when present, are independently selected from the group consisting of $C_{1-6}$ alkyl, $C_{2-6}$ alkenyl, $C_{2-6}$ alkynyl, aryl, heteroaryl, —F, —Cl, —Br, —I, —$N_3$, —$NO_2$, —CN, —OC(=O)$R^B$, —C(=O)$R^B$, —O$R^B$, —$NR^B$C(=O)$R^C$, —C(=O)$NR^AR^B$, —$NR^AR^B$, —$CO_2$H, —$CO_2R^B$, —OC(=O)$NR^BR^C$, —NRC(=O)O$R^B$, —OH, —NC, —S(=O)$_2$O$R^A$, —S(=O)$_2NR^AR^B$, —$NR^A$S(=O)$_2R^B$, and —S(=O)$_2R^A$, wherein each of $R^A$, $R^B$, and $R^C$ is independently H, $C_{1-6}$ alkyl, $C_{2-6}$ alkenyl, $C_{2-6}$ alkynyl, aryl, or heteroaryl.

2. The conjugate of claim 1, wherein
$L^1$ is a covalent bond;
$L^2$ is a covalent bond;
n1 is 1;
n2 is 1; and
$Q^1$ is C(=O), $S(=O)_2$, or $CH_2$.

3. The conjugate of claim 1, wherein R" is a protein.

4. The conjugate of claim 1, wherein one or both of R and R" is a protein that is an annexin protein, an antibody, a cytokine, a wild-type protein that includes a free cysteine residue, or a protein modified to include a free cysteine residue, or wherein R" is a biologically active or biologically compatible agent that is a polymer, nucleic acid, carbohydrate, small molecule therapeutic agent, imaging agent, or diagnostic agent.

5. The conjugate of claim 1, wherein A is optionally substituted phenyl, optionally substituted naphthyl, or optionally substituted biphenyl.

6. The conjugate of claim 1, wherein said conjugate has a structure according to one of the following formulas,

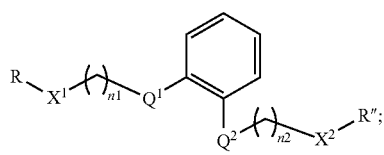

(II-A)

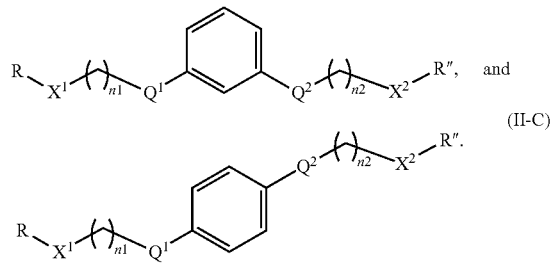

(II-B)

(II-C)

7. A method of preparing a conjugate having a structure according to claim 1, comprising (a) contacting a compound according to the following formula,

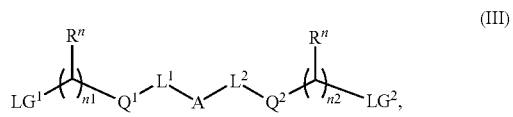

(III)

wherein

A is optionally substituted aryl, optionally substituted heteroaryl, or a substructure according to the formula —$Ar^{Z1}$—Z—$Ar^{Z2}$—, wherein each of $Ar^{Z1}$ and $Ar^{Z2}$ is, independently, optionally substituted aryl or optionally substituted heteroaryl, and Z is a covalent bond, O, S, $NR^{Z1}$, wherein $R^{Z1}$ is H or optionally substituted C1-6 alkyl, an optionally substituted C1-20 alkylene, a polyethylene glycol of the structure $(CH_2CH_2O)(CH_2CH_2O)_n(CH_2CH_2)$, wherein n is an integer between 0-1000, or a linking group having the structure —$X^{Z1}$-$(Q^{Z1})_{n3}$-$R^{Z2}$-$(Q^{Z1})_{n4}$ $X^{Z1}$, wherein each of n3 and n4 is, independently, 0 or 1, each $X^{Z1}$ is, independently, a covalent bond, O, S, or $NR^{Z1}$, each $Q^{Z1}$ is, independently, C(=O), S(=O), or $S(=O)_2$, and $R^{Z2}$ is optionally substituted C1-20 alkylene or $(CH_2CH_2O)(CH_2CH_2O)_n(CH_2CH_2)$, wherein n is an integer between 0-1000;

each of $L^1$ and $L^2$ is, independently, a covalent bond or optionally substituted C1-C6 alkylene;

C(=O), $S(=O)_2$, or C1 alkylene;

$Q^2$ is C(=O) or $S(=O)_2$;

each of n1 and n2 is, independently, 0 or 1;

each $R''$ is, independently, H or optionally substituted C1-6 alkyl; and each of $LG^1$ and $LG^2$ is, independently, a leaving group, with a nucleophilic compound having the structure $RX^1$H, wherein R is a globular protein, and $X^1$ is S; and (b) contacting the product of step (a) with a nucleophilic compound having the structure $R''X^2$H, wherein R" is a protein or a biologically active or biologically compatible agent, and $X^2$ is O, S, or $NR^X$, wherein RX is H or optionally substituted C1-6 alkyl;

wherein each said protein independently comprises at least three amino acids linked by peptide bonds; and wherein optional substituents, when present, are independently selected from the group consisting of $C_{1-6}$ alkyl, $C_{2-6}$ alkenyl, $C_{2-6}$ alkynyl, aryl, heteroaryl, —F, —Cl, —Br, —I, —N$_3$, —NO$_2$, —CN, —OC(=O)R$^B$, —C(=O)R$^B$, —OR$^B$, —NR$^B$C(=O)R$^C$, —C(=O)NR$^A$R$^B$, —NR$^A$R$^B$, —CO$_2$H, —CO$_2$R$^B$, —OC(=O)NR$^B$R$^C$, —NRC(=O)OR$^B$, —OH, —NC, —S(=O)$_2$OR$^A$, —S(=O)$_2$NR$^A$R$^B$, —NR$^A$S(=O)$_2$R$^B$, and —S(=O)$_2$R$^A$, wherein each of R$^A$, R$^B$, and R$^C$ is independently H, $C_{1-6}$ alkyl, $C_{2-6}$ alkenyl, $C_{2-6}$ alkynyl, aryl, or heteroaryl.

8. A pharmaceutical composition comprising the conjugate of claim 1 and a pharmaceutically acceptable excipient.

9. A method of delivering a therapeutic agent to a cell undergoing necrosis or apoptosis, said method comprising contacting said cell or tissue with an agent that is the conjugate of claim 1.

10. The method of claim 9, wherein one of R and R" is an annexin protein.

* * * * *